United States Patent
Asuma et al.

(10) Patent No.: US 10,071,958 B2
(45) Date of Patent: Sep. 11, 2018

(54) METHOD FOR PRODUCING ALPHA-SUBSTITUTED CYSTEINE OR SALT THEREOF OR SYNTHETIC INTERMEDIATE OF ALPHA-SUBSTITUTED CYSTEINE

(71) Applicant: API Corporation, Tokyo (JP)

(72) Inventors: Yuuki Asuma, Kanagawa (JP);
Hisatoshi Uehara, Kanagawa (JP);
Tomoko Maeda, Kanagawa (JP);
Yasuyo Saito, Kanagawa (JP); Ryoma Miyake, Kanagawa (JP); Hiroshi Kawabata, Kanagawa (JP)

(73) Assignee: API Corporation, Tokyo (JP)

( * ) Notice: Subject to any disclaimer, the term of this patent is extended or adjusted under 35 U.S.C. 154(b) by 139 days.

(21) Appl. No.: 14/888,576

(22) PCT Filed: May 1, 2014

(86) PCT No.: PCT/JP2014/062115
§ 371 (c)(1),
(2) Date: Nov. 2, 2015

(87) PCT Pub. No.: WO2014/178433
PCT Pub. Date: Nov. 6, 2014

(65) Prior Publication Data
US 2016/0083341 A1     Mar. 24, 2016

(30) Foreign Application Priority Data
May 2, 2013   (JP) .................................. 2013-097172

(51) Int. Cl.
| | | |
|---|---|---|
| *C07C 319/06* | (2006.01) | |
| *C07C 323/52* | (2006.01) | |
| *C07C 323/58* | (2006.01) | |
| *C07D 277/14* | (2006.01) | |
| *C07C 319/02* | (2006.01) | |
| *C12P 13/12* | (2006.01) | |
| *C07C 319/14* | (2006.01) | |
| *C07C 319/20* | (2006.01) | |
| *C07C 323/60* | (2006.01) | |

(52) U.S. Cl.
CPC .......... *C07C 319/06* (2013.01); *C07C 319/02* (2013.01); *C07C 319/14* (2013.01); *C07C 319/20* (2013.01); *C07C 323/52* (2013.01); *C07C 323/58* (2013.01); *C07C 323/60* (2013.01); *C07D 277/14* (2013.01); *C12P 13/12* (2013.01)

(58) Field of Classification Search
CPC ... C07C 319/06; C07C 323/52; C07C 323/58; C07D 277/14
See application file for complete search history.

(56) References Cited

U.S. PATENT DOCUMENTS

| | | |
|---|---|---|
| 4,895,952 A | 1/1990 | Marty et al. |
| 4,994,624 A | 2/1991 | Roberts |
| 8,106,035 B2 * | 1/2012 | Posner .................. C07C 401/00 |
| | | 514/167 |
| 8,993,800 B2 | 3/2015 | Ohishi et al. |
| 2006/0105435 A1 | 5/2006 | Ohishi et al. |
| 2010/0197934 A1 | 8/2010 | Ohishi et al. |

FOREIGN PATENT DOCUMENTS

| | | |
|---|---|---|
| WO | WO-01/72702 A2 | 10/2001 |
| WO | WO-03/106689 A1 | 12/2003 |
| WO | WO-2007/106022 A2 | 9/2007 |

OTHER PUBLICATIONS

Kedrowski, B. J. Org. Chem. 2003, 68, 5403-5406.*
Han et al. Chem. Commun. 2006, 1757-1759.*
Ohishi et al. Tetrahedron Letters 2007, 48, 3437-3440 (Year: 2007).*
Nagasawa et al. J. Med. Chem. 1987, 30, 1373-1378 (Year: 1987).*
Han et al. Chem. Commun. 2007, 3444-3446 (Year: 2007).*
d'Ischia et al. Synthetic Communcations 1987, 17, 1577-1585 (Year: 1987).*
Masterson et al., "An Improved Method for the Preparation of Protected (R)-2-Methylcysteine: Solution-Phase Synthesis of a Glutathione Analogue", Synlett, 2010, No. 19, pp. 2941-2943.
Kedrowski, "Synthesis of Orthongonally Protected (R)- and (S)-2-methylcysteine via an Enzymatic Desymmeterization and Curtius Rearrangement", J. Org. Chem, Jun. 27, 2003, vol. 68, No. 13, pp. 5403-5406.

(Continued)

Primary Examiner — Matthew P Coughlin
(74) Attorney, Agent, or Firm — Marshall, Gerstein & Borun LLP

(57) ABSTRACT

According to the present invention, it becomes possible to perform a process for converting into an α-substituted cysteine represented by general formula (1) or a salt thereof at low cost and on an industrial scale by employing a process that is routed through a compound represented by general formula (3) to a compound represented by general formula (6). Particularly, by employing a process that is routed through a compound represented by general formula (7-2), it becomes possible to detach a tert-butyl protection group in a simple manner and to produce the compound represented by general formula (1) with high purity. Furthermore, by employing a process that is routed through tert-butylthiomethanol or a process that is routed through a compound represented by general formula (9), it becomes possible to produce a compound represented by general formula (2) without generating bischloromethylether that is an oncogenic substance. In the production of an α-substituted-D-cysteine or a salt thereof, it becomes possible to perform a process for converting the compound represented by general formula (2) into a compound represented by general formula (3S) in one step by allowing an enzyme or the like to act on the compound represented by general formula (2).

9 Claims, 2 Drawing Sheets
Specification includes a Sequence Listing.

(56) References Cited

OTHER PUBLICATIONS

Masterson et al., "A Divergent Approach to the Preparation of Cysteine and Serine Analogs", J. Pept. Sci., Nov. 2008, vol. 14, No. 11, pp. 1151-1162.
Han et al., "Novel Structural Motifs Consisting of Chiral Thiazolines: Synthesis, Molecular Recognition, and Anticancer Activity", Chem. Eur. J., 2007, vol. 13, No. 11, pp. 3026-3038.
Liu et al., "Efficient Production of (S)-naproxen with (R)-substrate Recycling Using an Overexpressed Carboxylesterase BsE-NP01", Appl. Biochem. Biotechnol., Nov. 2010, vol. 162, No. 6, pp. 1574-1584.
Search Report in International Application No. PCT/JP2014/062115 dated Jul. 29, 2014.
Office Action in JP Application No. 2015-514876 dated Feb. 2, 2016, 9 pages.
Kedrowski, "Synthesis of Orthogonally Protected (R)- and (S)-2-methylcysteine via an Enzymatic Desymmeterization and Curtius Rearrangement", J. Org. Chem, Jun. 27, 2003, vol. 68, No. 13, pp. 5403-5406.
Transmittal of International Preliminary Report on Patentability and Written Opinion in International Application No. PCT/JP2014/062115 dated Nov. 12, 2015, 9 pages.

\* cited by examiner

CENP1 (*Bacillus subtilis* IFO3108-derived) reaction product

Racemic body sample (control)

METHOD FOR PRODUCING ALPHA-SUBSTITUTED CYSTEINE OR SALT THEREOF OR SYNTHETIC INTERMEDIATE OF ALPHA-SUBSTITUTED CYSTEINE

TECHNICAL FIELD

The present invention relates to a method for producing an α-substituted cysteine or a salt thereof, which is useful as an intermediate for pharmaceuticals and the like, or an intermediate for synthesis of an α-substituted cysteine.

BACKGROUND ART

Among α-substituted cysteines, optically active α-substituted cysteines are especially useful as intermediates for pharmaceuticals. Various methods are conventionally known as methods for producing α-substituted cysteines and salts thereof (for example, Patent Document 1).

However, the conventional methods have been impractical since stable production in an industrial scale has been difficult because of, for example, requirement of a low-temperature reaction using an expensive base such as butyllithium, and/or requirement of many laborious steps using a large amount of expensive reagents.

As a method that does not require an expensive reagent or a low-temperature reaction unlike the method in Patent Document 1, Patent Document 2 describes a method for producing α-methyl-D-cysteine in which racemic N-carbamoyl-α-methylcysteine is subjected to D-isomer-specific cyclization by hydantoinase to produce D-5-methyl-5-thiomethylhydantoin, followed by hydrolysis, decarbamoylation, and sulfur atom deprotection (elimination of the tert-butyl group) of the D-5-methyl-5-thiomethylhydantoin. This α-methyl-D-cysteine is an optically active α-substituted cysteine, and useful as an intermediate for a therapeutic agent for hyperferremia.

Patent Document 3 describes a method for obtaining benzyl-protected α-methyl-D-cysteine by allowing *Bacillus licheniformis* protease to act on a diester having benzyl-protected thiol to provide an (S)-monoester, and then converting the isocyanate group generated by Curtius rearrangement to an amino group.

Non-patent Document 1 discloses a method for obtaining tert-butyl-protected α-methyl-D-cysteine, wherein a diester protected with a tert-butyl group instead of a benzyl group is subjected to (R)-monoesterification using pig liver esterase, and then to tert-butyl esterification of the carboxyl group and hydrolysis of the methyl ester to obtain an (S)-monoester, followed by converting the isocyanate group generated by Curtius rearrangement to a carbamate-protected amino group, and then deprotecting the carbamate protection.

Non-patent Document 2 describes a production method in which the tert-butyl-protected diester described in Non-patent Document 1, tert-butylthiochloromethane, and methyl dialkylmalonate are reacted in the presence of a base. The document also describes a method for producing tert-butylthiochloromethane, in which tert-butyl mercaptan, paraformaldehyde, and hydrogen chloride are reacted in dichloromethane. It is known that, in this process, contacting of formaldehyde with hydrogen chloride causes generation of bis-chloromethylether (for example, Non-patent Document 3).

PRIOR ART DOCUMENTS

Patent Documents

Patent Document 1: WO 2001/072702
Patent Document 2: WO 2003/106689
Patent Document 3: WO 2007/106022

Non-Patent Documents

Non-patent Document 1: Journal of Organic Chemistry (2003), 68(13), p. 5403-5406
Non-patent Document 2: Synlett (2010), (19), p. 2941-2943
Non-patent Document 3: Chemische Berichte, 88, 1737 (1955)

SUMMARY OF THE INVENTION

In the method described in Patent Document 2, a long reaction time is required for each of the steps of hydrolysis, decarbamoylation, and sulfur atom deprotection of hydantoin, so that the production efficiency is low. Moreover, since optical resolution is used as the method for obtaining the D-isomer, the N-carbamoyl-α-methylcysteine to be subjected to the optical resolution needs to be produced in an amount of at least two molar equivalents with respect to the amount of interest. In addition, a disposal process is required for the unnecessary L-isomer.

In the method described in Patent Document 3, the (S)-monoester can be obtained from the diester at a theoretical yield of 100% (that is, the benzyl-protected α-methyl-D-cysteine can also be obtained from the diester at a theoretical yield of 100%). Therefore, the above-mentioned problem in Patent Document 2 does not occur. However, in order to obtain α-methyl-D-cysteine, the benzyl group on the sulfur atom, which is a protecting group, needs to be eliminated. In general, Birch reduction using liquid ammonia and sodium metal is employed for elimination of a benzyl group. In this method, very low temperature conditions are required, and sodium metal, which is highly ignitable, needs to be used, so that the method is not suitable for industrial production. Moreover, since the deprotected α-methyl-D-cysteine is a compound whose extraction with an organic solvent is difficult, removal of the metal salt generated during the reaction is difficult.

In the method described in Non-patent Document 1, the elimination of the tert-butyl group is achieved by heating in the presence of hydrochloric acid. Therefore, the problem in Patent Document 3 does not occur. However, since the operation of conversion of the (R)-monoester to the (S)-monoester is laborious, the method is not suitable for industrial production. Moreover, the optical purity of the (S)-monoester obtained by this method depends on the (R)-monoester, and the optical purity of the (R)-monoester is 91% e.e. Thus, the optical purity is insufficient for providing an intermediate for production of a pharmaceutical.

In cases where a tert-butyl-protected diester is produced by the method described in Non-patent Document 2, bis-chloromethylether, which is highly carcinogenic and, especially in Japan, designated as a substance whose production is prohibited under Article 55 of the Safety and Health Act, may be generated.

The present invention was made in view of the above circumstances, and aims to provide a practical method that enables simpler, quicker, and safer production of an α-substituted cysteine or a salt thereof which is useful as an intermediate for pharmaceuticals and the like using an easily available and inexpensive material, which method is applicable to stable, industrial-scale production of the α-substituted cysteine or the salt thereof.

As a result of intensive study on a method for producing an α-substituted cysteine or a synthetic intermediate thereof, the present inventors discovered that, by allowing a reaction to proceed through 2-oxo-1,3-thiazolidine-4-carboxylic acid, elimination of a tert-butyl protecting group, which has conventionally required a very long reaction time, can be achieved in a short time. The present inventors also discovered that, by employing a process of synthesis from tert-butylthiomethanol or dialkyl 2-[(tert-butylthio)methyl]malonate, dialkyl 2-(tert-butylthio)methyl-2-substituted malonate can be safely produced without generating bis-chloromethylether, which is carcinogenic.

In addition, the present inventors discovered that, in production of an α-substituted-D-cysteine, which is especially useful as an intermediate for a therapeutic agent for hyperferremia, the process of converting a dialkyl 2-[(tert-butylthio)methyl]-2-substituted malonate to an alkyl (S)-2-[(tert-butylthio)methyl]-2-substituted malonate, which has been laborious, can be carried out in one step by enzymatic reaction and the like.

That is, the present invention relates to the following.

[1] A method for producing an α-substituted cysteine represented by General Formula (1):

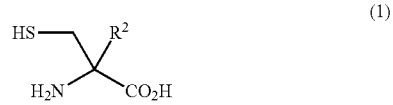

(wherein $R^2$ represents a $C_1$-$C_4$ alkyl group)
or a salt thereof, the method comprising the steps of:

(i) allowing a base or an acid; or an enzyme having an activity to hydrolyze an ester group, a cell having an ability to produce the enzyme, a processed product of the cell, and/or a culture liquid containing the enzyme obtained by culturing the cell; to act on a compound represented by General Formula (2):

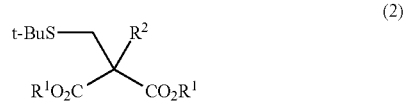

(wherein each $R^1$ independently represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ represents a $C_1$-$C_4$ alkyl group),
to obtain a compound represented by General Formula (3):

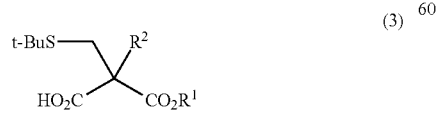

(wherein $R^1$ and $R^2$ have the same meanings as $R^1$ and $R^2$ in the General Formula (2));

(ii) allowing a condensing agent or an acid halogenating agent to act on the compound represented by the General Formula (3), to obtain a compound represented by General Formula (4):

(wherein $R^1$ and $R^2$ have the same meanings as $R^1$ and $R^2$ in the General Formula (2); X represents —OP(O)(OPh)$_2$, —OP(O)(OEt)$_2$, —OC(O)OR$^3$, or a halogen atom; and $R^3$ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted);

(iii) allowing an azidation agent to act on the compound represented by the General Formula (4), to obtain a compound represented by General Formula (5):

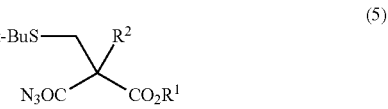

(wherein $R^1$ and $R^2$ have the same meanings as $R^1$ and $R^2$ in the General Formula (2));

(iv) converting, by Curtius rearrangement reaction, the compound represented by the General Formula (5), to obtain a compound represented by General Formula (6):

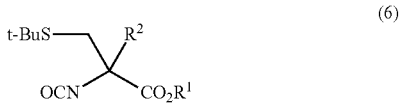

(wherein $R^1$ and $R^2$ have the same meanings as $R^1$ and $R^2$ in the General Formula (2)); and (v) subjecting the compound represented by the General Formula (6) to a process of converting the isocyanate group to an amino group, a process of hydrolyzing the ester group, and a process of removing the tert-butyl group by action of an acid.

[2] The method for producing an α-substituted cysteine or a salt thereof according to [1], wherein
in the Step (i), the enzyme is
(A) a protein comprising the amino acid sequence of SEQ ID NO: 4, 6, 8, 10, 12, 14, 16, or 18;
(B) a protein having an identity of not less than 35% to the amino acid sequence of SEQ ID NO: 4, 6, 8, 10, 12, 14, 16, or 18, and having an activity to hydrolyze the compound represented by the General Formula (2) for conversion into a compound represented by General Formula (3S):

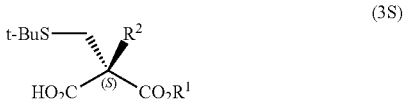

(wherein R¹ and R² have the same meanings as R¹ and R² in the General Formula (3)), which is a compound represented by the General Formula (3) and having an (S)-configuration; or (C) a protein comprising the amino acid sequence of SEQ ID NO: 4, 6, 8, 10, 12, 14, 16, or 18 in which one or several amino acids are deleted, substituted, and/or added, and having an activity to hydrolyze the compound represented by the General Formula (2) for conversion into a compound represented by General Formula (3S), which is a compound represented by the General Formula (3) and having an (S)-configuration; and the α-substituted cysteine represented by the General Formula (1) is an α-substituted cysteine represented by the following General Formula (1S) having an (S)-configuration:

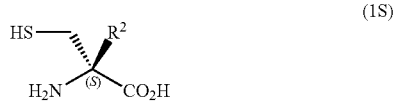

(1S)

(wherein R² has the same meaning as R² in the General Formula (1)).

[3] A method for producing a compound represented by General Formula (3S):

(3S)

(wherein R¹ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and R² represents a $C_1$-$C_4$ alkyl group),
which is a compound represented by the General Formula (3):

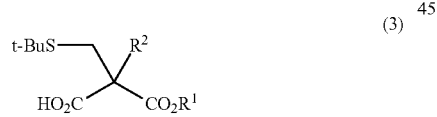

(3)

(wherein R¹ and R² have the same meanings as R¹ and R² in the General Formula (3S))
and having an (S)-configuration, the method comprising the step of:

(i) allowing an enzyme having an activity to hydrolyze an ester group, a cell having an ability to produce the enzyme, a processed product of the cell, and/or a culture liquid containing the enzyme obtained by culturing the cell, to act on a compound represented by General Formula (2):

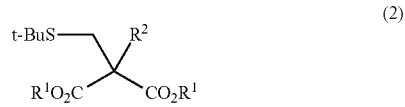

(2)

(wherein R¹ and R² have the same meanings as R¹ and R² in the General Formula (3S)).

[4] The method for producing a compound represented by the General Formula (3S) according to [3], wherein the enzyme is (A) a protein comprising the amino acid sequence of SEQ ID NO: 4, 6, 8, 10, 12, 14, 16, or 18;

(B) a protein having an identity of not less than 35% to the amino acid sequence of SEQ ID NO: 4, 6, 8, 10, 12, 14, 16, or 18, and having an activity to hydrolyze the compound represented by the General Formula (2) for conversion into the compound represented by the General Formula (3S) having the (S)-configuration; or (C) a protein comprising the amino acid sequence of SEQ ID NO: 4, 6, 8, 10, 12, 14, 16, or 18 in which one or several amino acids are deleted, substituted, and/or added, and having an activity to hydrolyze the compound represented by the General Formula (2) for conversion into the compound represented by the General Formula (3S) having the (S)-configuration.

[5] A method for producing a compound represented by General Formula (4-1):

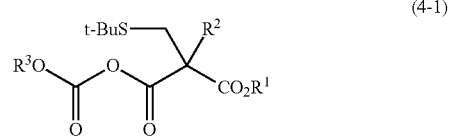

(4-1)

(wherein R¹ and R³ each independently represent a $C_1$-$C_{10}$ alkyl group which is optionally substituted, a $C_7$-$C_{20}$ aralkyl group which is optionally substituted, or a $C_6$-$C_{12}$ aryl group which is optionally substituted, and R² represents a $C_1$-$C_4$ alkyl group), the method comprising the step of:

(ii) allowing a chloroformic ester to act on a compound represented by General Formula (3):

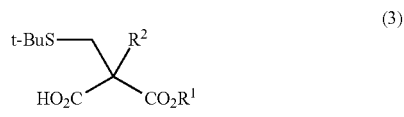

(3)

(wherein R¹ and R² have the same meanings as R¹ and R² in the General Formula (4-1)).

[6] A method for producing a compound represented by General Formula (5):

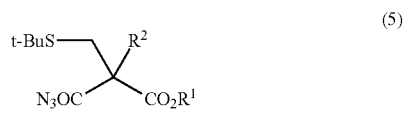

(5)

(wherein R¹ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and R² represents a $C_1$-$C_4$ alkyl group), the method comprising the step of:

(iii) allowing a metal azide to act on a compound represented by General Formula (4-1):

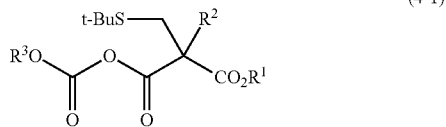

(wherein $R^1$ and $R^2$ have the same meanings as $R^1$ and $R^2$ in the General Formula (5), and $R^3$ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted).

[7] A method for producing a compound represented by General Formula (6):

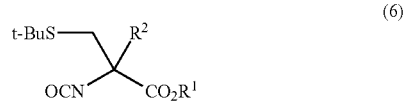

(wherein $R^1$ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ represents a $C_1$-$C_4$ alkyl group),
the method comprising the step of:

(iv) converting, by Curtius rearrangement reaction, a compound represented by General Formula (5):

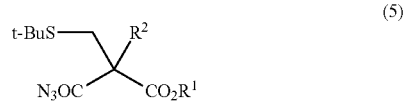

(wherein $R^1$ and $R^2$ have the same meanings as $R^1$ and $R^2$ in the General Formula (6)).

[8] A method for producing an α-substituted cysteine represented by General Formula (1):

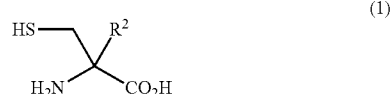

(wherein $R^2$ represents a $C_1$-$C_4$ alkyl group)
or a salt thereof, the method comprising the step of:

(v) subjecting a compound represented by General Formula (6):

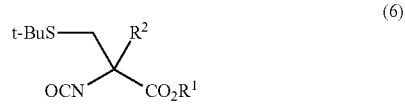

(wherein $R^1$ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ has the same meaning as $R^2$ in the General Formula (1))
to a process of converting the isocyanate group to an amino group, a process of hydrolyzing the ester group, and a process of removing the tert-butyl group by action of an acid.

[9] The method for producing an α-substituted cysteine represented by General Formula (1):

(wherein $R^2$ represents a $C_1$-$C_4$ alkyl group)
or a salt thereof according to [8], wherein the step (v) comprises the steps of:

(vi-1) allowing an acid to act on a compound represented by General Formula (6):

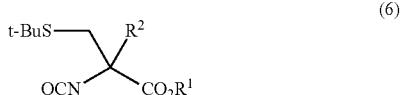

(wherein $R^1$ and $R^2$ have the same meanings as $R^1$ and $R^2$ in the General Formula (6)) to construct a thiazolidinone ring, for conversion into a compound represented by General Formula (7-1):

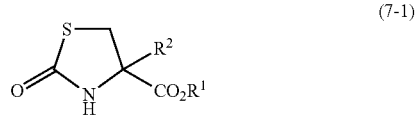

(wherein $R^1$ and $R^2$ have the same meanings as $R^1$ and $R^2$ in the General Formula (6));

(vi-2) allowing an acid or a base to act on the compound represented by the General Formula (7-1) to hydrolyze the ester group, to obtain a compound represented by General Formula (7-2):

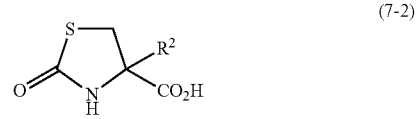

(wherein $R^2$ has the same meaning as $R^2$ in the General Formula (7-1)); and (vii) allowing an acid or a base to act on the compound represented by the General Formula (7-2) to open the thiazolidinone ring, to produce the α-substituted cysteine represented by the General Formula (1) or the salt thereof.

[10] A method for producing a compound represented by General Formula (7-1):

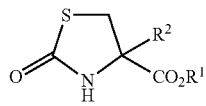
(7-1)

(wherein $R^1$ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ represents a $C_1$-$C_4$ alkyl group), the method comprising the step of:

(vi-1) allowing an acid to act on a compound represented by General Formula (6):

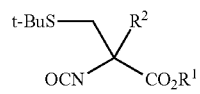
(6)

(wherein $R^1$ and $R^2$ have the same meanings as $R^1$ and $R^2$ in the General Formula (7-1)) to construct a thiazolidinone ring.

[11] A method for producing a compound represented by General Formula (7-2):

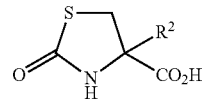
(7-2)

(wherein $R^2$ represents a $C_1$-$C_4$ alkyl group), the method comprising the step of:

(vi-2) allowing an acid or a base to act on a compound represented by General Formula (7-1):

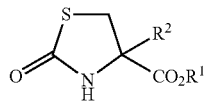
(7-1)

(wherein $R^1$ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ has the same meaning as $R^2$ in the General Formula (7-2)) to hydrolyze the ester group.

[12] A method for producing an α-substituted cysteine represented by General Formula (1):

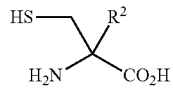
(1)

(wherein $R^2$ represents a $C_1$-$C_4$ alkyl group) or a salt thereof, the method comprising the steps of:

(vii) allowing an acid or a base to act on a compound represented by General Formula (7-2):

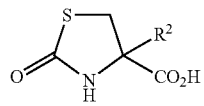
(7-2)

(wherein $R^2$ has the same meaning as $R^2$ in the General Formula (1)) to open the thiazolidinone ring

[13] A compound represented by General Formula (4-1):

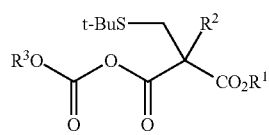
(4-1)

(wherein $R^1$ and $R^3$ each independently represent a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ represents a $C_1$-$C_4$ alkyl group).

[14] A compound represented by General Formula (5):

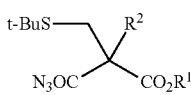
(5)

(wherein $R^1$ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ represents a $C_1$-$C_4$ alkyl group).

[15] A compound represented by General Formula (6):

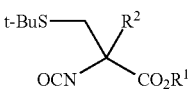
(6)

(wherein $R^1$ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ represents a $C_1$-$C_4$ alkyl group).

[16] A compound represented by General Formula (7S):

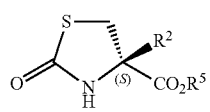
(7S)

(wherein $R^2$ represents a $C_1$-$C_4$ alkyl group, and $R^5$ represents a hydrogen atom, or a $C_1$-$C_{10}$ alkyl group which is optionally substituted, a $C_7$-$C_{20}$ aralkyl group which is optionally substituted, or a $C_6$-$C_{12}$ aryl group which is optionally substituted).

[17] A method for producing a compound represented by General Formula (2):

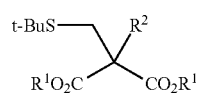
(2)

(wherein each $R^1$ independently represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ represents a $C_1$-$C_4$ alkyl group),
the method comprising the step of:
(xi) allowing an alkylating agent to act on a compound represented by General Formula (9):

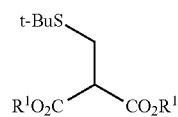
(9)

(wherein $R^1$ has the same meaning as $R^1$ in the General Formula (2)) in the presence of a base.

[18] A method for producing a compound represented by General Formula (2):

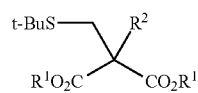
(2)

(wherein each $R^1$ independently represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ represents a $C_1$-$C_4$ alkyl group),
the method comprising the steps of:
(viii) reacting tert-butyl mercaptan with formaldehyde to obtain tert-butylthiomethanol;
(ix) reacting tert-butylthiomethanol with a chlorinating agent in the presence of a base to obtain tert-butylthiochloromethane; and
(x) allowing tert-butylthiochloromethane to act on a compound represented by General Formula (8):

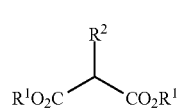
(8)

(wherein $R^1$ has the same meaning as $R^1$ in the General Formula (2), and $R^2$ represents a $C_1$-$C_4$ alkyl group) in the presence of a base, to obtain the compound represented by the General Formula (2).

Effects of the Invention

According to the production method of the present invention, an α-substituted cysteine or a salt thereof can be simply, quickly, and safely produced using an easily available and inexpensive material, and stable, industrial-scale production of the α-substituted cysteine or the salt thereof can be achieved.

EMBODIMENTS FOR CARRYING OUT THE INVENTION

Figure 1:
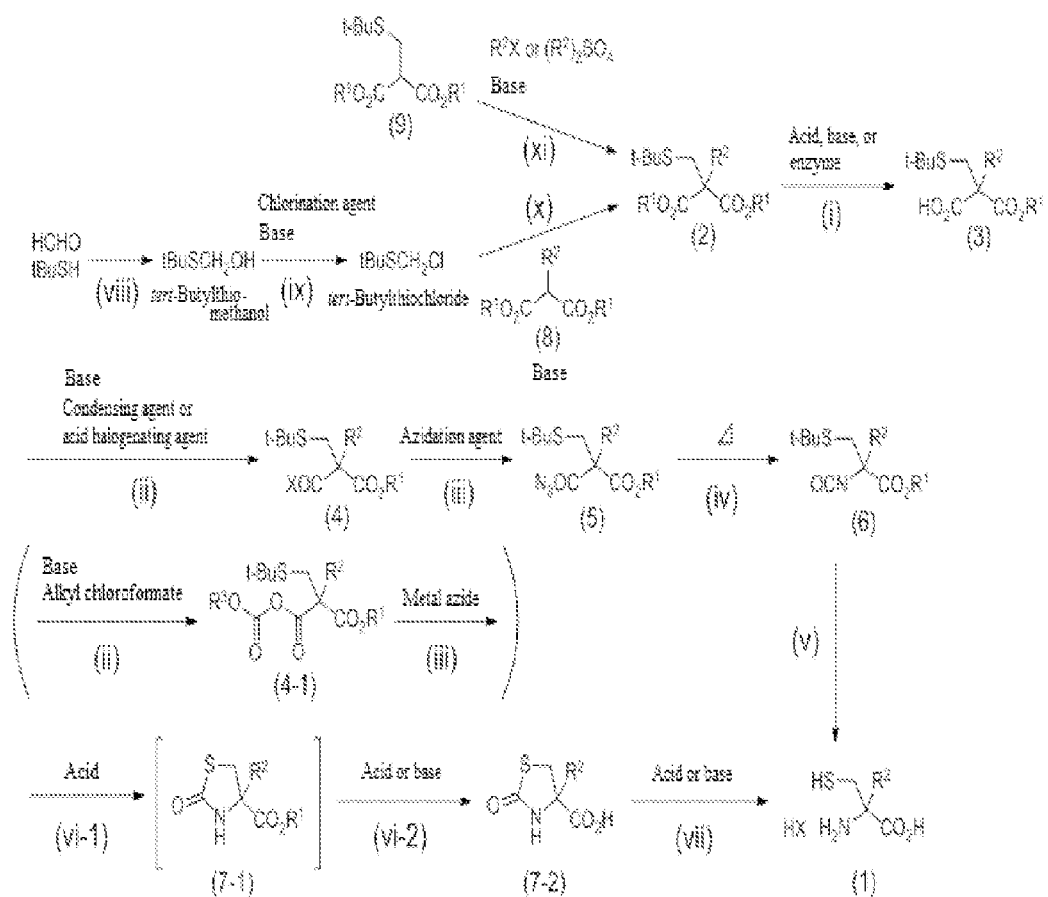
FIG. 1 is a diagram showing an embodiment of the production method of the present invention.

Method for Producing α-Substituted Cysteine Represented by General Formula (1) or Salt Thereof]

The method for producing an α-substituted cysteine represented by the General Formula (1) shown below or a salt thereof of the present invention comprises the step (i) and the subsequent steps (ii), (iii), and (iv). The production method of the present invention preferably comprises, before the step (i), the step (xi), or the steps (viii), (xi), and (x). The production method of the present invention preferably comprises, after the step (iv), the step (v), especially preferably the steps (vi-1), (vi-2), and (vii).

General Formula (1)

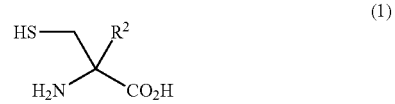
(1)

(wherein $R^2$ represents a $C_1$-$C_4$ alkyl group)
<Step (i)>
First, the step (i) is described below.
The step (i) is a step of allowing a base or an acid; or an enzyme having an activity to hydrolyze an ester group, a cell having an ability to produce the enzyme, a processed product of the cell, and/or a culture liquid containing the enzyme obtained by culturing the cell (the "enzyme having an activity to hydrolyze an ester group, cell having an ability to produce the enzyme, processed product of the cell, and/or culture liquid containing the enzyme obtained by culturing the cell" may be hereinafter referred to as "enzyme and/or the like of the present invention"); to act on a compound represented by General Formula (2):

(2)

(wherein each $R^1$ independently represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ represents a $C_1$-$C_4$ alkyl group), to obtain a compound represented by General Formula (3):

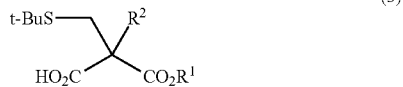

(3)

(wherein $R^1$ and $R^2$ have the same meanings as $R^1$ and $R^2$ in the General Formula (2)).

The compound represented by General Formula (2) can be produced, as described in Non-patent Document 2, by reacting tert-butylthiochloromethane and dialkyl methyl malonate in the presence of a base. This document also describes a method for producing tert-butylthiochloromethane, in which tert-butyl mercaptan, paraformaldehyde, and hydrogen chloride are reacted in dichloromethane. However, according to Non-patent Document 3, contacting of formaldehyde with hydrogen chloride may cause generation of bis-chloromethylether, which is highly carcinogenic. Thus, this production method is unfavorable from the viewpoint of health of the operator.

Accordingly, the production method for the compound represented by General Formula (2) is preferably a production method comprising the steps (viii)-(x), in which tert-butylthiochloromethane is produced without bringing formaldehyde into contact with hydrogen chloride, or the step (xi), in which tert-butylthiochloromethane is not used. The steps (viii)-(xi) are described later.

In the compound represented by General Formula (2), examples of the alkyl group of the "$C_1$-$C_{10}$ alkyl group which is optionally substituted" as $R^1$ include $C_1$-$C_{10}$ linear, branched, or cyclic alkyl groups such as methyl, ethyl, isopropyl, n-propyl, n-butyl, isobutyl, sec-butyl, tert-butyl, n-pentyl, isopentyl, tert-pentyl, neopentyl, n-hexyl, cyclopropyl, cyclobutyl, cyclopentyl, and cyclohexyl. Examples of the substituent optionally contained in the alkyl group include $C_1$-$C_6$ alkoxy groups such as methoxy and ethoxy; halogen atoms such as a fluorine atom, chlorine atom, bromine atom, and iodine atom; and nitro. The number of substituents is not limited, and, in cases where there are two or more substituents in the alkyl group, the substituents may be of the same type or different types.

In the compound represented by General Formula (2), examples of the aralkyl group of the "$C_7$-$C_{20}$ aralkyl group which is optionally substituted" as $R^1$ include benzyl, 2-phenylethyl, 1-phenylethyl, 1-phenylpropyl, 2-phenylpropyl, and 3-phenylpropyl. Examples of the substituent optionally contained in the aralkyl group include $C_1$-$C_6$ alkyl groups such as methyl, ethyl, and isopropyl; $C_1$-$C_6$ alkoxy groups such as methoxy and ethoxy; halogen atoms such as a fluorine atom, chlorine atom, bromine atom, and iodine atom; and nitro. The number of substituents is not limited, and, in cases where there are two or more substituents in the aralkyl group, the substituents may be of the same type or different types.

In the compound represented by General Formula (2), examples of the aryl group of the "$C_6$-$C_{12}$ aryl group which is optionally substituted" as $R^1$ include phenyl, 1-naphthyl, and 2-naphthyl. Examples of the substituent optionally contained in the aryl group include $C_1$-$C_6$ alkyl groups such as methyl, ethyl, and isopropyl; $C_1$-$C_6$ alkoxy groups such as methoxy and ethoxy; halogen atoms such as a fluorine atom, chlorine atom, bromine atom, and iodine atom; and nitro. The number of substituents is not limited, and, in cases where there are two or more substituents in the aryl group, the substituents may be of the same type or different types.

Among the groups described above, $R^1$ is preferably a $C_1$-$C_{10}$ unsubstituted linear or branched alkyl group such as methyl, ethyl, isopropyl, n-propyl, n-butyl, isobutyl, sec-butyl, tert-butyl, n-pentyl, isopentyl, tert-pentyl, neopentyl, or n-hexyl from the viewpoint of their availability, more preferably a $C_1$-$C_4$ unsubstituted linear or branched alkyl group such as methyl, ethyl, isopropyl, n-propyl, n-butyl, isobutyl, sec-butyl, or tert-butyl from the viewpoint of their inexpensiveness, still more preferably a $C_1$-$C_4$ unsubstituted linear alkyl group such as methyl, ethyl, n-propyl, or n-butyl from the viewpoint of their reactivity with acids, bases and enzymes. In particular, in cases where an enzyme is used in the step (i), the smaller the structure of $R^1$, the better it is incorporated into the reaction site of the enzyme, leading to a higher reaction rate. Thus, methyl or ethyl is most preferred.

In the compound represented by General Formula (2), the two $R^1$s are not necessarily the same, and may be different from each other. In cases where the $R^1$s are different from each other, two enantiomers, the (R)-isomer and the (S)-isomer, are present as the compound represented by the General Formula (2). The mixing ratio between these enantiomers is not limited.

In the compound represented by General Formula (2), $R^2$, that is, the $C_1$-$C_4$ alkyl group, needs to be the same as $R^2$ in the compound of interest represented by General Formula (1). Examples of $R^2$ include methyl, ethyl, n-propyl, isopropyl, n-butyl, isobutyl, sec-butyl, and tert-butyl. From the viewpoint of ease of production, $C_1$-$C_4$ unsubstituted linear alkyl groups such as methyl, ethyl, n-propyl, and n-butyl are more preferred. In particular, in cases where the enzyme and/or the like of the present invention is used, the smaller the structure of $R^2$, the better it is incorporated into the reaction site of the enzyme, leading to a higher reaction rate. Thus, methyl or ethyl is still more preferred. $R^2$ needs to be methyl in cases where α-methyl-D-cysteine, which is useful as an intermediate for a therapeutic agent for hyperferremia, is produced among the later-described α-substituted cysteines represented by General Formula (1) and salts thereof.

Examples of the compound represented by General Formula (2) include the following compounds.

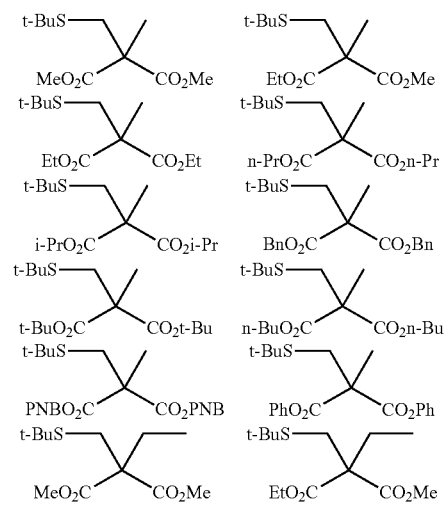

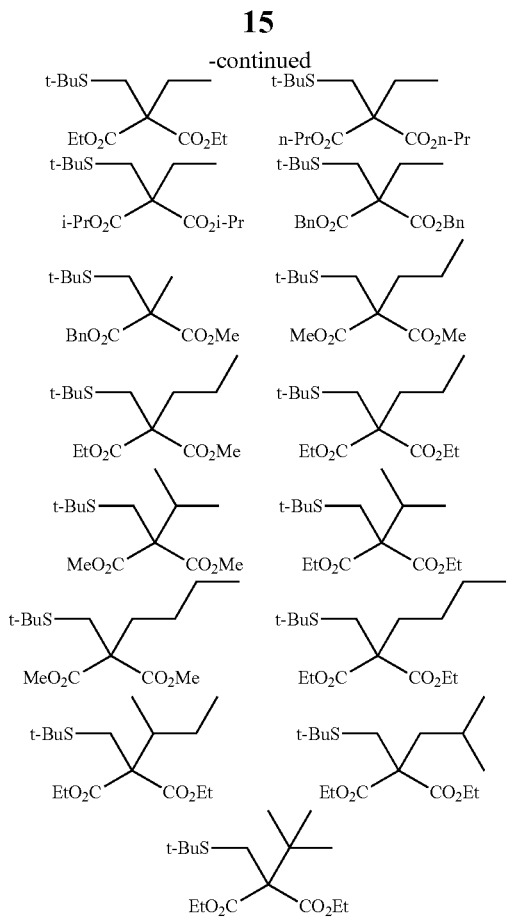

Among the compounds described above, the following compounds are preferred as the compound represented by General Formula (2).

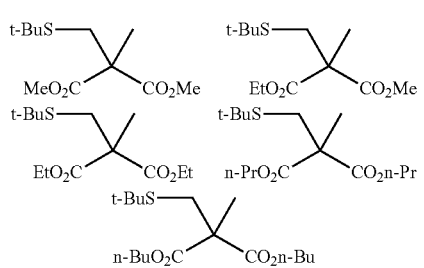

By allowing a base or an acid; or an enzyme having an activity to hydrolyze an ester group, a cell having an ability to produce the enzyme, a processed product of the cell, and/or a culture liquid containing the enzyme obtained by culturing the cell; to act on a compound represented by General Formula (2) to perform hydrolysis, a compound represented by General Formula (3) can be obtained.

In the compound represented by General Formula (3), $R^1$ and $R^2$ have the same meanings as $R^1$ and $R^2$ in the above-mentioned General Formula (2).

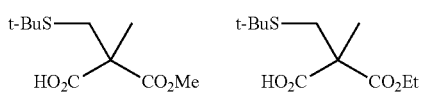

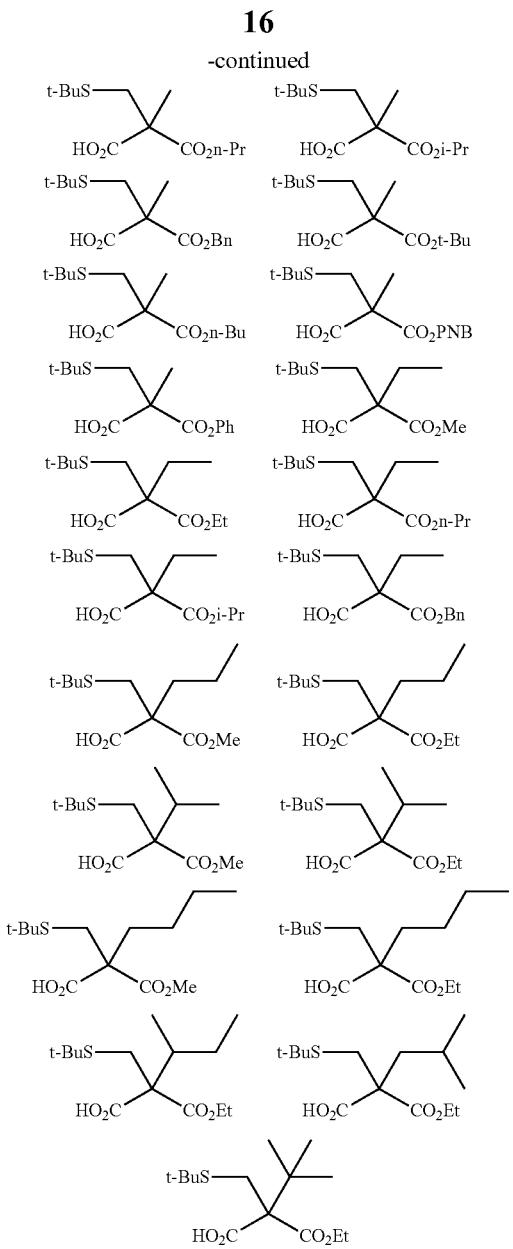

Examples of the compound represented by General Formula (3) include the following compounds.

Among the compounds described above, the following compounds are preferred as the compound represented by General Formula (3).

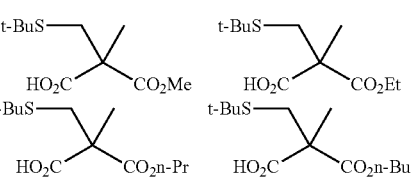

The compound represented by General Formula (3) may be a chiral compound which selectively contains either one of the (S)-isomer compound represented by General Formula (3S):

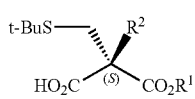
(3S)

(wherein $R^1$ and $R^2$ have the same meanings as $R^1$ and $R^2$ in the General Formula (3)) or the (R)-isomer compound represented by General Formula (3R):

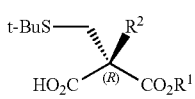
(3R)

(wherein $R^1$ and $R^2$ have the same meanings as $R^1$ and $R^2$ in the General Formula (3)), or may be a racemic compound having a weight ratio of 1:1. The compound is preferably an (S)-isomer compound since, by the steps (ii), (iii), and (iv) described later, the (S)-isomer can be converted to an α-substituted-D-cysteine or a salt thereof, which is useful as an intermediate for pharmaceuticals and the like, among the α-substituted cysteines represented by General Formula (1) and salts thereof.

Examples of the compound represented by the General Formula (3S) include the following compounds.

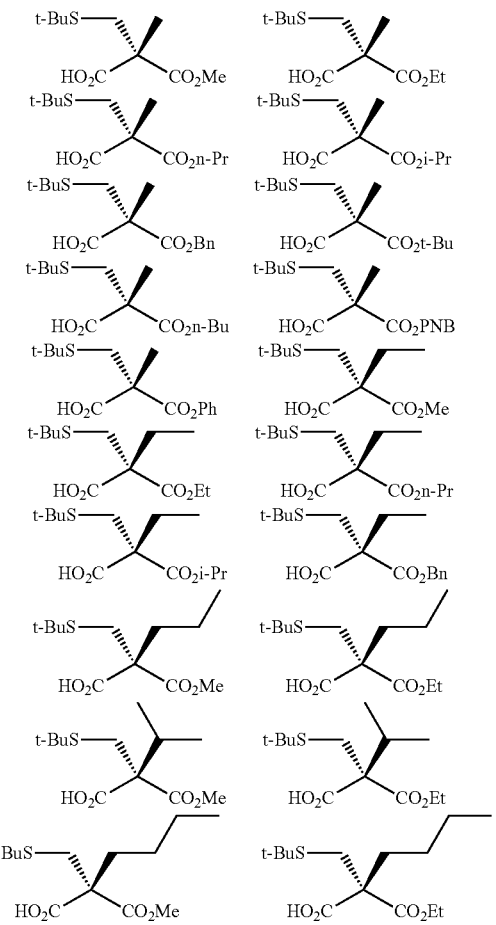

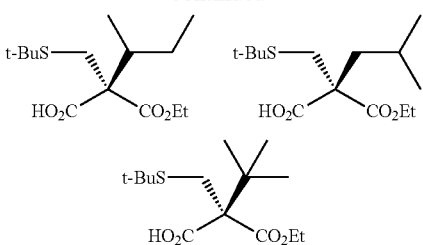

Among the compounds described above, the following compounds are preferred as the compound represented by General Formula (3S).

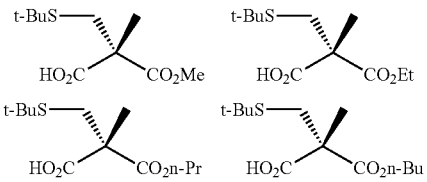

Examples of the compound represented by the General Formula (3R) include the following compounds.

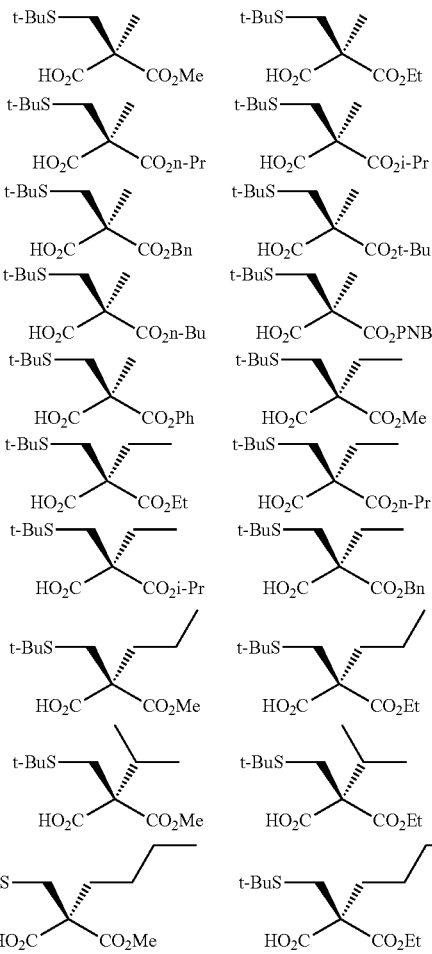

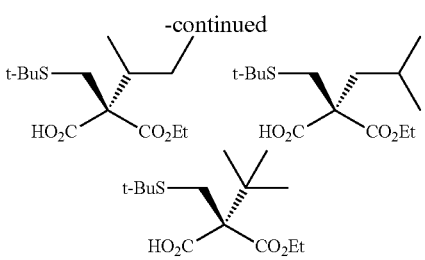

Among the compounds described above, the following compounds are preferred as the compound represented by General Formula (3R).

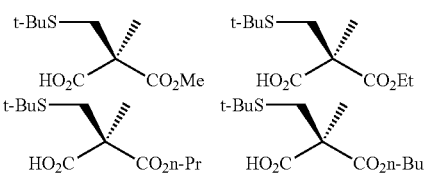

In the step (i), a base or an acid, or the enzyme and/or the like of the present invention is/are allowed to act on a compound represented by the General Formula (2). The respective cases are described below in detail.
(Cases of Reaction with a Base)

In cases where a base is allowed to act for the hydrolysis, examples of the base include alkali metal hydroxides such as sodium hydroxide, lithium hydroxide, and potassium hydroxide; and alkali metal carbonates such as lithium carbonate, sodium carbonate, and potassium carbonate. These bases may be used individually, or as a mixture of two or more of these.

The amount of the base used may be appropriately set within the range of, for example, 0.7 molar equivalent to 10 molar equivalents with respect to the amount of the compound represented by General Formula (2). From the viewpoint of the yield and the cost, the amount is preferably 0.9 molar equivalent to 2 molar equivalents. From the viewpoint of prevention of further hydrolysis of the ester group in the compound represented by General Formula (3), the amount is more preferably 0.9 molar equivalent to 1.2 molar equivalents.

In cases where a base is allowed to act, the reaction temperature may be appropriately selected within the range of, for example, −50° C. to 80° C. For enabling simple control of the temperature to suppress side reactions, the reaction temperature is preferably within the range of 0° C. to 40° C.

In cases where a base is allowed to act, the reaction time may be appropriately selected within the range of, for example, 0.5 hour to 50 hours. The reaction time is preferably within the range of 2 hours to 10 hours.

In cases where a base is allowed to act, the reaction solvent is usually water alone, or a mixed solvent of water and an organic solvent. Examples of the organic solvent include alcohols such as glycerol, ethylene glycol, methanol, ethanol, 1-propanol, 2-propanol, and t-butanol; ketones such as acetone, 2-butanone, and methylisobutyl ketone; ethers such as diethyl ether, di-n-propyl ether, diisopropyl ether, di-n-butyl ether, methyl isopropyl ether, methyl-t-butyl ether, ethyl-t-butyl ether, cyclopentyl methyl ether, tetrahydrofuran, dioxane, and 1,2-dimethoxyethane; aliphatic hydrocarbons such as n-hexane and n-heptane; esters such as ethyl acetate, isopropyl acetate, and butyl acetate; aromatic hydrocarbons such as benzene, toluene, and xylene; nitriles such as acetonitrile and propionitrile; halogenated hydrocarbons such as dichloromethane, chloroform, carbon tetrachloride, and 1,2-dichloroethane; dimethylsulfoxide; and dimethylformamide.

In particular, in order to increase the reaction rate, a uniform reaction mixture is preferably provided using water, in which alkali metal hydroxides and alkali metal carbonates are highly soluble, and a water-soluble solvent in which the compound represented by General Formula (2) is highly soluble and which is highly miscible with water. Examples of the water-soluble solvent include alcohols such as glycerol, ethylene glycol, methanol, ethanol, 1-propanol, 2-propanol, and t-butanol; ketones such as acetone and 2-butanone; ethers such as tetrahydrofuran, dioxane, and 1,2-dimethoxyethane; nitriles such as acetonitrile and propionitrile; dimethylsulfoxide; and dimethylformamide. In particular, from the viewpoint of ease of removal of the solvent by distillation, methanol, ethanol, acetone, and tetrahydrofuran are more preferred because of their low boiling points.

In the step (i) of the present invention, the reaction is more preferably carried out with a base than with an acid, since a base can suppress the side reaction of hydrolyzing both, rather than one, of the ester groups contained in General Formula (2), and therefore enables production of the compound represented by General Formula (3) with high yield.
(Cases of Reaction with an Acid)

In cases where an acid is allowed to act on the compound represented by General Formula (2) to perform hydrolysis, examples of the acid include inorganic acids such as hydrochloric acid, sulfuric acid, phosphoric acid, hydrogen bromide, hydrogen fluoride, and hydrogen iodide; and organic acids such as trifluoroacetic acid, trifluoromethanesulfonic acid, methanesulfonic acid, and p-toluenesulfonic acid (p-toluenesulfonic acid is preferably monohydrate; the same applies hereinafter). These acids may be used individually, or as a mixture of two or more thereof.

The amount of the acid used may be appropriately set within the range of, for example, 0.1 molar equivalent to 20 molar equivalents with respect to the amount of the compound represented by General Formula (2). From the viewpoint of the yield and the cost, the amount is preferably 1.0 molar equivalent to 10 molar equivalents.

In cases where an acid is allowed to act, the reaction temperature may be appropriately selected within the range of, for example, 0° C. to 200° C. For reducing the reaction time and enabling simple control of the temperature, the reaction temperature is preferably within the range of 30° C. to 100° C.

In cases where an acid is allowed to act, the reaction time may be appropriately selected within the range of, for example, 0.5 hour to 50 hours. The reaction time is preferably within the range of 2 hours to 20 hours.

In cases where a base is allowed to act, the reaction solvent is usually water alone, or a mixed solvent of water and an organic solvent. Examples of the organic solvent include ketones such as acetone, 2-butanone, and methylisobutyl ketone; ethers such as diethyl ether, di-n-propyl ether, diisopropyl ether, di-n-butyl ether, methyl isopropyl ether, methyl-t-butyl ether, ethyl-t-butyl ether, cyclopentyl methyl ether, tetrahydrofuran, dioxane, and 1,2-dimethoxyethane; aliphatic hydrocarbons such as n-hexane and n-heptane; esters such as ethyl acetate, isopropyl acetate, and butyl acetate; aromatic hydrocarbons such as benzene, toluene, and xylene; nitriles such as acetonitrile and propionitrile; halogenated hydrocarbons such as dichloromethane, chloroform, carbon tetrachloride, and 1,2-dichloroethane; dimethylsulfoxide; and dimethylformamide.

From the viewpoint of stability against acids, preferred examples of the organic solvent include aliphatic hydrocarbons such as n-hexane and n-heptane; esters such as ethyl acetate, isopropyl acetate, and butyl acetate; aromatic hydrocarbons such as benzene, toluene, and xylene; nitriles such as acetonitrile and propionitrile; halogenated hydrocarbons such as dichloromethane, chloroform, carbon tetrachloride, and 1,2-dichloroethane; dimethylsulfoxide; and dimethylformamide.

(Cases of Reaction with the Enzyme and/or the Like of the Present Invention)

The compound represented by General Formula (3) can also be obtained by allowing the enzyme and/or the like of the present invention, that is, an enzyme having an activity to hydrolyze an ester group, a cell having an ability to produce the enzyme, a processed product of the cell, and/or a culture liquid containing the enzyme obtained by culturing the cell, to act on a compound represented by General Formula (2).

In particular, in cases where a chiral compound which selectively contains either one of General Formulae (3S) and (3R) is to be obtained as General Formula (3), the enzyme and/or the like of the present invention is preferably allowed to act rather than the above-described acid or base, from the viewpoint of stereoselectivity.

The enzyme having an activity to hydrolyze an ester group that may be used in the production method of the present invention is not limited as long as the enzyme has the activity, and examples of the enzyme include enzymes comprising the amino acid sequence of (A) SEQ ID NO: 4, 6, 8, 10, 12, 14, 16, or 18. These are carboxyesterase NP derived from Bacillus subtilis.

In the present invention, their homologues having the enzyme activity may also be used. Examples of the homologues include (B) and (C) described below.

(B) A protein having an identity of not less than 35% to the amino acid sequence of SEQ ID NO: 4, 6, 8, 10, 12, 14, 16, or 18, and having an activity to hydrolyze a compound represented by the General Formula (2) for conversion into a compound represented by General Formula (3S):

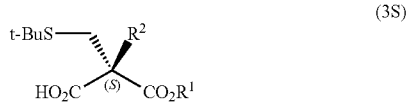

(3S)

(wherein $R^1$ and $R^2$ have the same meanings as $R^1$ and $R^2$ in the General Formula (3)), which is a compound represented by the General Formula (3) and having an (S)-configuration.

(C) A protein comprising the amino acid sequence of SEQ ID NO: 4, 6, 8, 10, 12, 14, 16, or 18 in which one or several amino acids are deleted, substituted, and/or added, and having an activity to hydrolyze a compound represented by the General Formula (2) for conversion into a compound represented by General Formula (3S), which is a compound represented by the General Formula (3) and having an (S)-configuration.

The protein (B) herein may have an identity of not less than 35%, preferably not less than 50%, more preferably not less than 80%, especially preferably not less than 95%, most preferably not less than 98% to the amino acid sequence of SEQ ID NO: 4, 6, 8, 10, 12, 14, 16, or 18, as long as the protein has an activity to hydrolyze an ester group. For example, the identity search for the protein can be carried out using a program such as FASTA or BLAST (Basic Local Alignment Search Tool) against GenBank or DNA Databank of JAPAN (DDBJ).

Examples of the protein (C) include proteins comprising the amino acid sequence of SEQ ID NO: 4, 6, 8, 10, 12, 14, 16, or 18 in which one or several amino acids are deleted, substituted, and/or added, as long as the activity to hydrolyze an ester group is not deteriorated. More specifically, the term "several" herein means not more than 20, preferably not more than 10, more preferably not more than 5.

The enzyme having an activity to hydrolyze an ester group used in the present invention can be obtained by isolating DNA encoding the enzyme from an arbitrary microorganism having the enzyme activity using a probe prepared based on the nucleotide sequence of a gene encoding a part of, or the whole enzyme, and then transforming a host organism such as E. coli with the DNA, followed by allowing the host organism to express the enzyme.

The enzyme having an activity to hydrolyze an ester group used in the present invention can also be obtained by purification from cells of a microorganism having the enzyme activity, for example, a Bacillus bacterium.

Examples of the Bacillus bacterium include Bacillus licheniformis, Bacillus subtilis, and Bacillus stearothermophilus. Their strains are available from National Institute of Technology and Evaluation. Alternatively, the strains can be obtained from ATCC (American Type Culture Collection) in cases where they are described in the online catalog (http://www.atcc.org/) by ATCC.

In the production method of the present invention, the enzyme may be allowed to act on a compound represented by General Formula (2). Alternatively, instead of the enzyme, or in addition to the enzyme, a cell having an ability to produce the enzyme, a processed product of the cell, and/or a culture liquid containing the enzyme obtained by culturing the cell, may be allowed to act on the compound. The cell having an ability to produce the enzyme is preferably a cell transformed with DNA encoding the enzyme. The cell may be a microorganism (host organism), cultured cell, or the like, and may be either a living cell or a dead cell. For example, a resting microorganism may also be favorably used.

Examples of the processed product of the cell include treated products of the cell, such as the cell treated with an organic solvent, for example, acetone, dimethylsulfoxide (DMSO), or toluene, the cell treated with a surfactant, the cell treated by freeze drying, and the cell mechanically or enzymatically homogenized; crude purified products or purified products of an enzyme fraction extracted from the cell; and carriers such as polyacrylamide gel and carrageenan gel on which these products are immobilized.

As the culture liquid obtained by culturing the cell, a culture liquid obtained by culturing the cell, that is, a culture liquid containing the enzyme, may be directly used. Alternatively, for example, a suspension of the cell in a liquid medium may be used, or, in cases where the cell is of a secretory expression type, a supernatant obtained after removal of the cell by centrifugation or the like, or a concentrated product thereof, may be used.

Examples of the DNA encoding the enzyme to be used for the transformation or the like herein include DNAs encoding a protein comprising the amino acid sequence of SEQ ID NO: 4, 6, 8, 10, 12, 14, 16, or 18. Alternatively, the DNA may be a DNA encoding a protein comprising an amino acid sequence with a homology of not less than 35%, preferably not less than 50%, more preferably not less than 80%, especially preferably not less than 95%, most preferably not less than 98% to the amino acid sequence of SEQ ID NO: 4, 6, 8, 10, 12, 14, 16, or 18, and having an enzyme activity to convert a compound represented by General Formula (2) to a compound represented by the General Formula (3).

Examples of the DNA encoding an enzyme comprising the amino acid sequence of SEQ ID NO: 4, 6, 8, 10, 12, 14, 16, or 18 include DNAs comprising the nucleotide sequence of SEQ ID NO: 3, 5, 7, 9, 11, 13, 15, or 17, respectively. The DNA may be a homologue of the nucleotide sequence of SEQ ID NO: 3, 5, 7, 9, 11, 13, 15, or 17, as long as the DNA encodes a protein having an activity to hydrolyze an ester group. That is, examples of the DNA encoding the enzyme include the following.

(D) A DNA comprising the nucleotide sequence of SEQ ID NO: 3, 5, 7, 9, 11, 13, 15, or 17.

(E) A DNA comprising the nucleotide sequence of SEQ ID NO: 3, 5, 7, 9, 11, 13, 15, or 17 in which one or several bases are substituted, deleted, and/or added, and encoding a polypeptide having an enzyme activity to convert a compound represented by the General Formula (2) to a compound represented by the General Formula (3).

(F) A DNA comprising the nucleotide sequence of SEQ ID NO: 3, 5, 7, 9, 11, 13, 15, or 17; or a DNA comprising a nucleotide sequence which hybridizes with the complementary strand thereof under stringent conditions, and encoding a polypeptide having an enzyme activity to convert a compound represented by the General Formula (2) to a compound represented by the General Formula (3).

The nucleotide sequences of SEQ ID NOs: 3, 5, 7, 9, 11, 13, 15, and 17 are cDNA sequences.

More specifically, in the DNA of (E), the term "several" means not more than 60, preferably not more than 30, more preferably not more than 10, most preferably not more than 5.

In the DNA of (F), the "DNA which hybridizes under stringent conditions" means a DNA obtained by carrying out colony hybridization, plaque hybridization, Southern blot hybridization, or the like using a probe DNA under stringent conditions. Examples of the "stringent conditions" include conditions for colony hybridization and plaque hybridization wherein hybridization is carried out in the presence of 0.7 mol/L to 1.0 mol/L sodium chloride at 65° C. using a filter on which colony-derived or plaque-derived DNAs or fragments of the DNAs are immobilized, and the resulting filter is then washed using 0.1 to 2×SSC solution (composition of 1×SSC: 150 mmol/L sodium chloride and 15 mmol/L sodium citrate) at 65° C.

The DNA encoding an enzyme having an activity to hydrolyze an ester group can be isolated by, for example, the following method. First, an enzyme having an activity to hydrolyze an ester group is purified from microorganism cells or the like by the above-described method or the like, and the amino acid sequence at the N-terminus of the enzyme is analyzed. The analysis of the amino acid sequence at the N-terminus is carried out by cleaving the purified protein with enzymes such as lysyl endopeptidase, V8 protease, and/or the like, purifying the resulting peptide fragments by reversed-phase liquid chromatography and/or the like, and then determining a plurality of amino acid sequences by amino acid sequence analysis using a protein sequencer. By performing PCR using primers designed based on the amino acid sequences determined, and chromosomal DNA or a cDNA library of a microorganism strain that produces the enzyme as a template, a part of DNA (DNA fragment) encoding the enzyme can be obtained. A restriction enzyme digest of chromosomal DNA of a microorganism strain that produces the enzyme is introduced into a phage, plasmid, or the like, and E. coli is transformed with the resulting phage, plasmid, or the like to obtain a library or a cDNA library. By carrying out colony hybridization, plaque hybridization, or the like against the resulting library or cDNA library using the DNA fragment as a probe, a DNA encoding the enzyme having an activity to hydrolyze an ester group can be obtained.

It is also possible to obtain the DNA encoding the enzyme by analyzing the nucleotide sequence of the DNA fragment obtained by the PCR, designing, based on the sequence obtained, a PCR primer for extension of the sequence to the outside of the region whose sequence was determined, digesting chromosomal DNA of a microorganism strain which produces the enzyme with an appropriate restriction enzyme, and then performing inverse PCR (Genetics vol. 120, p 621-623 (1988)) using DNA cyclized by self-cyclization as a template. The DNA comprising the sequence of SEQ ID NO: 3, 5, 7, 9, 11, 13, 15, or 17 herein can be obtained by PCR using primers designed based on the nucleotide sequence of SEQ ID NO: 3, 5, 7, 9, 11, 13, 15, or 17, respectively.

The DNA encoding the enzyme can also be obtained by chemical synthesis of DNA having the nucleotide sequence of SEQ ID NO: 3, 5, 7, 9, 11, 13, 15, or 17.

Those skilled in the art can obtain the DNA encoding the enzyme having an activity to hydrolyze an ester group which can be used in the production method of the present invention, by introducing, if necessary, a substitution, deletion, insertion, and/or addition mutation(s) to the DNA of SEQ ID NO: 3, 5, 7, 9, 11, 13, 15, or 17 by site-directed mutagenesis (Adv. Biochem. Eng. vol. 43, p 75-102 (1990); Yeast vol., Molecular Cloning 2nd Edt., Cold Spring Harbor Laboratory Press (1989); PCR: A Practical Approach, IRL Press, p 200 (1991)) or the like.

Alternatively, based on the whole or part of the amino acid sequence of SEQ ID NO: 4, 6, 8, 10, 12, 14, 16, or 18, or the whole or part of the nucleotide sequence of SEQ ID NO: 3, 5, 7, 9, 11, 13, 15, or 17, homology search may be carried out against a database such as GenBank or DDBJ to obtain nucleotide sequence information on a DNA homolog encoding an enzyme having an activity to hydrolyze an ester group. Those skilled in the art can obtain DNA encoding the enzyme by PCR or the like from a strain based on the nucleotide sequence information.

The DNA encoding an enzyme having an activity to hydrolyze an ester group can also be obtained by carrying out colony hybridization, plaque hybridization, Southern blot hybridization, or the like using a DNA having the whole or part of the nucleotide sequence of SEQ ID NO: 3, 5, 7, 9, 11, 13, 15, or 17 as a probe under stringent conditions against DNA prepared from an arbitrary microorganism having the enzyme activity, and obtaining a hybridizing DNA. The "part" herein means a DNA having a length sufficient for use as a probe. More specifically, the length of the DNA is not less than 15 bp, preferably not less than 50 bp, more preferably not less than 100 bp.

Each hybridization can be carried out according to the method described in Chapter 1 of Molecular Cloning 3rd Edt. (Cold Spring Harbor Laboratory Press, 2001)).

By inserting the thus isolated DNA encoding an enzyme having an activity to hydrolyze an ester group into a known expression vector in a manner which allows expression of the enzyme, an expression vector for the enzyme having an activity to hydrolyze an ester group can be provided. By culturing cells transformed with this expression vector, the enzyme can be obtained from the cells. Transformed cells can also be obtained by incorporating the DNA encoding an enzyme having an activity to hydrolyze an ester group into chromosomal DNA of known host cells in a manner which allows expression of the enzyme.

More specifically, the preparation of the transformed cells needs to be carried out by incorporating the DNA encoding an enzyme having an activity to hydrolyze an ester group into a plasmid vector or a phage vector capable of being stably present in a microorganism, and introducing the constructed expression vector into the microorganism, or by directly introducing the DNA encoding the enzyme into the genome of a host organism, and allowing transcription and translation of the genetic information.

In cases where the DNA encoding the enzyme does not contain a promoter which allows expression in the host microorganism, an appropriate promoter needs to be incorporated in the 5'-upstream in the DNA strand where the enzyme is encoded. In addition, a terminator is preferably incorporated in the 3'-downstream. The promoter and the terminator are not limited as long as these are a promoter and a terminator which are known to function in the microorganism used as the host. Vectors, promoters, and terminators which can be used for the various microorganisms are described in detail in, for example, "Fundamental Microbiology, Vol. 8, Genetic Engineering, Kyoritsu Shuppan Co., Ltd."; and, especially for cases of yeasts, Adv. Biochem. Eng. vol. 43, p 75-102 (1990); and Yeast vol. 8, p 423-488 (1992).

The host organism to be transformed for expression of the enzyme having an activity to hydrolyze an ester group of the present invention is not limited as long as the host organism does not adversely affect the reaction. Specific examples of the host organism include the following microorganisms.

Bacteria belonging to the genera *Escherichia, Bacillus, Pseudomonas, Serratia, Brevibacterium, Corynebacterium, Streptococcus, Lactobacillus*, and the like whose host-vector systems are established.

Actinomycetes belonging to the genera *Rhodococcus, Streptomyces*, and the like whose host-vector systems are established.

Yeasts belonging to the genera *Saccharomyces, Kluyveromyces, Schizosaccharomyces, Zygosaccharomyces, Yarrowia, Trichosporon, Rhodosporidium, Hansenula, Pichia, Candida*, and the like whose host-vector systems are established.

Molds belonging to the genera *Neurospora, Aspergillus, Cephalosporium, Trichoderma*, and the like whose host-vector systems are established.

Among these, the genera *Escherichia, Bacillus, Brevibacterium*, and *Corynebacterium* are preferred, and the genera *Escherichia* and *Corynebacterium* are especially preferred as the host microorganism.

The procedure for the preparation of the transformed cells, the construction of the recombinant vector suitable for the host organism, and the method for culturing the host can be carried out according to techniques conventionally used in the fields of molecular biology, bioengineering, and genetic engineering (see, for example, Molecular Cloning 3rd Edt. (Cold Spring Harbor Laboratory Press, 2001)).

Various host-vector systems have been established in plants and animals, in addition to microorganisms. In particular, systems that allow expression of a large amount of a heterogeneous protein in cells of an animal such as an insect (e.g., silkworm) (Nature vol. 315, p 592-594 (1985)), or cells of a plant such as rapeseed, maize, or potato; and systems using a cell-free protein synthesis system based on a cell-free extract from *E. coli*, wheat germ, or the like; have been established, and may be preferably used.

Specific examples of the enzyme having an activity to hydrolyze an ester group include *Bacillus licheniformis*-derived protease (manufactured by Sigma-Aldrich), *Bacillus subtilis*-derived carboxyesterase NP (SEQ ID NO: 4, 6, 8, 10, 12, 14, 16, or 18), *Bacillus stearothermophilus*-derived esterase BS1 (manufactured by Julich Fine Chemicals), *Bacillus stearothermophilus*-derived esterase BS3 (manufactured by Julich Fine Chemicals), and pig liver-derived esterase (manufactured by Sigma-Aldrich), and these may be appropriately selected depending on the purpose.

Among these, in cases where a chiral compound selectively containing an (S)-isomer compound represented by General Formula (3S) is to be obtained, *Bacillus licheniformis*-derived protease (manufactured by Sigma-Aldrich) and *Bacillus subtilis*-derived carboxyesterase NP are preferred as the enzyme.

The optical purity of the compound represented by General Formula (3S) obtained in this case is generally not less than 90.0% e.e., but, since high optical purity is generally required in cases where the compound is produced as a pharmaceutical or an intermediate therefor, the optical purity is preferably not less than 95.0% e.e., more preferably not less than 99.0% e.e., especially preferably not less than 99.5% e.e., most preferably not less than 99.8% e.e.

In cases where a chiral compound selectively containing an (R)-isomer compound represented by General Formula (3R) is to be obtained, *Bacillus stearothermophilus*-derived esterase BS1 (manufactured by Julich Fine Chemicals), *Bacillus stearothermophilus*-derived esterase BS3 (manufactured by Julich Fine Chemicals), or pig liver-derived esterase (manufactured by Sigma-Aldrich) is preferably used as the enzyme. *Bacillus stearothermophilus*-derived esterase BS1 (manufactured by Julich Fine Chemicals), *Bacillus stearothermophilus*-derived esterase BS3 (manufactured by Julich Fine Chemicals), and the like are preferred.

The optical purity of the compound represented by General Formula (3R) obtained in this case is generally not less than 90.0% e.e., but, since high optical purity is generally required in cases where the compound is produced as a pharmaceutical or an intermediate therefor, the optical purity is preferably not less than 95.0% e.e., more preferably not less than 99.0% e.e., especially preferably not less than 99.5% e.e., most preferably not less than 99.8% e.e.

In cases where the hydrolysis is carried out by action of an enzyme, a cell having an ability to produce the enzyme, a processed product of the cell, and/or a culture liquid containing the enzyme obtained by culturing the cell, the hydrolysis is usually carried out in an aqueous solvent. However, the hydrolysis may also be carried out in the presence of at least one organic solvent.

In cases where an organic solvent is used, examples of the organic solvent which may be used include alcohols such as glycerol, ethylene glycol, methanol, ethanol, 1-propanol, and 2-propanol; ketones such as acetone, 2-butanone, and methylisobutyl ketone; ethers such as diethyl ether, di-n-propyl ether, diisopropyl ether, di-n-butyl ether, methyl isopropyl ether, methyl-tert-butyl ether, ethyl-tert-butyl ether, cyclopentyl methyl ether, tetrahydrofuran, dioxane, and 1,2-dimethoxyethane; aliphatic hydrocarbons such as n-pentane, n-hexane, and n-heptane; esters such as ethyl acetate, isopropyl acetate, and butyl acetate; aromatic hydrocarbons such as benzene, toluene, and xylene; nitriles such as acetonitrile and propionitrile; halogenated hydrocarbons such as dichloromethane, chloroform, carbon tetrachloride, and 1,2-dichloroethane; dimethylsulfoxide; and dimethylformamide. Preferably, from the viewpoint of organic solvent tolerance of the enzyme, use of an organic solvent is avoided, and only water is used.

The reaction temperature may be selected within the range of, for example, 0° C. to 80° C. From the viewpoint of thermal stability of the enzyme, the reaction temperature is preferably 20° C. to 50° C.

The reaction time may be appropriately selected within the range of, for example, 1 hour to 120 hours. The reaction time is preferably 2 hours to 40 hours since, in cases where the reaction time is long, the yield tends to decrease due to hydrolysis of the ester group in the compound represented by General Formula (3).

A pH suitable for the reaction may be appropriately selected depending on the enzyme used and the like. For example, the pH is 2.0 to 12.0. The pH is preferably 6.0 to 11.0, more preferably 7.0 to 9.0. Such a pH is selected for prevention of hydrolysis in which the enzyme is not involved. In the hydrolysis in which the enzyme is not involved, the ester group in the compound represented by General Formula (3) may undergo hydrolysis after the reaction of interest, leading to a decrease in the yield; or a compound represented by General Formula (3R) may be unexpectedly produced in the reaction to obtain a compound represented by General Formula (3S), or a compound represented by General Formula (3S) may be unexpectedly produced in the reaction to obtain a compound represented by General Formula (3R), leading to a decrease in the purity. Thus, the reaction is preferably carried out at a pH at which these phenomena can be suppressed.

Also in cases where the enzyme and/or the like of the present invention is allowed to act, an acid or a base may be added in order to adjust the pH within a preferred range.

(Post-Treatment)

After the reaction, if necessary, post-treatment may be carried out by, for example, inactivation of the microorganism, centrifugation, coagulant treatment, filtration, extraction, concentration, and/or purification on a column. In cases where extraction is carried out, an acid may be added to the reaction solution to release the compound of General Formula (3) as a carboxylic acid, and extraction using a water-insoluble organic solvent may be performed. In cases where the purity of the compound represented by General Formula (3) is sufficiently high even without purification, it is preferred to carry out only filtration, extraction, and concentration without carrying out purification, from the viewpoint of simplicity. More preferably, in cases where extraction is carried out, the extraction is carried out with the reaction solvent used in the subsequent step, and only filtration and the extraction are carried out.

Examples of the water-insoluble organic solvent used in the extraction include ketones such as 2-butanone, methylisobutyl ketone, and cyclohexanone; aromatic hydrocarbons such as benzene, toluene, xylene, chlorobenzene, and trifluoromethylbenzene; aliphatic hydrocarbons such as n-pentane, n-hexane, n-heptane, and cyclohexane; esters such as methyl acetate, ethyl acetate, isopropyl acetate, and butyl acetate; ethers such as diethyl ether, di-n-propyl ether, diisopropyl ether, di-n-butyl ether, methyl-tert-butyl ether, ethyl-tert-butyl ether, and cyclopentyl methyl ether; and halogenated hydrocarbons such as dichloromethane, chloroform, carbon tetrachloride, and 1,2-dichloroethane. Two or more of these may be used as a mixed solvent.

Among these, from the viewpoint of extraction efficiency, aromatic hydrocarbons and esters are preferred. Use of benzene, toluene, methyl acetate, ethyl acetate, isopropyl acetate, butyl acetate, or a mixed solvent of two or more of these is more preferred. Use of toluene is still more preferred since toluene has high tolerance to acidic conditions, and can be reused.

<Step (ii)>

The step (ii) is described below.

The step (ii) is a step of allowing a condensing agent or an acid halogenating agent to act on a compound represented by General Formula (3):

(wherein $R^1$ represents a $C_1$-$C_{10}$ alkyl group which is optionally substituted, a $C_7$-$C_{20}$aralkyl group which is optionally substituted, or a $C_6$-$C_{12}$ aryl group which is optionally substituted, and $R^2$ represents a $C_1$-$C_4$ alkyl group), to obtain a compound represented by General Formula (4)

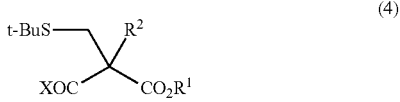

(wherein $R^1$ and $R^2$ have the same meanings as $R^1$ and $R^2$ in the General Formula (3); X represents —OP(O)(OPh)$_2$, —OP(O)(OEt)$_2$, —OC(O)OR$^3$, or a halogen atom; and $R^3$ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted).

The $R^1$ and the $R^2$ in the compounds represented by the General Formulae (3) and (4) are the same as those described in the step (i).

The compound represented by the General Formula (4) may be either a racemic compound or a chiral compound. Since high optical purity is generally required in cases where the compound is produced as a pharmaceutical or an intermediate therefor, the compound is preferably a chiral compound having high optical purity. The optical purity is preferably not less than 95.0% e.e., more preferably not less than 99.0% e.e., especially preferably not less than 99.5% e.e., most preferably not less than 99.8% e.e.

Examples of X in General Formula (4) include a —OP(O)(OPh)$_2$ group, —OP(O)(OEt)$_2$ group, —OC(O)OR$^3$ group (wherein $R^3$ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted), and a halogen atom. Among these, compounds represented by General Formula (4-1):

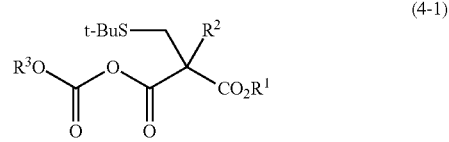

(wherein $R^1$, $R^2$, and $R^3$ have the same meanings as $R^1$, $R^2$, and $R^3$ in the General Formula (4)), wherein X represents —OC(O)OR³, are preferred since they are stable against water and can be easily handled in the later-described step (iii).

Examples of the alkyl group of the "C₁-C₁₀ alkyl group which is optionally substituted" as R³ include C₁-C₁₀ linear, branched, or cyclic alkyl groups such as methyl, ethyl, isopropyl, n-propyl, n-butyl, isobutyl, sec-butyl, tert-butyl, n-pentyl, isopentyl, tert-pentyl, neopentyl, n-hexyl, cyclopropyl, cyclobutyl, cyclopentyl, and cyclohexyl. Examples of the substituent optionally contained in the alkyl group include C₁-C₆ alkoxy groups such as methoxy and ethoxy; halogen atoms such as a fluorine atom, chlorine atom, bromine atom, and iodine atom; and nitro. The number of substituents is not limited, and, in cases where there are two or more substituents in the alkyl group, the substituents may be of the same type or different types.

Examples of the aralkyl group of the "C₇-C₂₀ aralkyl group which is optionally substituted" as R³ include benzyl, 2-phenylethyl, 1-phenylethyl, 1-phenylpropyl, 2-phenylpropyl, and 3-phenylpropyl. Examples of the substituent optionally contained in the aralkyl group include C₁-C₆ alkyl groups such as methyl, ethyl, and isopropyl; C₁-C₆ alkoxy groups such as methoxy and ethoxy; halogen atoms such as a fluorine atom, chlorine atom, bromine atom, and iodine atom; and nitro. The number of substituents is not limited, and, in cases where there are two or more substituents in the aralkyl group, the substituents may be of the same type or different types.

Examples of the aryl group of the "C₆-C₁₂ aryl group which is optionally substituted" as R³ include phenyl, 1-naphthyl, and 2-naphthyl. Examples of the substituent optionally contained in the aryl group include C₁-C₆ alkyl groups such as methyl, ethyl, and isopropyl; C₁-C₆ alkoxy groups such as methoxy and ethoxy; halogen atoms such as a fluorine atom, chlorine atom, bromine atom, and iodine atom; and nitro. The number of substituents is not limited, and, in cases where there are two or more substituents in the aryl group, the substituents may be of the same type or different types.

For each type of X in the General Formula (4), preferred condensing agents or acid halogenating agents, and preferred structures of X are described below.

In cases where a compound represented by the General Formula (4) in which X is —OP(O)(OPh)₂, that is, a compound represented by the General Formula (4-1), is to be obtained, diphenylphosphoryl azide may be used as a condensing agent.

In cases where a compound represented by the General Formula (4) in which X is —OP(O)(OEt)₂ is to be obtained, diethylphosphoryl azide may be used as a condensing agent.

In cases where a compound represented by the General Formula (4) in which X is —OC(O)OR³ is to be obtained, a chloroformic ester represented as ClC(O)OR³ may be used as a condensing agent or an acid halogenating agent. Preferred examples of easily available chloroformic esters include C₁-C₆ linear or branched chloroformic esters such as methyl chloroformate, ethyl chloroformate, n-propyl chloroformate, isopropyl chloroformate, n-butyl chloroformate, isobutyl chloroformate, and tert-butyl chloroformate; phenyl chloroformate; and benzyl chloroformate.

In the cases where X is —OC(O)OR³, R³ is preferably a C₁-C₆ linear or branched alkyl group such as methyl, ethyl, n-propyl, isopropyl, n-butyl, isobutyl, or tert-butyl; phenyl; or benzyl; from the viewpoint of availability as the chloroformic ester.

The structure of R³ also influences the later-described step (iii). As a mixed acid anhydride, the compound represented by the General Formula (4-1) has both a carbonyl group derived from a substrate malonic acid derivative and a carbonyl group derived from a condensing agent. The reaction in the step (iii) begins by nucleophilic attack by an azide anion. In cases where the nucleophilic attack does not occur selectively to the carbonyl group of interest derived from the malonic acid derivative, the yield of the compound represented by General Formula (5):

(wherein R¹ and R² have the same meanings as R¹ and R² in the General Formula (4)) tends to decrease. Normally, considering the electron density of the two carbonyl groups, the nucleophilic attack of interest occurs. However, since the compound represented by General Formula (4-1) is a disubstituted malonic acid derivative, the extent of steric hindrance in the vicinity of the carbonyl group derived from the malonic acid derivative is large. Therefore, the nucleophilic attack of interest may be unlikely to occur selectively especially in cases where the structure of R³ in the compound represented by General Formula (4-1) is small.

Thus, R³ is more preferably ethyl, n-propyl, isopropyl, n-butyl, isobutyl, tert-butyl, phenyl, or benzyl. As the chloroformic ester corresponding thereto, ethyl chloroformate, n-propyl chloroformate, isopropyl chloroformate, n-butyl chloroformate, isobutyl chloroformate, tert-butyl chloroformate, phenyl chloroformate, or benzyl chloroformate is preferred. In the later-described step (iii), the alcohol represented by R³OH is produced as a by-product, and the by-produced alcohol needs to be removed by washing with water or concentration. Considering ease of the removal of the alcohol, R³ is still more preferably ethyl or isopropyl. The chloroformic esters corresponding to these are ethyl chloroformate and isopropyl chloroformate.

Thus, specific examples of the compound represented by the General Formula (4-1) include the following compounds.

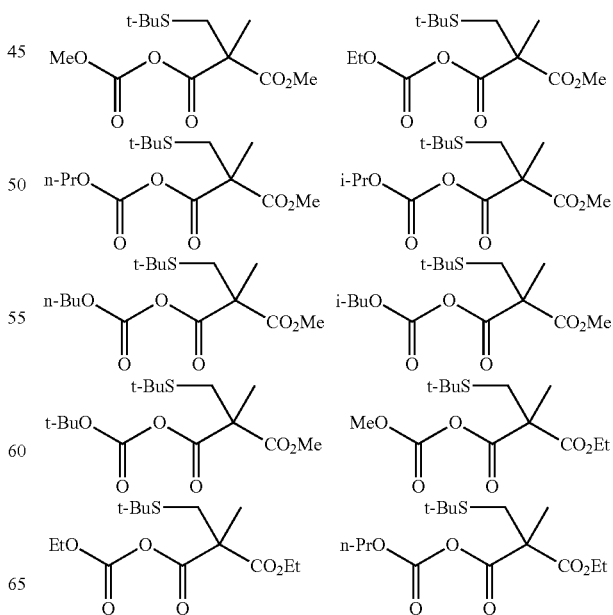

-continued

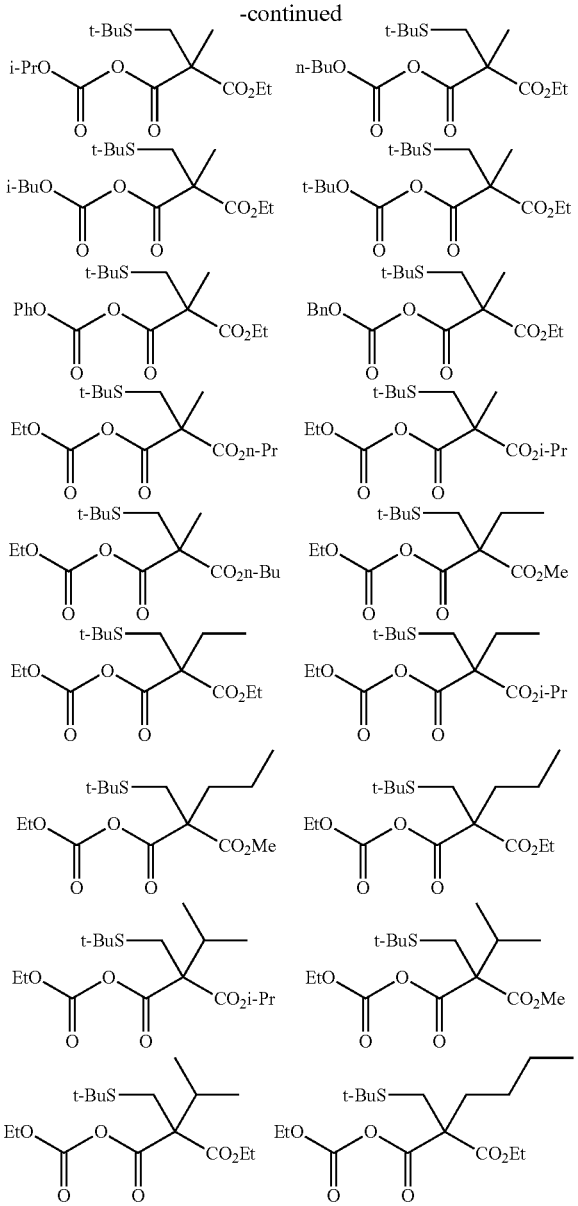

Among the compounds mentioned above, the following compounds are preferred as the compound represented by the General Formula (4-1).

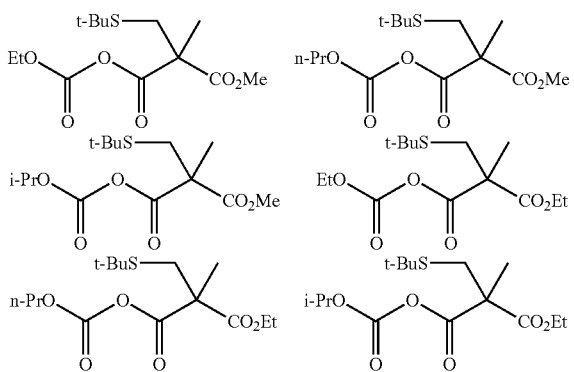

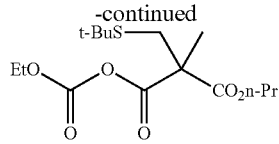

In cases where a compound represented by the General Formula (4) in which X is a halogen atom is to be obtained, an acid halogenating agent may be used in the step (ii).

Examples of the halogen atom herein include a chlorine atom, bromine atom, and iodine atom. From the viewpoint of stability of the compound, a chloride atom is preferred.

Examples of the acid halogenating agent include thionyl chloride, sulfuryl chloride, thionyl bromide, phosphorous trichloride, phosphorous pentachloride, phosphorous oxytrichloride, phosphorus tribromide, phosphorus pentabromide, phosphorous oxytribromide, oxalyl chloride, oxalyl bromide, phosgene, triphosgene, and cyanuric chloride. In particular, since X is preferably a chlorine atom as described above, thionyl chloride, sulfuryl chloride, phosphorous trichloride, phosphorous pentachloride, phosphorous oxytrichloride, oxalyl chloride, phosgene, triphosgene, and cyanuric chloride are preferred. Thionyl chloride, sulfuryl chloride, and oxalyl chloride are more preferred because of their low toxicity.

The conditions for the reaction with the condensing agent or the acid halogenating agent vary depending on, for example, the type of X in the General Formula (4) and the structure of $R^3$, and may therefore be appropriately set. For example, the reaction may be carried out under the following reaction conditions.

Normally, the amount of the condensing agent or the acid halogenating agent may be appropriately set within the range of 0.7 molar equivalent to 10 molar equivalents with respect to the amount of the compound represented by General Formula (3). In order to allow complete disappearance of the material and to increase the yield, the amount is preferably 1.0 molar equivalent to 5.0 molar equivalents. From the viewpoint of reducing the purification load, the amount is more preferably 1.0 molar equivalent to 1.5 molar equivalents.

A base may be used in the reaction by the condensing agent or the acid halogenating agent. The base is not limited as long as the base does not have nucleophilicity, and tertiary amines and pyridines are preferred as the base.

Examples of the tertiary amines include trimethylamine, triethylamine, triisopropylamine, tripropylamine, triisobutylamine, N,N-dimethylethylamine, N,N-dimethylisopropylamine, N-butyldimethylamine, N,N-diisopropylethylamine, N,N-dimethylcyclohexylamine, and N-methylmorpholine.

Examples of the pyridines include pyridine, 2-chloropyridine, 3-chloropyridine, 2-methylpyridine, 3-methylpyridine, 2,3-lutidine, 2,4-lutidine, 2,5-lutidine, 2,6-lutidine, 3,4-lutidine, and 3,5-lutidine.

Among the bases described above, the tertiary amines are preferred. This is because the salt produced by neutralization of the compound represented by General Formula (4) by the base is easily soluble in organic solvents, and the reaction can be allowed to proceed smoothly as a result. Triethylamine is more preferred among the tertiary amines since it is inexpensive.

The amount of the base used may be appropriately set within the range of, for example, 0.7 molar equivalent to 10 molar equivalents with respect to the amount of the compound represented by General Formula (3). From the viewpoint of allowing complete disappearance of the material and increasing the yield, the amount is preferably 1.0 molar equivalent to 5.0 molar equivalents. From the viewpoint of reduction of the purification load, the amount is more preferably 1.0 molar equivalent to 1.5 molar equivalents. From the viewpoint of suppression of production of by-products, the base is still more preferably used in the same amount as that of the condensing agent or the acid halogenating agent in terms of molar equivalence.

Examples of the reaction solvent used for the reaction by the condensing agent or the acid halogenating agent include ketones such as acetone, 2-butanone, methylisobutyl ketone, and cyclohexanone; aromatic hydrocarbons such as benzene, toluene, xylene, chlorobenzene, and trifluoromethylbenzene; aliphatic hydrocarbons such as n-pentane, n-hexane, n-heptane, and cyclohexane; esters such as methyl acetate, ethyl acetate, isopropyl acetate, and butyl acetate; ethers such as diethyl ether, di-n-propyl ether, diisopropyl ether, di-n-butyl ether, methyl isopropyl ether, methyl-tert-butyl ether, ethyl-tert-butyl ether, cyclopentyl methyl ether, tetrahydrofuran, dioxane, and 1,2-dimethoxyethane; amides such as N,N-dimethylformamide and N,N-dimethylacetamide; nitriles such as acetonitrile and propionitrile; halogenated hydrocarbons such as dichloromethane, chloroform, carbon tetrachloride, and 1,2-dichloroethane; and dimethylsulfoxide.

Among these, acetone, toluene, xylene, ethyl acetate, isopropyl acetate, tetrahydrofuran, dioxane, N,N-dimethylformamide, N,N-dimethylacetamide, acetonitrile, and propionitrile are preferred since the salt produced by neutralization of the compound represented by the General Formula (4) by the base is highly soluble in these solvents, and high reaction efficiency can be achieved. Acetone, toluene, xylene, ethyl acetate, isopropyl acetate, and tetrahydrofuran are more preferred from the viewpoints of their inexpensiveness and availability, and of simplification of the process since these do not adversely affect the subsequent step (iii) even without post-treatment. In cases where a polar solvent such as water or an alcohol is used, reaction tends to occur with the condensing agent or the acid halogenating agent, or the compound represented by the General Formula (4), leading to a decrease in the yield.

The amount of the reaction solvent used may be appropriately set within the range of, for example, 0 volume to 100 volumes with respect to the amount of the compound represented by the General Formula (3). The amount of the reaction solvent is preferably 1 volume to 20 volumes from the viewpoint of heat generation control and the volume efficiency, more preferably 4 volumes to 10 volumes from the viewpoint of the stirring efficiency.

The this step can be carried out by appropriately mixing the compound represented by the General Formula (3), the base, and the condensing agent or the acid halogenating agent together. From the viewpoint of the yield, the compound represented by the General Formula (3) and the base are preferably mixed together in advance.

The reaction temperature may be appropriately set. For example, the reaction temperature may be appropriately set within the range of −100° C. to 100° C. For allowing easy control of the temperature, ultralow temperature conditions are preferably avoided. On the other hand, since the compound represented by the General Formula (4) is unstable at high temperature, the reaction temperature is preferably −50° C. to 50° C., more preferably −10° C. to 30° C.

The reaction time may be appropriately set within the range of, for example, 5 minutes to 10 hours. Since, in general, the reaction becomes complete in a short time after the mixing, the reaction time is preferably 5 minutes to 5 hours, more preferably 15 minutes to 2 hours.

If necessary, post-treatment may be carried out after this reaction. For example, precipitated salt may be removed by filtration; water and a water-insoluble organic solvent may be added to perform solvent extraction; and/or solvent extraction may be followed by removal of a solvent by concentration. In cases where the purity is insufficient, purification using a column may be carried out. However, since, even without post-treatment or purification, the step (iii) described later is hardly adversely affected, the reaction solution in the step (ii) is preferably used as it is in the step (iii) from the viewpoint of simplifying the process.

<Step (iii)>

The step (iii) is described below.

The step (iii) is a step in which an azidation agent is allowed to act on a compound represented by General Formula (4):

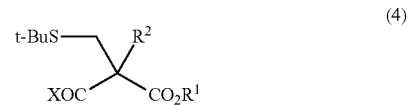

(4)

(wherein $R^1$ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted; $R^2$ represents a $C_1$-$C_4$ alkyl group; X represents —OP(O)(OPh)$_2$, —OP(O)(OEt)$_2$, —OC(O)OR$^3$, or a halogen atom; and $R^3$ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted), to obtain a compound represented by General Formula (5):

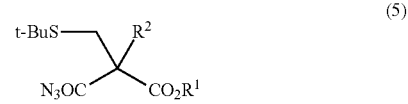

(5)

(wherein $R^1$ and $R^2$ have the same meanings as $R^1$ and $R^2$ in the General Formula (4)).

The $R^1$ and the $R^2$ in the compound represented by the General Formula (4) have the same meanings as those in the description for the step (ii).

The $R^1$ and the $R^2$ in the compound represented by the General Formula (5) have the same meanings as those in the descriptions for the step (i) and the step (ii).

Thus, specific examples of the compound represented by the General Formula (5) include the following compounds.

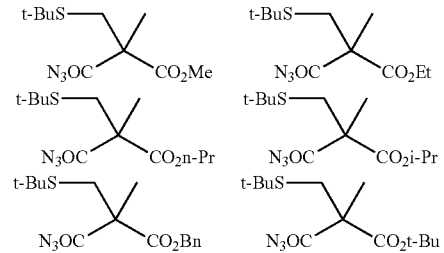

-continued

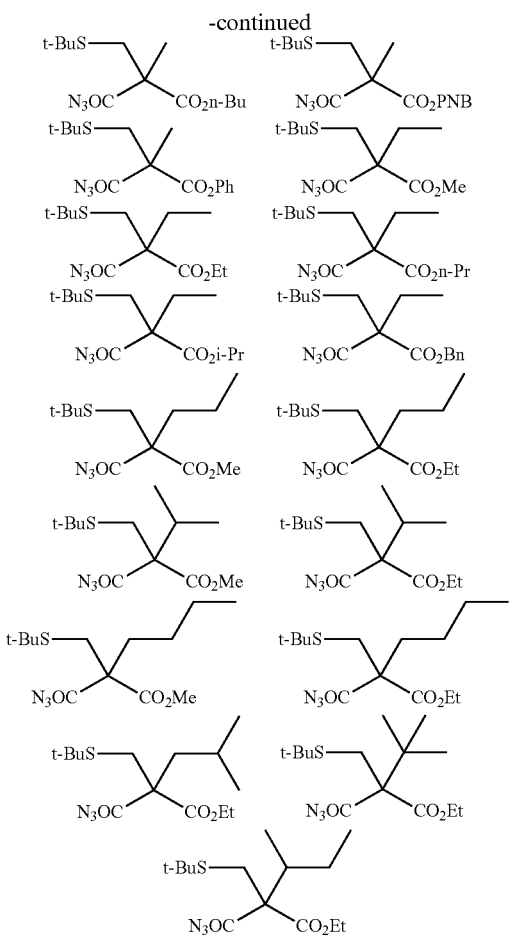

Among the compounds mentioned above, the following compounds are preferred as the compound represented by the General Formula (5).

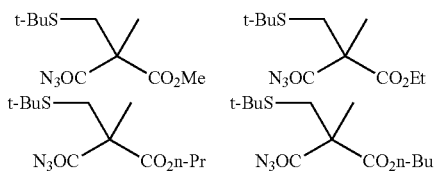

The compound represented by the General Formula (5) may be either a racemic compound or a chiral compound. Since high optical purity is generally required in cases where the compound is produced as a pharmaceutical or an intermediate therefor, the compound is preferably a chiral compound having high optical purity. The optical purity is preferably not less than 95.0% e.e., more preferably not less than 99.0% e.e., especially preferably not less than 99.5% e.e., most preferably not less than 99.8% e.e.

Examples of the azidation agent include metal azides such as sodium azide, potassium azide, and lithium azide; and trialkylsilyl azides such as trimethylsilyl azide. Since trialkylsilyl azides may produce trialkylsilanol as a by-product, and an operation for its separation from the compound represented by General Formula (5) may be necessary, metal azides are preferred. Among the metal azides, sodium azide is more preferred since it is easily available.

The amount of the azidation agent used may be appropriately set within the range of, for example, 0.7 molar equivalent to 10 molar equivalents with respect to the amount of the compound represented by General Formula (4). From the viewpoint of the yield and the cost, the amount is preferably 1.0 molar equivalent to 5.0 molar equivalents, more preferably 1.0 molar equivalent to 2.0 molar equivalents.

Examples of the reaction solvent include water; ketones such as acetone, 2-butanone, methylisobutyl ketone, and cyclohexanone; aromatic hydrocarbons such as benzene, toluene, xylene, chlorobenzene, and trifluoromethylbenzene; aliphatic hydrocarbons such as n-pentane, n-hexane, n-heptane, and cyclohexane; esters such as methyl acetate, ethyl acetate, isopropyl acetate, and butyl acetate; ethers such as diethyl ether, di-n-propyl ether, di-n-butyl ether, methyl isopropyl ether, methyl-tert-butyl ether, ethyl-tert-butyl ether, cyclopentyl methyl ether, tetrahydrofuran, dioxane, and 1,2-dimethoxyethane; amides such as N,N-dimethylformamide and N,N-dimethylacetamide; nitriles such as acetonitrile and propionitrile; halogenated hydrocarbons such as dichloromethane, chloroform, carbon tetrachloride, and 1,2-dichloroethane; and dimethylsulfoxide.

In cases where an alcohol is used as the reaction solvent, reaction with the compound represented by General Formula (4) may occur to decrease the yield. Among the reaction solvents described above, acetone, toluene, xylene, ethyl acetate, isopropyl acetate, and tetrahydrofuran are preferred from the viewpoints of the cost and availability, and of simplification of the process since the this step can be carried out continuously from the step (ii).

In particular, in cases where a metal azide is used as the azidation agent, and water is added to the solvent, the metal azide is dissolved in the water, and the reaction efficiently proceeds, which is more preferred. In particular, in cases where toluene or xylene is used in combination with water, the later-described post-treatment operations such as washing with water and extraction can be carried out without further addition of a solvent, which is still more preferred.

In cases where a metal azide is used as the azidation agent, and water is used as the solvent, the compound represented by the General Formula (4) to be used as the material for the reaction is preferably a compound which hardly undergoes degradation due to water. A compound represented by General Formula (4-1), in which the X is —OC(O)OR$^3$, is more preferably used.

The amount of the reaction solvent used may be appropriately set within the range of, for example, 0 volume to 100 volumes with respect to the amount of the compound represented by General Formula (4). The amount of the reaction solvent is preferably 1 volume to 20 volumes from the viewpoint of heat generation control and the volume efficiency, more preferably 5 volumes to 10 volumes from the viewpoint of ease of stirring.

The reaction temperature may be appropriately set within the range of, for example, −100° C. to 100° C. Since the temperature can be easily controlled at −30° C. to 50° C., ultralow temperature conditions are preferably avoided. Further, since the compound represented by General Formula (5) may cause a side reaction at a high temperature to decrease the yield, the reaction temperature is more preferably −10° C. to 20° C.

The reaction time may be appropriately set within the range of, for example, 5 minutes to 100 hours. Since the shelf stability of the compound represented by General Formula (5) is not high even at a low temperature, the reaction time is preferably 1 hour to 40 hours, more preferably 1 hour to 10 hours.

If necessary, post-treatment may be carried out after this reaction. For example, precipitated salt may be removed by filtration or washing with water, and/or water and a water-insoluble organic solvent may be added to perform extraction. In particular, in cases where an excessive amount of an azidation agent is used, it is sometimes risky to proceed to the next step without removal of the azidation agent, which is explosive. Therefore, as an operation for sufficient removal of the azidation agent to the outside of the reaction system, washing with water is preferably carried out using water and a water-insoluble solvent. In such a case, the step (iii) is more preferably carried out continuously, without further addition or substitution of a solvent, from the step (ii) which is carried out in a water-insoluble solvent such as toluene or xylene, since, in this case, the washing with water can be carried out without further addition of a water-insoluble solvent, which is advantageous from the economical viewpoint. Since, in general, acid azide compounds such as the compounds represented by General Formula (5) are explosive, removal of the solvent by distillation should be avoided.

In Non-patent Document 1, in the step (ii), triethylamine is used as the base, and diphenylphosphoryl azide is allowed to act as the condensing agent in 1,2-dichloroethane. That is, in Non-patent Document 1, a compound represented by General Formula (5) is obtained through a compound represented by General Formula (4) in which X is —OP(O)(OPh)$_2$, and the process of the step (ii) and the step (iii) is carried out in one step. The same applies to use of diethylphosphoryl azide instead of diphenylphosphoryl azide. However, in such a method, 1,2-dichloroethane, which is problematic in view of its toxicity and environmental load, is used as the solvent, and therefore the method is not suitable for industrial-scale production. Thus, in industrial-scale production, it is preferred to allow a chloroformic ester to act in the step (ii) using a halogen-free solvent to obtain a compound represented by General Formula (4), and then to allow a metal azide to act in the step (iii), in a stepwise manner as in the present invention. Since the combination of an alkyl chloroformate and a metal azide is less expensive than diphenylphosphoryl azide or diethylphosphoryl azide, the present method is preferred also from the viewpoint of the cost.

<Step (iv)>

The step (iv) is described below.

The step (iv) is a method for producing a compound represented by General Formula (6):

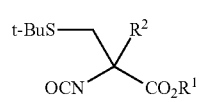

(6)

(wherein R$^1$ and R$^2$ have the same meanings as R$^1$ and R$^2$ in the General Formula (5) below),
which method comprises converting the azide group of a compound represented by General Formula (5):

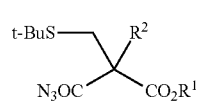

(5)

(wherein R$^1$ represents a C$_1$-C$_{10}$ alkyl group which is optionally substituted, a C$_7$-C$_{20}$ aralkyl group which is optionally substituted, or a C$_6$-C$_{12}$ aryl group which is optionally substituted, and R$^2$ represents a C$_1$-C$_4$ alkyl group) to an isocyanate group by Curtius rearrangement reaction, to obtain the compound represented by the General Formula (6).

R$^1$ and R$^2$ in the General Formulae (5) and (6) are the same as those described in the step (i).

Thus, specific examples of the compound represented by the General Formula (6) include the following compounds.

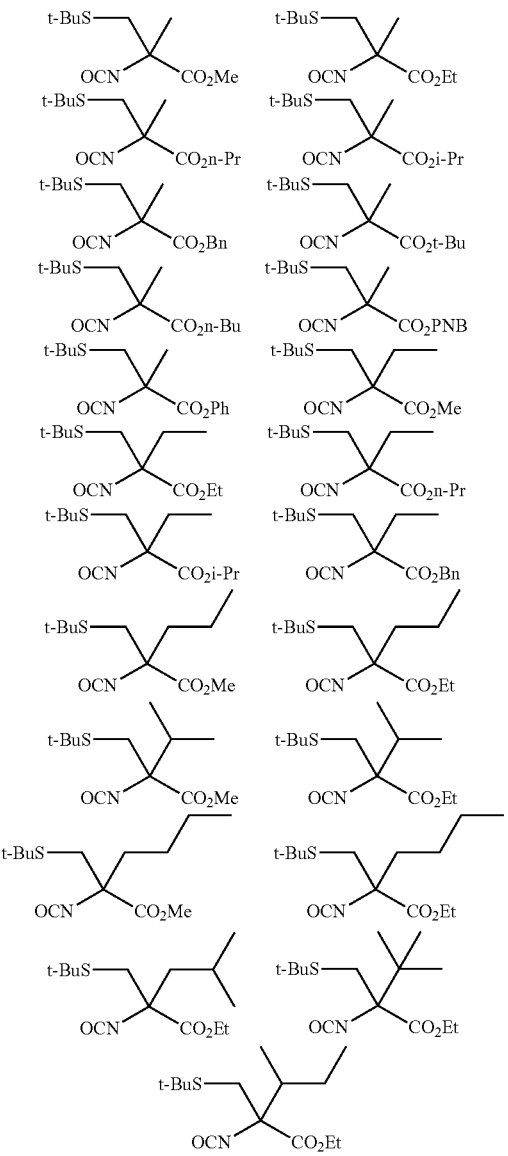

Among the compounds mentioned above, the following compounds are preferred as the compound represented by the General Formula (6).

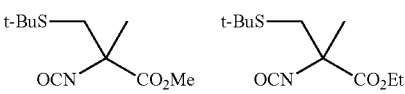

-continued

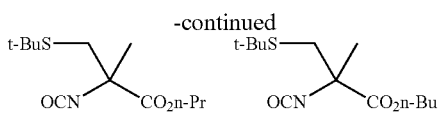

The compound represented by the General Formula (6) may be either a racemic compound or a chiral compound. Since high optical purity is generally required in cases where the compound is produced as a pharmaceutical or an intermediate therefor, the compound is preferably a chiral compound having high optical purity. The optical purity is preferably not less than 95.0% e.e., more preferably not less than 99.0% e.e., especially preferably not less than 99.5% e.e., most preferably not less than 99.8% e.e.

The Curtius rearrangement is a reaction in which the compound represented by General Formula (5), which is an acid azide compound, is heated to cause its conversion into an isocyanate compound, which is accompanied by elimination of the nitrogen molecule in the azide group. The reaction can be allowed to proceed without addition of a reagent.

Examples of organic solvents which may be used in this step include ketones such as acetone, 2-butanone, methylisobutyl ketone, and cyclohexanone; aromatic hydrocarbons such as benzene, toluene, xylene, chlorobenzene, and trifluoromethylbenzene; aliphatic hydrocarbons such as n-pentane, n-hexane, n-heptane, and cyclohexane; esters such as methyl acetate, ethyl acetate, and isopropyl acetate; ethers such as diethyl ether, di-n-propyl ether, di-n-butyl ether, methyl-tert-butyl ether, ethyl-tert-butyl ether, cyclopentyl methyl ether, tetrahydrofuran, dioxane, and 1,2-dimethoxyethane; amides such as N,N-dimethylformamide and N,N-dimethylacetamide; nitriles such as acetonitrile and propionitrile; halogenated hydrocarbons such as dichloromethane, chloroform, carbon tetrachloride, and 1,2-dichloroethane; and dimethylsulfoxide.

Among these, benzene, toluene, xylene, chlorobenzene, and trifluoromethylbenzene are preferred since they have high boiling points, and therefore the reaction rate can be increased by increasing the reaction temperature, so that the processing time can be shortened. Toluene and xylene are more preferred since they can be used continuously from the step (iii). That is, in cases where toluene or xylene is used, concentration and solvent replacement of the compound represented by General Formula (5), which is explosive, can be avoided, and moreover, their use is economically advantageous. Water and alcohols may react with the compound represented by General Formula (6) to produce, as a by-product, a dimer having a urea structure, or a carbamate, leading to a decrease in the yield.

The amount of the organic solvent used may be appropriately set within the range of, for example, 0 volume to 100 volumes with respect to the amount of the compound represented by General Formula (5). The amount of the organic solvent is preferably 3 volumes to 30 volumes from the viewpoint of heat generation control and the volume efficiency, more preferably 7 volumes to 15 volumes.

The reaction temperature may be appropriately set within the range of, for example, 0° C. to 300° C. From the viewpoint of reducing the reaction time and preventing degradation of the compound represented by General Formula (6), the reaction temperature is preferably 40° C. to 150° C., more preferably 70° C. to 110° C. In cases where the reaction temperature is higher than the temperature described above, the compound represented by General Formula (6) produced tends to be degraded, resulting in a low yield. On the other hand, in cases where the reaction temperature is lower than the temperature described above, the compound represented by General Formula (5) may accumulate in the reaction system without undergoing Curtius rearrangement, and the subsequent temperature increase may cause the reaction to proceed rapidly, resulting in generation of a large amount of nitrogen in a short time. Thus, from the viewpoint of safety, it is preferred, if necessary, to control the amount of nitrogen generated.

Since nitrogen is generated as the reaction proceeds in this step, the amount of nitrogen generated needs to be controlled from the viewpoint of safety, especially in industrial-scale production. Therefore, it is preferred to add the compound represented by General Formula (5) dropwise to a solvent warmed to a temperature at which Curtius rearrangement of the compound represented by General Formula (5) immediately occurs, and to control the amount of nitrogen generated based on the amount of the compound added dropwise.

From the viewpoint of the safety described in the previous section, the temperature is ideally set such that the reaction is completed immediately after the addition of the compound represented by General Formula (5). Practically, however, in order to complete the reaction, heating is preferably continued for 0 hour to 5 hours after the addition of the compound represented by General Formula (5). The heating is more preferably continued for 0 hour to 3 hours.

If necessary, post-treatment may be carried out after this reaction. For example, salt may be removed by filtration; water may be added to perform solvent extraction; and/or a solvent may be removed by concentration. Depending on the purity, purification using a column may be carried out. However, since the compound represented by General Formula (6) easily reacts with water to produce a dimer having a urea structure, post-treatment is preferably avoided.

In Non-patent Document 1, instead of carrying out the step (ii), reaction is performed under heat in 1,2-dichloroethane using triethylamine as the base and diphenylphosphoryl azide as the condensing agent. In such a method, a compound represented by General Formula (5) is obtained, but, practically, since the reaction is carried out under heat, the compound represented by General Formula (5) immediately undergoes Curtius rearrangement, and is converted into a compound represented by General Formula (6). That is, by the method described in Non-patent Document 1, the steps (ii), (iii), and (iv) can be obtained in one step, and the same applies to use of diethylphosphoryl azide instead of diphenylphosphoryl azide. However, in this method, diphenyl phosphate and diethyl phosphate are produced as by-products, so that an operation for removing these by-products is necessary. In Non-patent Document 1, purification is carried out by flash column chromatography. However, this operation is not suitable for industrial-scale production. As an alternative to this purification, washing with water may be possible. However, when the compound represented by General Formula (6) is brought into contact with water, a dimer having a urea structure is produced as a by-product as described above, and diphenyl phosphate and diethyl phosphate produced as by-products tend to cause side reactions with the compound represented by General Formula (6), resulting in a low yield.

Therefore, from the viewpoint of both quality and yield, the steps (ii) to (iv) are preferably carried out in a stepwise manner as described above such that, for example, a chloroformic ester is allowed to act to obtain a compound represented by General Formula (4) in the step (ii); a metal azide is allowed to act to obtain a compound represented by General Formula (5) in the step (iii); and the compound represented by General Formula (5) is converted to a compound represented by General Formula (6) by Curtius rearrangement in the step (iv).

After the steps (i) to (iv), the compound represented by General Formula (6) can be converted to an α-substituted cysteine represented by General Formula (1) or a salt thereof. The method for this conversion is not limited, and the conversion is preferably carried out by a method comprising the step (v) described below.

<Step (v)>

The step (v) is described below.

The step (v) is a step for obtaining an α-substituted cysteine represented by General Formula (1):

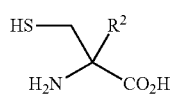

(1)

(wherein $R^2$ represents a $C_1$-$C_4$ alkyl group)
or a salt thereof, which step comprises the processes of:
(a) converting the isocyanate group in a compound represented by General Formula (6):

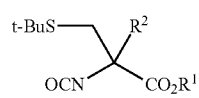

(6)

(wherein $R^1$ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ has the same meaning as in the General Formula (1)) to an amino group;
(b) hydrolyzing the ester group; and
(c) removing the tert-butyl group by action of an acid.

In the compounds represented by the General Formulae (1) and (6), the $R^1$ and the $R^2$ are the same as those described in the step (i).

Thus, specific examples of the α-substituted cysteine represented by the General Formula (1) include the following compounds.

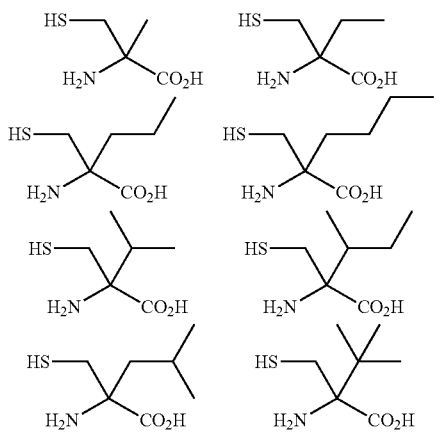

Among the compounds mentioned above, the following compounds are preferred as the α-substituted cysteine represented by the General Formula (1).

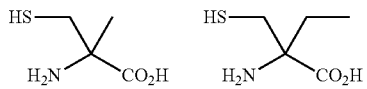

The α-substituted cysteine represented by General Formula (1) may be in the form of a salt. Examples of the salt of the α-substituted cysteine include inorganic acid salts such as hydrochloric acid salt, sulfuric acid salt, nitric acid salt, and phosphoric acid salt; carboxylic acid salts such as acetic acid salt, propionic acid salt, oxalic acid salt, malic acid salt, maleic acid salt, citric acid salt, succinic acid salt, tartaric acid salt, and mandelic acid salt; sulfonic acid salts such as methanesulfonic acid salt, p-toluenesulfonic acid salt, and camphorsulfonic acid salt; alkali metal salts such as sodium salt and potassium salt; alkaline earth metal salts such as calcium salt, magnesium salt, and barium salt; and organic amine salts such as ammonium salt, trimethylamine salt, triethylamine salt, phenethylamine salt, and pyridine salt. Among these, hydrochloric acid salt is preferred.

The compound represented by the General Formula (1) may be either a racemic compound or a chiral compound. Since high optical purity is generally required in cases where the compound is produced as a pharmaceutical or an intermediate therefor, the compound is preferably a chiral compound having high optical purity. The optical purity is preferably not less than 95.0% e.e., more preferably not less than 99.0% e.e., especially preferably not less than 99.5% e.e., most preferably not less than 99.8% e.e.

(a) As the reaction to be carried out in the process of converting the isocyanate group to an amino group, a known method may be used, if appropriate. Specific examples of the method include a method in which an acid or a base is allowed to act to cause direct conversion to the amino group, and a method in which an alcohol is allowed to act to cause conversion to a carbamate, followed by its conversion to the amino group using an acid or a base, or by catalytic reduction.

Examples of the acid or the base to be used in the method by direct conversion to the amino group include inorganic acids such as hydrochloric acid and sulfuric acid; and alkali metal hydroxides such as sodium hydroxide and potassium hydroxide. In these cases, the reaction temperature is usually 0° C. to 200° C., and the reaction time is usually 30 minutes to 50 hours.

Examples of the method carried out through a carbamate include a method in which benzyl alcohol, p-methoxybenzyl alcohol, or the like is allowed to act to cause conversion to a benzyloxycarbonyl-protected amino group, followed by deprotection of the benzyloxycarbonyl group by catalytic reduction, and a method in which tert-butyl alcohol is allowed to act to cause conversion to a tert-butoxycarbonyl (hereinafter referred to as "Boc")-protected amino group, followed by allowing an acid to act for deprotection of the Boc group.

(b) In the process of hydrolyzing the ester group, water, and an acid or a base is allowed to act on the compound represented by the General Formula (6).

In cases where the hydrolysis is carried out by action of a base, examples of the base include alkali metal hydroxides such as sodium hydroxide, lithium hydroxide, and potassium hydroxide; and alkali metal carbonates such as lithium carbonate, sodium carbonate, and potassium carbonate.

In cases where the hydrolysis is carried out by action of an acid, examples of the acid include inorganic acids such as hydrochloric acid, sulfuric acid, phosphoric acid, hydrogen bromide, hydrogen fluoride, and hydrogen iodide; and organic acids such as trifluoroacetic acid, trifluoromethanesulfonic acid, methanesulfonic acid, and p-toluenesulfonic acid.

Both in the cases where the base is allowed to act, and in the cases where the acid is allowed to act, the reaction temperature is usually 0° C. to 200° C., and the reaction time is usually 30 minutes to 50 hours.

(c) In the process of removing the tert-butyl group by action of an acid, an acid is allowed to act on the compound represented by General Formula (6).

The acid to be used is not limited as long as the removal of the tert-butyl group can be achieved therewith, and is preferably a strong acid. Examples of the acid include inorganic acids such as hydrochloric acid, sulfuric acid, phosphoric acid, hydrogen bromide, hydrogen fluoride, and hydrogen iodide; and organic acids such as trifluoroacetic acid, trifluoromethanesulfonic acid, methanesulfonic acid, and p-toluenesulfonic acid. Among these, hydrochloric acid and sulfuric acid are preferred since these are inexpensive.

In such cases, the reaction temperature is usually 50° C. to 200° C., and the reaction time is usually 10 hours to 150 hours.

The above-described three processes: (a) converting the isocyanate group to an amino group, (b) hydrolyzing the ester group, and (c) removing the tert-butyl group, may be carried out in any order, and two or more processes may be carried out at the same time.

The step (v) is preferably carried out through the steps (vi-1), (vi-2), and (vii) described below. By allowing the reaction to proceed through the step (vi-1), elimination of the tert-butyl group, which generally requires a long time, can be allowed to proceed quickly to obtain a compound represented by General Formula (7-1):

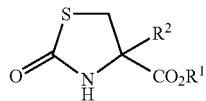

(7-1)

(wherein $R^1$ and $R^2$ have the same meanings as $R^1$ and $R^2$ in the General Formula (6)).

Further, by allowing the reaction to proceed through the step (vi-2), a compound represented by General Formula (7-2):

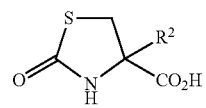

(7-2)

(wherein $R^2$ has the same meaning as $R^2$ in the General Formula (6)) can be obtained. Since the compound represented by the General Formula (7-2) has high crystallinity, and low solubility in water at a pH of not more than the point of neutralization, both water-soluble impurities including inorganic salts and water-insoluble impurities including reaction intermediates can be easily removed by crystallization. Thus, the α-substituted cysteine represented by General Formula (1) or the salt thereof obtained after the subsequent step (vii) can be obtained with high purity.

<Steps (vi-1) and (vi-2)>

The steps (vi-1) and (vi-2) are described below.

The step (vi-1) is a step of allowing an acid to act on a compound represented by General Formula (6):

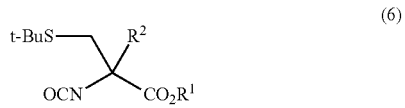

(6)

(wherein $R^1$ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ represents a $C_1$-$C_4$ alkyl group) to construct a thiazolidinone ring, thereby obtaining a compound represented by General Formula (7-1):

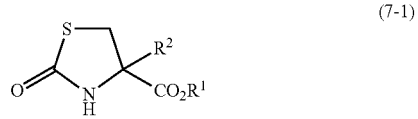

(7-1)

(wherein $R^1$ and $R^2$ have the same meanings as $R^1$ and $R^2$ in the General Formula (6)).

The $R^1$ and the $R^2$ in the compounds represented by the General Formulae (6) and (7-1) are the same as those described in the step (i).

Thus, specific examples of the compound represented by General Formula (7-1) include the following compounds.

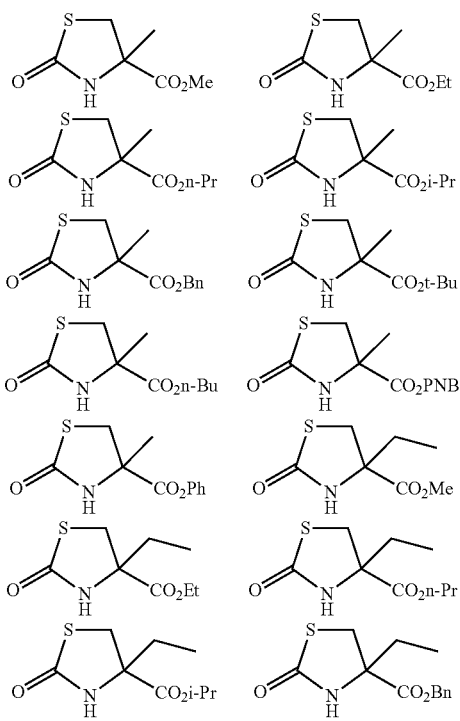

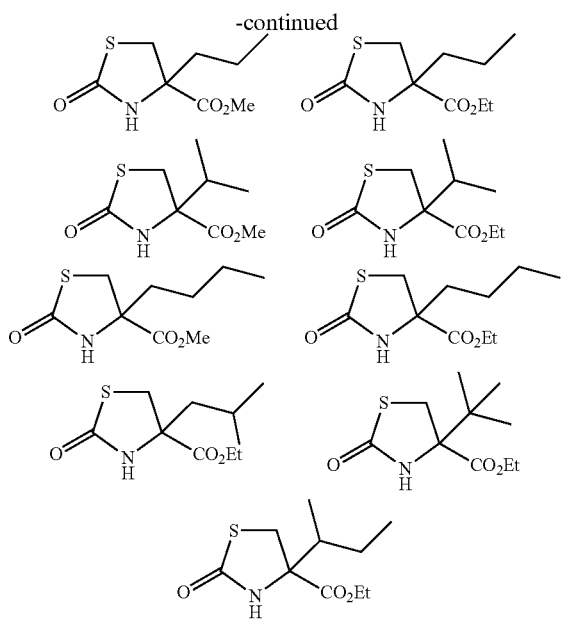

Among the compounds mentioned above, the following compounds are preferred as the compound represented by the General Formula (7-1).

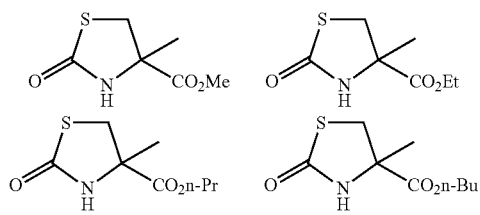

The compound represented by the General Formula (7-1) may be either a racemic compound or a chiral compound. Since high optical purity is generally required in cases where the compound is produced as a pharmaceutical or an intermediate therefor, the compound is preferably a chiral compound having high optical purity. The optical purity is preferably not less than 95.0% e.e., more preferably not less than 99.0% e.e., especially preferably not less than 99.5% e.e., most preferably not less than 99.8% e.e.

Examples of the acid used in the step (vi-1) include inorganic acids such as hydrochloric acid, sulfuric acid, phosphoric acid, hydrogen bromide, hydrogen fluoride, and hydrogen iodide; and organic acids such as trifluoroacetic acid, trifluoromethanesulfonic acid, methanesulfonic acid, and p-toluenesulfonic acid. Among these, hydrochloric acid, sulfuric acid, phosphoric acid, and p-toluenesulfonic acid are more preferred from the viewpoint of the cost.

The amount of the acid used may be appropriately set within the range of, for example, 0.01 molar equivalent to 50 molar equivalents with respect to the amount of the compound represented by General Formula (6). Considering the cost, and laboriousness of the post-treatment, the amount is preferably 0.1 molar equivalent to 10 molar equivalents, more preferably 0.5 molar equivalent to 3 molar equivalents.

Examples of the reaction solvent to be used include ketones such as acetone, 2-butanone, and methylisobutyl ketone; aromatic hydrocarbons such as benzene, toluene, xylene, chlorobenzene, and trifluoromethylbenzene; aliphatic hydrocarbons such as n-pentane, n-hexane, n-heptane, and cyclohexane; esters such as methyl acetate, ethyl acetate, and isopropyl acetate; ethers such as diethyl ether, di-n-propyl ether, di-n-butyl ether, methyl isopropyl ether, methyl-tert-butyl ether, ethyl-tert-butyl ether, cyclopentyl methyl ether, tetrahydrofuran, dioxane, and 1,2-dimethoxyethane; amides such as N,N-dimethylformamide and N,N-dimethylacetamide; nitriles such as acetonitrile and propionitrile; halogenated hydrocarbons such as dichloromethane, chloroform, carbon tetrachloride, and 1,2-dichloroethane; and dimethylsulfoxide. In cases where water or an alcohol is used, reaction with the compound represented by General Formula (6) tends to occur to produce a dimer having a urea structure or a carbamate as a by-product, leading to a decrease in the yield. Thus, use of water or an alcohol as a main solvent for the step (vi-1) is not preferred. In cases where water or an alcohol is used for dissolving an inorganic acid or an inorganic base, the amount of the water or the alcohol used is preferably minimum.

Thus, among the reaction solvents described above, aromatic hydrocarbons such as benzene, toluene, xylene, chlorobenzene, and trifluoromethylbenzene; aliphatic hydrocarbons such as n-pentane, n-hexane, n-heptane, and cyclohexane; and halogenated hydrocarbons such as dichloromethane, chloroform, carbon tetrachloride, and 1,2-dichloroethane; are preferred from the viewpoint of stability against acids. It is more preferred to carry out the this step using toluene or xylene continuously from the step (iv) without changing the solvent, from the viewpoint of the cost.

The reaction temperature may be appropriately set within the range of, for example, −30° C. to 100° C. However, since, in cases where the reaction is carried out within the range of 70° C. to 100° C., the compound represented by General Formula (7-1) produced is converted to the compound represented by General Formula (7-2) in a short time. Thus, in cases where the compound represented by General Formula (7-1) is to be isolated, the reaction is carried out preferably within the range of −30° C. to 50° C., more preferably within the range of 0° C. to 30° C.

The reaction time may be appropriately set within the range of, for example, 0.5 hour to 20 hours. In cases where the reaction is carried out for a reaction time within the range of 10 hours to 20 hours, the compound represented by General Formula (7-1) produced tends to be converted to the compound represented by General Formula (7-2) depending on the temperature setting. Thus, in cases where the compound represented by General Formula (7-1) is to be isolated, the reaction time is preferably 0.5 hour to 10 hours, more preferably 0.5 hour to 3 hours.

If necessary, post-treatment may be carried out. For example, neutralization may be carried out by adding a base; water and a water-insoluble organic solvent may be added to perform extraction; and/or, in cases where the acid is volatile, it may be removed by concentration. From the viewpoint of simplification of the process, it is preferred to proceed to the step (vi-2) described below without carrying out post-treatment.

The step (vi-2) is a step of allowing an acid or a base to act on a compound represented by General Formula (7-1):

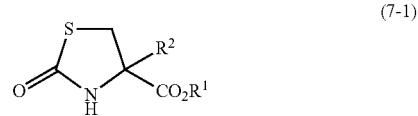

(7-1)

(wherein $R^1$ and $R^2$ have the same meanings as $R^1$ and $R^2$ in the General Formula (6)) to hydrolyze the ester group, and thereby obtain a compound represented by General Formula (7-2):

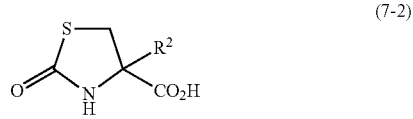

(7-2)

(wherein $R^2$ has the same meaning as $R^2$ in the General Formula (6)).

The $R^2$ in the General Formulae (7-1) and (7-2) are the same as that described in the step (i).

Thus, specific examples of the compound represented by the General Formula (7-2) include the following compounds.

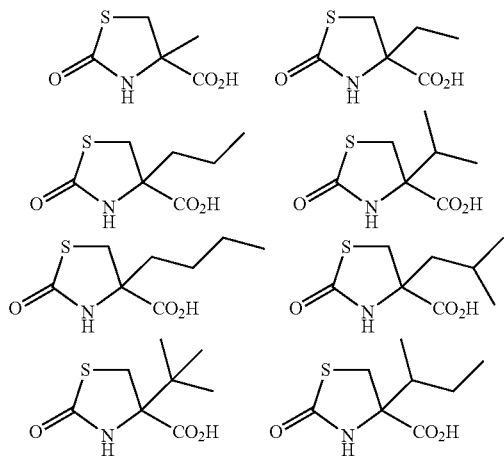

Among the compounds mentioned above, the following compounds are preferred as the compound represented by the General Formula (7-2).

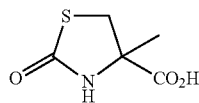

The compound represented by the General Formula (7-2) may be either a racemic compound or a chiral compound. Since high optical purity is generally required in cases where the compound is produced as a pharmaceutical or an intermediate therefor, the compound is preferably a chiral compound having high optical purity. The optical purity is preferably not less than 95.0% e.e., more preferably not less than 99.0% e.e., especially preferably not less than 99.5% e.e., most preferably not less than 99.8% e.e.

Examples of the acid used in the step (vi-2) include inorganic acids such as hydrochloric acid, sulfuric acid, phosphoric acid, hydrogen bromide, hydrogen fluoride, and hydrogen iodide; and organic acids such as trifluoroacetic acid, trifluoromethanesulfonic acid, methanesulfonic acid, and p-toluenesulfonic acid. Among these, hydrochloric acid, sulfuric acid, and phosphoric acid are more preferred from the viewpoint of the cost. Hydrochloric acid is still more preferred since it is a volatile acid and can be easily removed by concentration.

Alternatively, a base may be allowed to act to perform the hydrolysis. Examples of the base to be used include alkali metal hydroxides such as lithium hydroxide, sodium hydroxide, and potassium hydroxide; and alkali metal carbonates such as sodium carbonate, lithium carbonate, and potassium carbonate.

In cases where a base is used, its recovery by filtration needs to be carried out after adjustment of the pH by addition of an acid since, as described above, the compound represented by the General Formula (7-2) has low solubility in acidic water, but has high solubility in basic water. Since this is accompanied by the risk of contamination with an inorganic salt generated during the neutralization, an acid is preferably used from the viewpoint of quality.

Since an acid is also used in the step (vi-1), the acid used in the step (vi-1) may be allowed to act continuously without replacement, to continuously carry out the step (vi-1) and the step (vi-2). Alternatively, an acid may be further added in the step (vi-2). In such a case, the acid may be either the same as, or different from, the acid used in the step (vi-1). However, from the viewpoint of simplification of the process, it is preferred to allow the acid used in the step (vi-1) to act continuously without carrying out post-treatment after the step (vi-1), to carry out these steps continuously. That is, the reaction solution containing the compound represented by the General Formula (7-1) obtained in the step (vi-1) is preferably used in the step (vi-2) as it is after, for example, changing the reaction temperature.

In cases where an acid is used, the amount of the acid used may be appropriately set within the range of 0.01 molar equivalent to 50 molar equivalents with respect to the amount of the compound represented by General Formula (7-1). Considering the cost, and laboriousness of the post-treatment, the amount is preferably 0.1 molar equivalent to 10 molar equivalents, more preferably 0.5 molar equivalent to 2 molar equivalents.

In cases where an acid is used, examples of the reaction solvent include water; ketones such as acetone, 2-butanone, and methylisobutyl ketone; aromatic hydrocarbons such as benzene, toluene, xylene, chlorobenzene, and trifluoromethylbenzene; aliphatic hydrocarbons such as n-pentane, n-hexane, n-heptane, and cyclohexane; esters such as methyl acetate, ethyl acetate, and isopropyl acetate; ethers such as diethyl ether, di-n-propyl ether, di-n-butyl ether, methyl isopropyl ether, methyl-tert-butyl ether, ethyl-tert-butyl ether, cyclopentyl methyl ether, tetrahydrofuran, dioxane, and 1,2-dimethoxyethane; amides such as N,N-dimethylformamide and N,N-dimethylacetamide; nitriles such as acetonitrile and propionitrile; halogenated hydrocarbons such as dichloromethane, chloroform, carbon tetrachloride, and 1,2-dichloroethane; and dimethylsulfoxide.

Since alcohols tend to inhibit the progress of the hydrolysis, aromatic hydrocarbons such as benzene, toluene, xylene, chlorobenzene, and trifluoromethylbenzene; aliphatic hydrocarbons such as n-pentane, n-hexane, n-heptane, and cyclohexane; and halogenated hydrocarbons such as dichloromethane, chloroform, carbon tetrachloride, and 1,2-dichloroethane; are preferred among the reaction solvents described above, from the viewpoint of stability against acids. Benzene, toluene, xylene, chlorobenzene, and trifluoromethylbenzene are more preferred since these allow heating at high temperature. Most preferably, toluene or xylene is used continuously from the step (vi-1), from the viewpoint of the cost.

In cases where an acid is used, the amount of the solvent used may be appropriately set within the range of, for example, 0 volume to 100 volumes with respect to the amount of the compound represented by General Formula (6). From the viewpoint of the volume efficiency, the amount is preferably 0 volume to 20 volumes, more preferably 0 volume to 5 volumes.

In cases where an acid is used, the reaction temperature may be appropriately set within the range of, for example, −30° C. to 200° C. Considering improvement of the degree of conversion and the boiling point of the solvent, the reaction temperature is preferably 20° C. to 120° C. In cases where the temperature is too high, degradation of the compound represented by General Formula (7-2) proceeds, leading to a decrease in the yield. Thus, the reaction temperature is more preferably 50° C. to 90° C.

In cases where an acid is used, the reaction time may be appropriately set within the range of, for example, 0 hour to 100 hours. Depending on the temperature, in cases where the reaction is carried out for a long time, degradation of the compound represented by General Formula (7-2) proceeds, leading to a decrease in the yield. Therefore, the reaction time is preferably 0 hour to 30 hours. From the viewpoint of improvement of the degree of conversion, the reaction time is more preferably 5 hours to 30 hours.

In cases where an acid is used, examples of the post-treatment after the reaction include a method in which the compound represented by General Formula (7-2) is recovered from the reaction solvent by crystallization taking advantage of the fact that the compound is solid in an acidic solution. Alternatively, if necessary, the solvent may be simply removed by concentration; the reaction solution may be neutralized using an acid or a base, and salt may be separated by adsorption of the product of interest to an ion-exchange resin, followed by recovering the product by crystallization; the acid or the base may be removed by adsorption to an ion-exchange resin, followed by recovering the compound from the eluate by crystallization; or, depending on the purity, purification may be carried out using a column or by recrystallization. In cases where only an acid is used, the compound represented by General Formula (7-2) generally has high crystallinity, and can be recovered with high purity. Therefore, it is preferred to recover the compound from the reaction solvent by performing only crystallization.

In cases where a base is used, examples of the reaction solvent include, from the viewpoint of stability against the base, water; ketones such as acetone, 2-butanone, and methylisobutyl ketone; alcohols such as methanol, ethanol, n-propyl alcohol, isopropyl alcohol, n-butanol, and tert-butanol; aromatic hydrocarbons such as benzene, toluene, xylene, chlorobenzene, and trifluoromethylbenzene; aliphatic hydrocarbons such as n-pentane, n-hexane, n-heptane, and cyclohexane; esters such as methyl acetate, ethyl acetate, and isopropyl acetate; ethers such as diethyl ether, di-n-propyl ether, di-n-butyl ether, methyl isopropyl ether, methyl-tert-butyl ether, ethyl-tert-butyl ether, cyclopentyl methyl ether, tetrahydrofuran, dioxane, and 1,2-dimethoxyethane; amides such as N,N-dimethylformamide and N,N-dimethylacetamide; nitriles such as acetonitrile and propionitrile; halogenated hydrocarbons such as dichloromethane, chloroform, carbon tetrachloride, and 1,2-dichloroethane; and dimethylsulfoxide. In particular, preferred examples of the reaction solvent include aromatic hydrocarbons such as benzene, toluene, xylene, chlorobenzene, and trifluoromethylbenzene; aliphatic hydrocarbons such as n-pentane, n-hexane, n-heptane, and cyclohexane; and ethers such as diethyl ether, di-n-propyl ether, di-n-butyl ether, methyl isopropyl ether, methyl-tert-butyl ether, ethyl-tert-butyl ether, cyclopentyl methyl ether, tetrahydrofuran, dioxane, and 1,2-dimethoxyethane. Among these, benzene, toluene, xylene, chlorobenzene, and trifluoromethylbenzene are more preferred since these allow heating at high temperature. Most preferably, toluene or xylene is used continuously from the step (vi-1) from the viewpoint of the cost.

In cases where a base is used, the amount of the base may be appropriately set within the range of 0.9 molar equivalent to 20 molar equivalents with respect to the amount of the compound represented by General Formula (7-1). Considering the cost, and laboriousness of the post-treatment, the amount is preferably 0.9 molar equivalent to 5.0 molar equivalents, more preferably 1.0 molar equivalent to 3.0 molar equivalents. In cases where no post-treatment is carried out after the step (vi-1), and the acid used in the step (vi-1) is continuously allowed to act to carry out the this step continuously from the step (vi-1), a base required for neutralization of the acid may be further added.

In cases where a base is used, the amount of the solvent used may be appropriately set within the range of, for example, 0 volume to 100 volumes with respect to the amount of the compound represented by General Formula (6). From the viewpoint of the volume efficiency, the amount is preferably 0 volume to 20 volumes, more preferably 0 volume to 5 volumes.

In cases where a base is used, the reaction temperature may be appropriately set within the range of, for example, −30° C. to 100° C. For suppression of side reactions, the reaction temperature is preferably 0° C. to 80° C. In cases where the temperature is too high, degradation of the compound represented by General Formula (7-2) may proceed, leading to a decrease in the yield. Thus, the reaction temperature is more preferably 0° C. to 50° C.

In cases where a base is used, the reaction time may be appropriately set within the range of, for example, 0 hour to 100 hours. Depending on the temperature, in cases where the reaction is carried out for a long time, degradation of the compound represented by General Formula (7-2) may proceed, leading to a decrease in the yield. Therefore, the reaction time is preferably 0 hour to 30 hours. From the viewpoint of improvement of the degree of conversion, the reaction time is more preferably 5 hours to 30 hours.

In cases where a base is used, this reaction may be followed by a post-treatment in which the compound represented by General Formula (7-2) is recovered from the reaction solvent by crystallization taking advantage of the fact that the compound is solid in an acidic solution. More specifically, the base may be neutralized with an acid, and then an acid may be further added. Alternatively, the solvent may be simply removed by concentration; the reaction solution may be neutralized using an acid, and salt may be separated by adsorption of the product of interest to an ion-exchange resin, followed by recovering the product by crystallization; or the base may be removed by adsorption to an ion-exchange resin, followed by recovering the product of interest from the eluate by crystallization. Depending on the purity, purification may be carried out using a column or by recrystallization. However, in cases where only an acid is used, the compound represented by General Formula (7-2) generally has high crystallinity, and can be recovered with high purity. Therefore, it is preferred to recover the compound from the reaction solvent by performing only crystallization.

Among the compounds represented by General Formula (7-2), General Formula (7S-2):

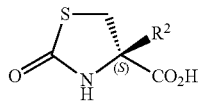

(7S-2)

(wherein $R^2$ has the same meaning as $R^2$ in the General Formula (7-2))
and General Formula (7R-2):

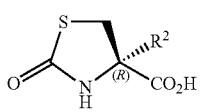

(7R-2)

(wherein $R^2$ has the same meaning as $R^2$ in the General Formula (7-2)) have higher crystallinity than racemic compounds. Accordingly, improvement of the optical purity by crystallization or the like can be more easily carried out with a chiral compound wherein either one of General Formula (7S-2) or General Formula (7R-2) is selectively contained, compared to a racemic compound.

In cases where the optical purity of the compound represented by General Formula (7-2) does not reach a desired level after carrying out the post-treatment described above, recrystallization may be repeated to increase the optical purity. In particular, in cases where the compound represented by General Formula (1) in the step (vii) described later is a chiral compound, the optical purity of the compound represented by General Formula (7-2) as a material is preferably preliminarily increased to a desired level by crystallization.

Examples of the crystallization solvent for the compound represented by General Formula (7-2) include water; alcohols such as methanol, ethanol, n-propyl alcohol, isopropyl alcohol, n-butanol, and tert-butanol; ketones such as acetone, 2-butanone, and methylisobutyl ketone; aromatic hydrocarbons such as benzene, toluene, xylene, chlorobenzene, and trifluoromethylbenzene; aliphatic hydrocarbons such as n-pentane, n-hexane, n-heptane, and cyclohexane; esters such as methyl acetate, ethyl acetate, and isopropyl acetate; ethers such as diethyl ether, di-n-propyl ether, di-n-butyl ether, methyl isopropyl ether, methyl-tert-butyl ether, ethyl-tert-butyl ether, cyclopentyl methyl ether, tetrahydrofuran, dioxane, and 1,2-dimethoxyethane; amides such as N,N-dimethylformamide and N,N-dimethylacetamide; nitriles such as acetonitrile and propionitrile; halogenated hydrocarbons such as dichloromethane, chloroform, carbon tetrachloride, and 1,2-dichloroethane; and dimethylsulfoxide. One of these solvents may be used, or two or more of the solvents may be used as a mixture.

In particular, preferred examples of the crystallization solvent include polar solvents, for example, alcohols such as methanol, ethanol, n-propyl alcohol, isopropyl alcohol, n-butanol, and tert-butanol; ketones such as acetone, 2-butanone, and methylisobutyl ketone; esters such as methyl acetate, ethyl acetate, and isopropyl acetate; amides such as N,N-dimethylformamide and N,N-dimethylacetamide; nitriles such as acetonitrile and propionitrile; and dimethylsulfoxide; since these show high solubility and high purification efficiency. Among these, alcohols such as methanol, ethanol, n-propyl alcohol, isopropyl alcohol, n-butanol, and tert-butanol; ketones such as acetone, 2-butanone, and methylisobutyl ketone; esters such as methyl acetate, ethyl acetate, and isopropyl acetate; and nitriles such as acetonitrile and propionitrile; are more preferred since these have low boiling points, and can be easily removed by vacuum drying.

For improvement of the recovery, it is preferred to add, as a poor solvent(s), one or more of low-polarity solvents to these polar solvents. Examples of the low-polarity solvents include aromatic hydrocarbons such as benzene, toluene, xylene, chlorobenzene, and trifluoromethylbenzene; and aliphatic hydrocarbons such as n-pentane, n-hexane, n-heptane, and cyclohexane.

<Step (vii)>

The step (vii) is described below.

The step (vii) is a step of allowing an acid or a base to act on a compound represented by General Formula (7-2):

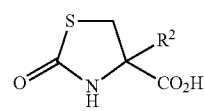

(7-2)

(wherein $R^2$ represents a $C_1$-$C_4$ alkyl group)
to open the thiazolidinone ring, and thereby obtain an α-substituted cysteine represented by General Formula (1):

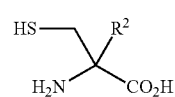

(1)

(wherein $R^2$ represents a $C_1$-$C_4$ alkyl group)
or the salt thereof.

Examples of the acid used in the step (vii) include inorganic acids such as hydrochloric acid, sulfuric acid, phosphoric acid, hydrogen bromide, hydrogen fluoride, and hydrogen iodide; and organic acids such as trifluoroacetic acid, trifluoromethanesulfonic acid, methanesulfonic acid, and p-toluenesulfonic acid.

Examples of the base include alkali metal hydroxides such as lithium hydroxide, sodium hydroxide, and potassium hydroxide; and alkali metal carbonates such as sodium carbonate, lithium carbonate, and potassium carbonate. Among these, strong bases are preferred. Specific examples of the strong bases include alkali metal hydroxides such as lithium hydroxide, sodium hydroxide, and potassium hydroxide.

In cases where a base is used, dimerization of the resulting α-substituted cysteine easily occurs to form a disulfide. Therefore, an acid is preferably used from the viewpoint of the yield and the quality. In particular, volatile acids such as hydrochloric acid, trifluoroacetic acid, hydrogen bromide, hydrogen fluoride, and hydrogen iodide are more preferred since these can be removed by performing only concentration. From the viewpoint of the cost, hydrochloric acid is most preferred.

The acid or the base used in the step (vi-2) can also be used as at least part of the acid or the base used in the step (vii). That is, by subjecting the reaction solution obtained in the step (vi-2) as it is to the reaction conditions for the later-described step (vii) without carrying out post-treatment after the step (vi-2), an α-substituted cysteine represented by General Formula (1):

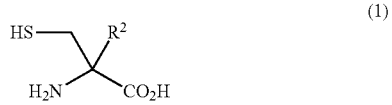

(wherein $R^2$ represents a $C_1$-$C_4$ alkyl group) or a salt thereof can be obtained.

However, in cases where the α-substituted cysteine represented by General Formula (1) or the salt thereof is to be produced with high purity, the compound represented by General Formula (7-2), which is used as a material, also needs to be highly pure. Thus, from the viewpoint of quality control, it is preferred to carry out, as described above, the operation of recovering the compound represented by General Formula (7-2) after the step (vi-2) by crystallization to remove impurities, followed by carrying out the step (vii).

The amount of the acid or the base used may be appropriately set within the range of, for example, 0.1 molar equivalent to 200 molar equivalents with respect to the amount of the compound represented by General Formula (7). From the viewpoint of the volume efficiency, the amount is preferably 1 molar equivalent to 30 molar equivalents. In cases where an acid is used, the compound represented by General Formula (7) is preferably completely dissolved in the acid from the viewpoint of reducing the reaction time. Considering the load of the process of removing the acid, the amount of the acid is more preferably 5 molar equivalents to 20 molar equivalents.

The reaction may be carried out in the presence of a solvent, if necessary. Examples of the solvent include water; alcohols such as methanol, ethanol, n-propyl alcohol, isopropyl alcohol, and n-butanol; ketones such as acetone, 2-butanone, and methylisobutyl ketone; aromatic hydrocarbons such as benzene, toluene, xylene, chlorobenzene, and trifluoromethylbenzene; aliphatic hydrocarbons such as n-pentane, n-hexane, n-heptane, and cyclohexane; esters such as methyl acetate, ethyl acetate, and isopropyl acetate; ethers such as diethyl ether, di-n-propyl ether, di-n-butyl ether, methyl isopropyl ether, methyl-tert-butyl ether, ethyl-tert-butyl ether, cyclopentyl methyl ether, tetrahydrofuran, dioxane, and 1,2-dimethoxyethane; amides such as N,N-dimethylformamide and N,N-dimethylacetamide; nitriles such as acetonitrile and propionitrile; halogenated hydrocarbons such as dichloromethane, chloroform, carbon tetrachloride, and 1,2-dichloroethane; and dimethylsulfoxide. In cases where an acid is used, the solvent is preferably one which does not cause a side reaction with the acid. Aromatic hydrocarbons such as benzene, toluene, xylene, chlorobenzene, and trifluoromethylbenzene; and aliphatic hydrocarbons such as n-pentane, n-hexane, n-heptane, and cyclohexane; are preferred. However, since, as the concentration of the acid increases, the reaction is better promoted, it is more preferred to use the acid as a solvent without using another solvent.

The reaction temperature may be appropriately set within the range of, for example, −30° C. to 300° C. Considering the boiling point of the solvent, the reaction temperature is preferably 25° C. to 150° C. In particular, in cases where a volatile acid is used, the reaction temperature is more preferably 80° C. to 110° C., since the acid volatilizes and the acid concentration decreases when the reaction temperature exceeds the boiling point, resulting in a decrease in the reaction rate. It is also possible to carry out the reaction using a sealable, pressure-resistant reaction vessel while preventing volatilization of the acid. In such cases, the preferred range of the reaction temperature is not limited to the range described above.

The reaction time may be appropriately set within the range of, for example, 1 hour to 300 hours. From the viewpoint of the yield, the reaction time is preferably 10 hours to 200 hours. In cases where an acid is used, the reaction time is more preferably 40 hours to 100 hours.

In cases where an acid is used, the post-treatment of the reaction may be appropriately selected depending on whether the α-substituted cysteine is recovered as a salt or not. For example, in cases where the α-substituted cysteine is recovered as a salt with an acid, the solvent may be removed by concentration. In cases where the α-substituted cysteine is recovered as an α-substituted cysteine, a base may be added to the reaction solution to the point of neutralization to precipitate the α-substituted cysteine, followed by recovering the α-substituted cysteine by filtration. Alternatively, the reaction solution may be passed through a cation-exchange column to adsorb the α-substituted cysteine, thereby removing the acid, and the eluate containing the α-substituted cysteine may then be concentrated to recover the α-substituted cysteine. For obtaining an α-substituted cysteine or a salt thereof with high purity, recrystallization is preferably carried out to increase the purity.

In cases where the recrystallization is carried out, examples of the crystallization solvent include water; alcohols such as methanol, ethanol, n-propyl alcohol, isopropyl alcohol, n-butanol, and tert-butanol; ketones such as acetone, 2-butanone, and methylisobutyl ketone; aromatic hydrocarbons such as benzene, toluene, xylene, chlorobenzene, and trifluoromethylbenzene; aliphatic hydrocarbons such as n-pentane, n-hexane, n-heptane, and cyclohexane; esters such as methyl acetate, ethyl acetate, and isopropyl acetate; ethers such as diethyl ether, di-n-propyl ether, di-n-butyl ether, methyl isopropyl ether, methyl-tert-butyl ether, ethyl-tert-butyl ether, cyclopentyl methyl ether, tetrahydrofuran, dioxane, and 1,2-dimethoxyethane; amides such as N,N-dimethylformamide and N,N-dimethylacetamide; nitriles such as acetonitrile and propionitrile; halogenated hydrocarbons such as dichloromethane, chloroform, carbon tetrachloride, and 1,2-dichloroethane; and dimethylsulfoxide. One of these solvents may be used, or two or more of the solvents may be used as a mixture. Alcohols such as methanol, ethanol, n-propyl alcohol, isopropyl alcohol, n-butanol, and tert-butanol; and ketones such as acetone, 2-butanone, and methylisobutyl ketone; are preferred since the purification can be carried out effectively with these.

Since an α-substituted cysteine is highly soluble in these solvents, and crystallization in a single solvent results in a low recovery, it is more preferred to add, as a poor solvent (s), one or more of nonpolar solvents such as aromatic hydrocarbons including benzene, toluene, xylene, chlorobenzene, and trifluoromethylbenzene; and aliphatic hydrocarbons such as n-pentane, n-hexane, n-heptane, and cyclohexane. In particular, the combination of one or more of alcohols such as methanol, ethanol, n-propyl alcohol, isopropyl alcohol, n-butanol, and tert-butanol; and one or more of aromatic hydrocarbons such as benzene, toluene, xylene, chlorobenzene, and trifluoromethylbenzene; is more preferred since both effective purification and high recovery can be achieved. Considering ease of removal of the solvent by drying after filtration, and safety of the operator, the combination of methanol, ethanol, or isopropyl alcohol; and toluene; is most preferred.

[Method for Producing α-Substituted Cysteine Represented by General Formula (1S) or Salt Thereof]

Among the α-substituted cysteines represented by the General Formula (1) and salts thereof, α-substituted-D-cysteines having an (S)-configuration, represented by General Formula (1S):

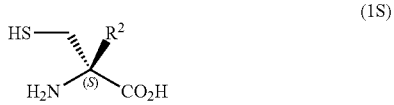
(1S)

(wherein $R^2$ represents a $C_1$-$C_4$ alkyl group),
and salts thereof are useful as intermediates for pharmaceuticals and the like. In particular, α-methyl-D-cysteine and salts thereof, in which $R^2$ is methyl, are known to be useful as intermediates for hyperferremia, and establishment of a production method which enables their industrial-scale production has been expected.

Specific examples of the α-substituted cysteine represented by the General Formula (1S) include the following compounds.

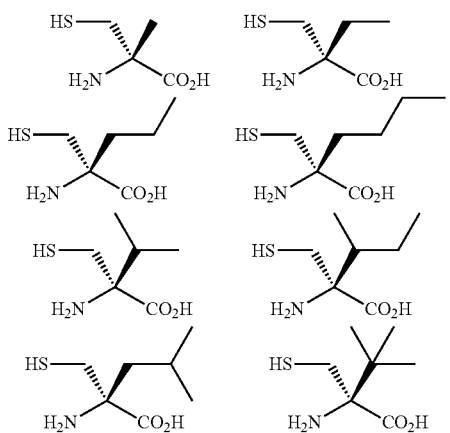

Among the compounds mentioned above, the following compound is preferred as the compound (1S).

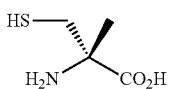

In cases where an α-substituted-D-cysteine represented by General Formula (1S) or a salt thereof is used as an intermediate for a pharmaceutical, high optical purity is required as described above. In general, the optical purity is preferably not less than 99.0% e.e., more preferably not less than 99.5% e.e., especially preferably not less than 99.8% e.e.

The method for producing an α-substituted-D-cysteine represented by General Formula (1S) or a salt thereof is described below. The reaction conditions in each step are the same as those described in [Method for Producing α-Substituted Cysteine Represented by General Formula (1) or Salt Thereof].

In order to produce an α-substituted-D-cysteine represented by General Formula (1S) or a salt thereof, the steps (ii) to (v) described above may be carried out using the compound represented by General Formula (3S):

(3S)

(wherein $R^1$ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted; and $R^2$ has the same meaning as in the General Formula (1S)) produced in the step (i) described above.

First, in the step (ii), a condensing agent or an acid halogenating agent may be allowed to act on the General Formula (3S), to obtain a compound represented by General Formula (4S):

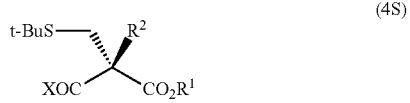
(4S)

(wherein $R^1$ and $R^2$ have the same meanings as $R^1$ and $R^2$ in the General Formula (3S); and X represents —OP(O)(OPh)$_2$, —OP(O)(OEt)$_2$, —OC(O)OR$^3$, or a halogen atom). The compound represented by General Formula (4S) may be either an (S)-isomer or an (R)-isomer, depending on the type of X.

In particular, it is preferred to allow a chloroformic ester to act to obtain a compound represented by General Formula (4S-1):

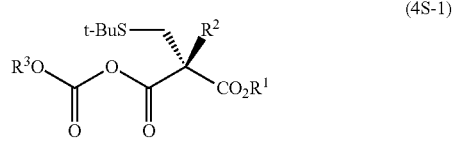
(4S-1)

(wherein $R^1$, $R^2$, and $R^3$ have the same meanings as $R^1$, $R^2$, and $R^3$ in the General Formula (4)), in which X is —OC(O)OR$^3$.

Specific examples of the compound represented by the General Formula (4S-1) include the following compounds.

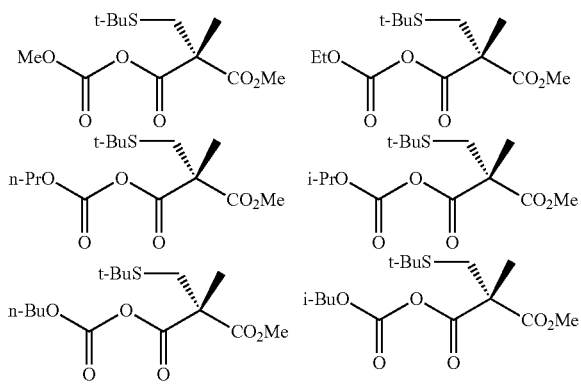

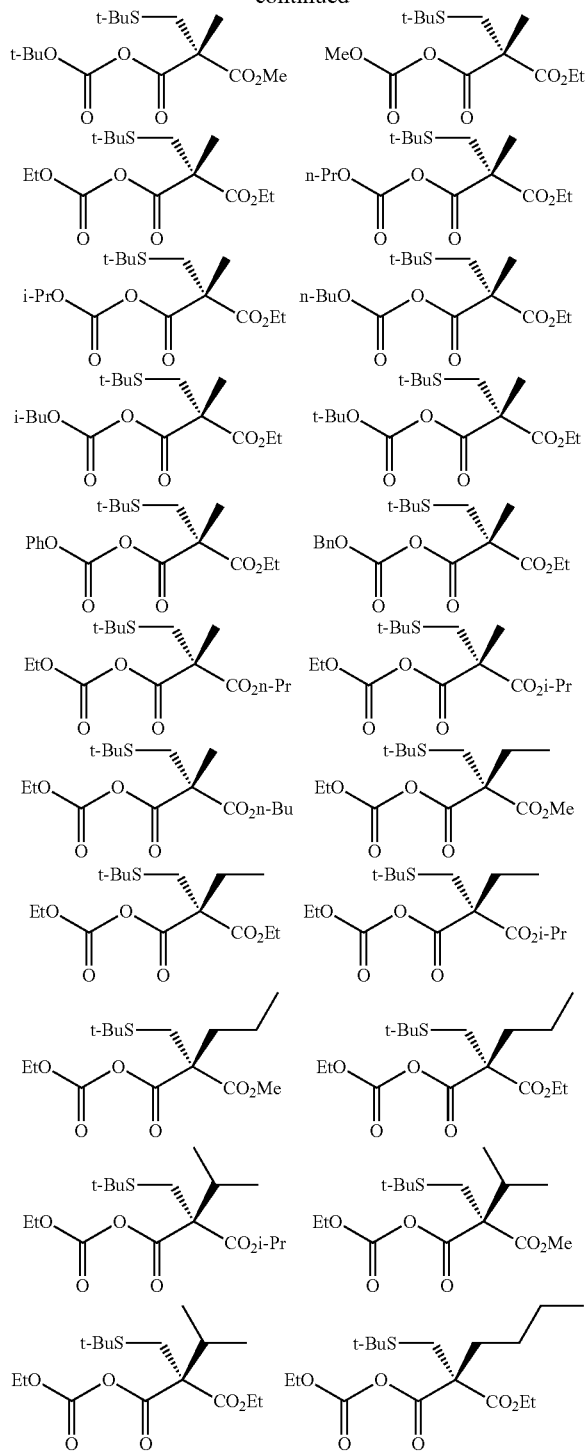

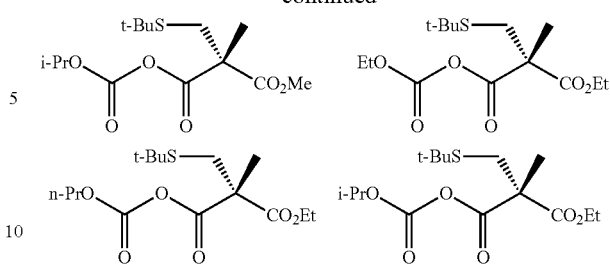

Subsequently, in the step (iii), an azidation agent may be allowed to act on the compound represented by General Formula (4S), to obtain a compound represented by General Formula (5S):

(5S)

(wherein $R^1$ and $R^2$ have the same meanings as $R^1$ and $R^2$ in the General Formula (4S)).

In particular, it is preferred to use, as a material, the compound represented by the General Formula (4S-1), in which X is $-OC(O)OR^3$.

Specific examples of the compound represented by the General Formula (5S) include the following compounds.

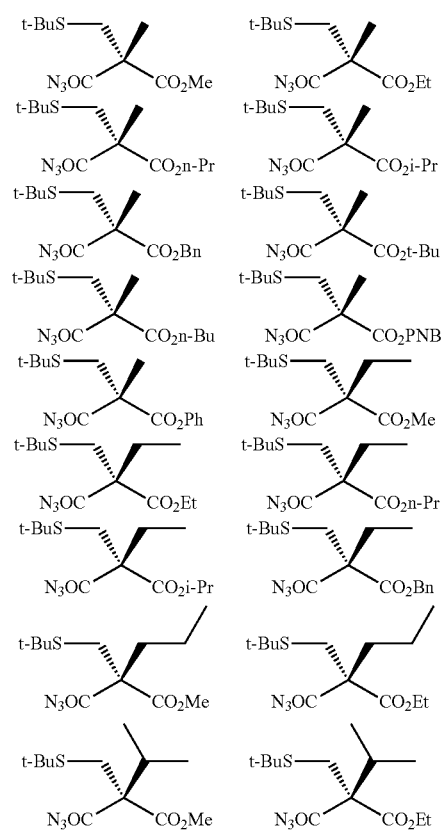

-continued

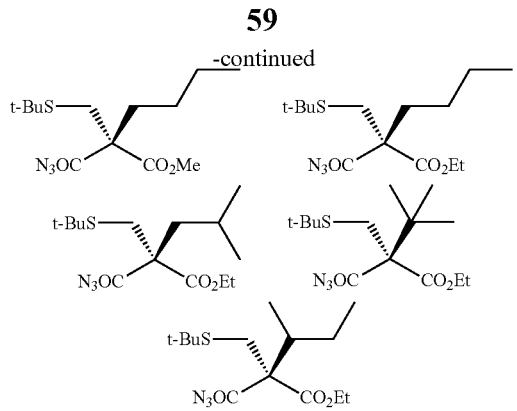

Among the compounds mentioned above, the following compounds are preferred as the compound represented by the General Formula (5S).

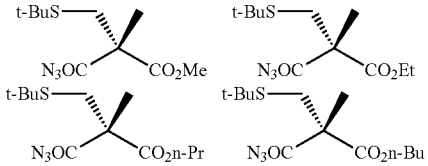

Subsequently, in the step (iv), the compound represented by the General Formula (5S) may be converted to a compound represented by General Formula (6S):

$$\text{(6S)}$$

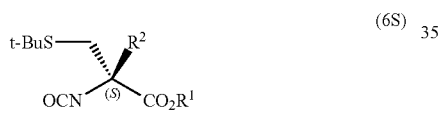

(wherein $R^1$ and $R^2$ have the same meanings as $R^1$ and $R^2$ in the General Formula (5S))
by Curtius rearrangement reaction.

Specific examples of the compound represented by the General Formula (6S) include the following compounds.

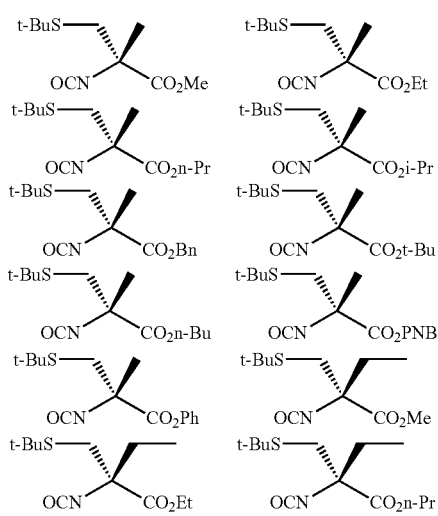

-continued

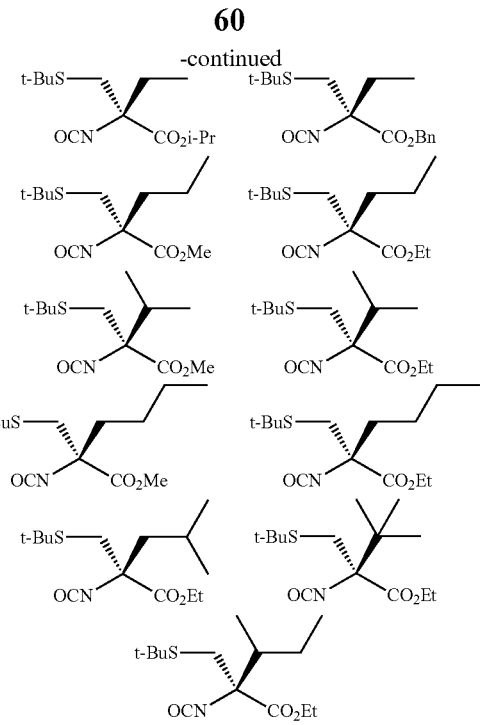

Among the compounds mentioned above, the following compounds are preferred as the compound represented by the General Formula (6S).

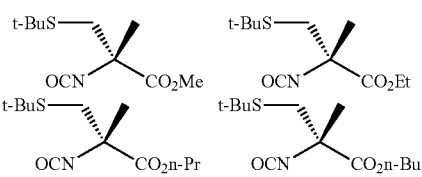

Subsequently, in the step (v), the compound of General Formula (1S) is obtained through the processes of: (a) converting the isocyanate group to an amino group; (b) hydrolyzing the ester group to allow its conversion to a carboxyl group; and (c) allowing an acid to act for removal of the tert-butyl group. In particular, after obtaining the compound represented by the General Formula (6S), the reaction is preferably allowed to proceed through the steps (vi-1), (vi-2), and (vii) described above.

That is, in the step (vi-1), an acid is allowed to act on the General Formula (6S) to construct a thiazolidinone ring, thereby allowing conversion to a compound represented by General Formula (7S-1):

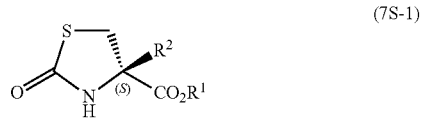

(7S-1)

(wherein $R^1$ and $R^2$ have the same meanings as $R^1$ and $R^2$ in the General Formula (6S)).

Subsequently, in the step (vi-2), an acid or a base is allowed to act on the compound represented by the General Formula (7S-1) to hydrolyze the ester group, thereby allowing conversion to a compound represented by General Formula (7S-2):

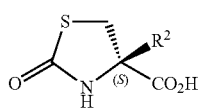

(7S-2)

(wherein R² has the same meaning as R² in the General Formula (7S-1)).

Subsequently, in the step (vii), an acid or a base is allowed to act on the General Formula (7S-2) to open the thiazolidinone ring, thereby obtaining the α-substituted-D-cysteine represented by the General Formula (1S) or the salt thereof.

In other words, by allowing the reaction to proceed through the step (vi-1), elimination of the tert-butyl group, which generally requires a long time, can be allowed to proceed quickly, and the compound represented by General Formula (7S-1) can be obtained in a short time. Since the compound represented by General Formula (7S-2) obtained in the subsequent step (vi-2) has high crystallinity, and low solubility in water at a pH of not more than the point of neutralization and in nonpolar solvents, both water-soluble impurities including inorganic salts and water-insoluble impurities including reaction intermediates can be easily removed by crystallization. Therefore, after the subsequent step (vii), the α-substituted-D-cysteine represented by General Formula (1S) or the salt thereof can be obtained with high purity. Moreover, since the compound represented by General Formula (7S-2) has higher crystallinity than the racemic body of the compound, its optical purity can be easily increased by crystallization. Therefore, the compound represented by the General Formula (7S) below:

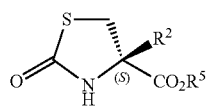

(7S)

(wherein R² has the same meaning as in General Formula (6); and R⁵ represents a hydrogen atom, or has the same meaning as R¹ in the General Formula (6S))

can be said to be an important intermediate for producing a high-quality α-substituted cysteine represented by General Formula (1S) or a salt thereof in a short time.

Here, General Formula (7S) includes General Formula (7S-1) and General Formula (7S-2).

Specific examples of the compound represented by the General Formula (7S) include the following compounds.

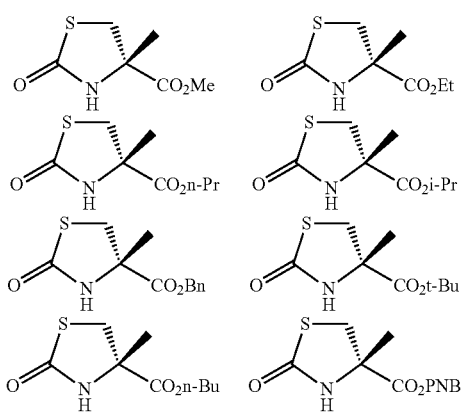

-continued

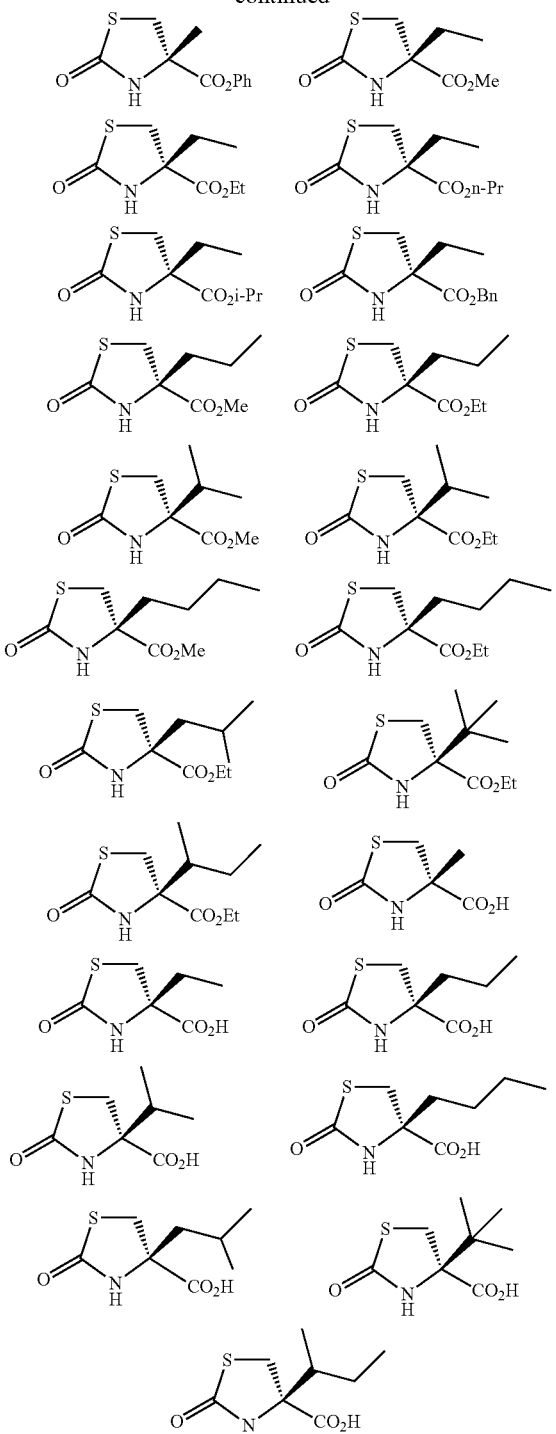

Among the compounds mentioned above, the following compounds are preferred as the compound represented by General Formula (7S).

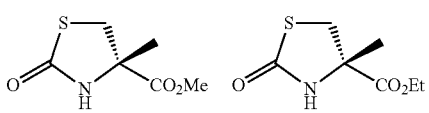

-continued

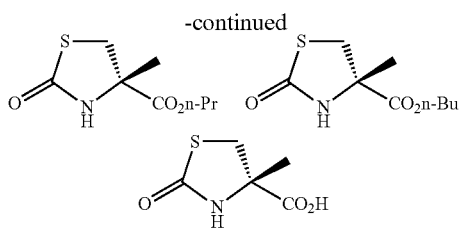

In cases where an α-substituted-D-cysteine represented by General Formula (1S) or a salt thereof is used as an intermediate for a pharmaceutical, high optical purity is required as described above. Therefore, in general, the optical purity of the compound represented by General Formula (7S), which is the precursor, is also preferably not less than 99.0% e.e., more preferably not less than 99.5% e.e., especially preferably not less than 99.8% e.e. In cases where the optical purity of General Formula (7-2) does not reach a desired level after carrying the step (vi-2), recrystallization may be repeated to increase the optical purity.

[Method for Producing Compound Represented by General Formula (2)]

The starting substance for the steps (i) to (vii) described above is a compound represented by General Formula (2):

(wherein each $R^1$ independently represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ represents a $C_1$-$C_4$ alkyl group). Conventional methods for producing this compound have been industrially unfavorable since bischloromethyl ether, which is a carcinogenic substance, may be generated.

In view of this, the present inventors discovered a method for safely producing the compound represented by General Formula (2) without generation of bischloromethyl ether. The method is described below.

The method for producing the compound represented by General Formula (2) comprises either the steps (viii) to (x) or the step (xi).

<Step (viii)>

First, the step (viii) is described below.

The step (viii) is a step of reacting tert-butyl mercaptan with formaldehyde to produce tert-butylthiomethanol.

As the tert-butyl mercaptan, a commercially available product may be used. As the formaldehyde, any of commercially available products in the form of paraformaldehyde, formalin, or 1,3,5-trioxane may be used. From the viewpoint of the cost and ease of handling, formalin is preferred.

The amount of formaldehyde may be appropriately set within the range of 0.7 molar equivalent to 10 molar equivalents with respect to the amount of tert-butyl mercaptan. In order to quantitatively obtain tert-butylthiomethanol, the amount is preferably 0.9 molar equivalent to 2.0 molar equivalents. From the viewpoint of the cost and ease of post-treatment, the amount is more preferably 0.9 molar equivalent to 1.2 molar equivalents.

In the this step, a solvent may be used. However, since the reaction proceeds even in cases where the formalin is used as a solvent without using another solvent, it is preferred not to use another solvent, from the viewpoint of the cost.

The reaction temperature may be appropriately set within the range of, for example, −50° C. to 200° C. The reaction temperature is preferably −20° C. to 100° C. Considering reactivity and the boiling point of tert-butyl mercaptan, the reaction temperature is more preferably 40° C. to 80° C.

The reaction time may be appropriately set within the range of, for example, 0.5 hour to 100 hours. The reaction time is preferably 1 hour to 40 hours, more preferably 5 hours to 20 hours.

In cases where formaldehyde remains in the tert-butylthiomethanol after the reaction of the this step, the formaldehyde may react with a substance that generates hydrogen chloride such as a chlorination agent in the step (ix) described below, to cause generation of bischloromethyl ether, which is a carcinogenic substance. Thus, in cases where excessive formaldehyde is used, a step for removing the formaldehyde needs to be included as a post-treatment. For example, a method in which water and a water-insoluble organic solvent are added to perform washing with water for removing formaldehyde into the aqueous layer, a method in which tert-butylthiomethanol is purified by distillation, a method in which solid paraformaldehyde is removed by filtration, or the like may be employed. Among these, the method in which water and a water-insoluble organic solvent are added to perform washing with water is preferred since formaldehyde can be efficiently removed by the method.

The water-insoluble organic solvent to be used for the washing with water include aromatic hydrocarbons such as benzene, toluene, xylene, and chlorobenzene; aliphatic hydrocarbons such as n-pentane, n-hexane, n-heptane, and cyclohexane; esters such as methyl acetate, ethyl acetate, and isopropyl acetate; ethers such as diethyl ether, di-n-propyl ether, di-n-butyl ether, methyl isopropyl ether, and cyclopentyl methyl ether; and halogenated hydrocarbons such as dichloromethane, chloroform, carbon tetrachloride, and 1,2-dichloroethane. Among these, aliphatic hydrocarbons such as n-pentane, n-hexane, n-heptane, and cyclohexane are preferred since these are highly separable from water, can be easily removed by distillation because of their low boiling points, and can be reused.

Depending on the water-insoluble organic solvent used, and in cases where water is used as a solvent, water in which an inorganic salt is dissolved is preferably used in order to minimize loss of tert-butylthiomethanol into the aqueous layer during the washing with water. From the viewpoint of the cost, saline is more preferably used.

<Step (ix)>

The step (ix) is described below.

The step (ix) is a step of allowing a chlorination agent to act, in the presence of a base, on the tert-butylthiomethanol obtained in the step (viii), to obtain tert-butylthiochloromethane.

Examples of the chlorination agent include hydrogen chloride, pivaloyl chloride, acetyl chloride, benzoyl chloride, thionyl chloride, phosphorous trichloride, phosphorous pentachloride, phosphorous oxytrichloride, oxalyl chloride, and sulfuryl chloride. Among these, thionyl chloride is preferred since it is inexpensive and shows high reaction selectivity.

The amount of the chlorination agent used may be appropriately set within the range of, for example, 0.7 molar equivalent to 10 molar equivalents with respect to the amount of tert-butylthiomethanol. From the viewpoint of the cost and ease of post-treatment, the amount is more preferably 0.8 molar equivalent to 3 molar equivalents. In order to quantitatively obtain tert-butylthiochloromethane, the amount is more preferably 0.9 molar equivalent to 1.2 molar equivalents.

The base is not limited as long as the base does not have nucleophilicity, and examples of the base include pyridines such as pyridine, 2-chloropyridine, 3-chloropyridine, 2-methylpyridine, 3-methylpyridine, 2,3-lutidine, 2,4-lutidine, 2,5-lutidine, 2,6-lutidine, 3,4-lutidine, and 3,5-lutidine; and tertiary amines such as triethylamine, triisopropylamine, dimethylisopropylamine, dimethylbutylamine, diethylmethylamine, diisopropylethylamine, and N-methylmorpholine. From the viewpoint of the cost, pyridine, triethylamine, and diisopropylethylamine are preferred. Pyridine is more preferred from the viewpoints of the fact that the solubility of the hydrochloric acid salt produced as a by-product in the later-described post-treatment method is advantageously low, and of the yield.

The amount of the base used may be appropriately set within the range of, for example, 0.7 molar equivalent to 10 molar equivalents with respect to the amount of tert-butylthiomethanol. The amount is preferably 0.8 molar equivalent to 5 molar equivalents. From the viewpoint of the cost and ease of post-treatment, the amount is more preferably 0.9 molar equivalent to 1.5 molar equivalents. The amount is most preferably 1.0 molar equivalent to 1.1 molar equivalents with respect to the amount of the chlorination agent used.

In the step (ix), a reaction solvent may be used. Examples of the reaction solvent include ketones such as acetone, 2-butanone, and methylisobutyl ketone; aromatic hydrocarbons such as benzene, toluene, xylene, chlorobenzene, and trifluoromethylbenzene; aliphatic hydrocarbons such as n-pentane, n-hexane, n-heptane, and cyclohexane; esters such as methyl acetate, ethyl acetate, and isopropyl acetate; ethers such as diethyl ether, di-n-propyl ether, di-n-butyl ether, methyl isopropyl ether, methyl-tert-butyl ether, ethyl-tert-butyl ether, cyclopentyl methyl ether, tetrahydrofuran, dioxane, and 1,2-dimethoxyethane; amides such as N,N-dimethylformamide and N,N-dimethylacetamide; nitriles such as acetonitrile and propionitrile; halogenated hydrocarbons such as dichloromethane, chloroform, carbon tetrachloride, and 1,2-dichloroethane; and dimethylsulfoxide.

Among these, toluene, xylene, chlorobenzene, n-pentane, n-hexane, n-heptane, cyclohexane, dichloromethane, and chloroform are preferred since these are inactive against acids, hardly cause side reactions, and can be reused. Aliphatic hydrocarbons such as n-pentane, n-hexane, n-heptane, and cyclohexane are more preferred since these are solvents in which the hydrochloric acid salt of the base produced as a by-product is hardly dissolved and can therefore be easily removed in the later-described post-treatment process.

The amount of water and alcohols contained is preferably minimum since they easily cause degradation of the chlorination agent.

The amount of the reaction solvent used may be appropriately set within the range of, for example, 0 volume to 100 volumes with respect to the amount of tert-butylthiomethanol. In cases where the solvent is not used, there is a problem in the safety of the process since a large amount of heat is generated in this step. From this view point, and also from the viewpoint of the volume efficiency, it is preferred to use 1 volume to 20 volumes of the reaction solution with respect to the amount of tert-butylthiomethanol. Considering securing of the stirring efficiency upon precipitation of the hydrochloric acid salt of the base as a by-product, and the volume efficiency, the amount of the reaction solvent is more preferably 5 volumes to 15 volumes.

The reaction temperature may be appropriately set within the range of, for example, −80° C. to 100° C. The reaction temperature is preferably −50° C. to 50° C. Since tert-butylthiochloromethane is degraded to cause a decrease in the yield in cases where the temperature is too high, the reaction temperature is more preferably −15° C. to 25° C.

The reaction time may be appropriately set within the range of, for example, 0.5 hour to 50 hours. The reaction time is preferably 1 hour to 20 hours. Since, in cases where the reaction is carried out for a long time, degradation of tert-butylthiochloromethane occurs, leading to a decrease in the yield, the reaction time is more preferably 1 hour to 8 hours.

As a post-treatment after this process, the hydrochloric acid salt of the base precipitated in the reaction solution may be removed by filtration or washing with water. After the removal, the solvent may be simply removed depending on the purity, or purification by distillation may be carried out. For example, in cases where pyridine is used as the base, simple removal of the solvent after filtration is sufficient since the solubility of pyridine hydrochloride in the solvent is low as described above. However, in addition, the operation of distillation is preferably carried out in order to obtain highly pure tert-butylthiochloromethane.

<Step (x)>

The step (x) is described below.

The step (x) is a step of allowing a compound represented by General Formula (8):

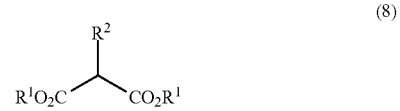

(wherein each $R^1$ independently represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ represents a $C_1$-$C_4$ alkyl group)

to act, in the presence of a base, on the tert-butylthiochloromethane obtained in the step (ix), to obtain a compound represented by General Formula (2):

(wherein $R^1$ and $R^2$ have the same meanings as $R^1$ and $R^2$ in the General Formula (8)).

The $R^1$ and the $R^2$ in the compound represented by General Formula (8) are the same as those described in the step (i).

Thus, specific examples of the compound represented by General Formula (8) include the following compounds.

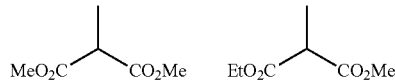

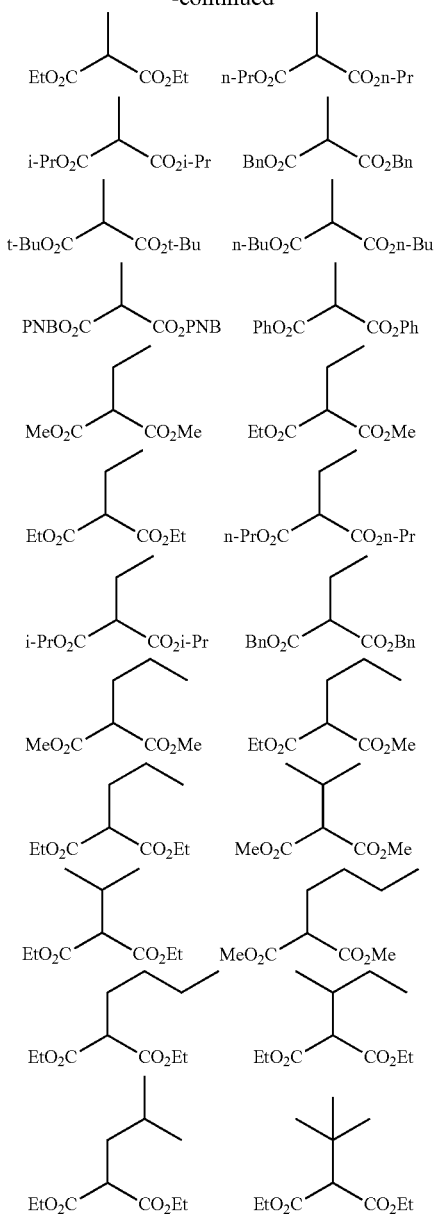

Among the compounds mentioned above, the following compounds are preferred as the compound represented by the General Formula (8).

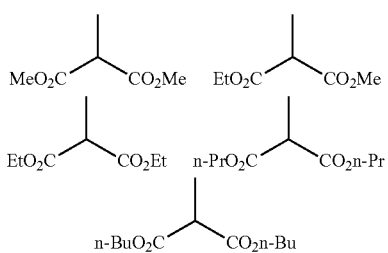

As the compound represented by General Formula (8), a commercially available product may be used. Alternatively, the compound represented by General Formula (8) may be produced according to, for example, the method described in Tetrahedron Letters (2008), 49, (15), 2446-2449, using the combination of a dialkyl malonate, a base, and an alkylating agent In the compound represented by General Formula (8), the $R^1$s are not necessarily the same, and may be different from each other. In cases where the $R^1$s are different from each other, two enantiomers, the (R)-isomer and the (S)-isomer, are present as the compound represented by the General Formula (8). The mixing ratio between these enantiomers is not limited.

The amount of tert-butylthiochloromethane used may be appropriately set within the range of, for example, 0.7 molar equivalent to 10 molar equivalents with respect to the amount of the compound represented by the General Formula (8). In order to quantitatively obtain the compound represented by General Formula (2), the amount is preferably 0.9 molar equivalent to 5 molar equivalents. The amount is more preferably 1.0 molar equivalent to 1.5 molar equivalents from the viewpoint of the cost.

Examples of the base include alkali metal alkoxides and alkali metal hydrides. Examples of the alkali metal alkoxides include lithium ethoxide, lithium methoxide, lithium tert-butoxide, sodium ethoxide, sodium methoxide, sodium tert-butoxide, potassium ethoxide, potassium methoxide, and potassium tert-butoxide. Examples of the alkali metal hydrides include lithium hydride, sodium hydride, and potassium hydride.

Among these, alkali metal alkoxides such as sodium ethoxide, sodium methoxide, sodium tert-butoxide, potassium ethoxide, potassium methoxide, and potassium tert-butoxide are preferred since they do not generate hydrogen during the reaction and can be safely handled, and the operation of removing mineral oil, which is contained in alkali metal hydrides, is not required. Potassium tert-butoxide is more preferred since it is highly soluble in organic solvents and has low nucleophilicity.

The amount of the base may be appropriately set within the range of, for example, 0.7 molar equivalent to 10 molar equivalents with respect to the amount of the compound represented by General Formula (8). In order to quantitatively obtain the compound represented by General Formula (2), the amount is preferably 0.9 molar equivalent to 5 molar equivalents. From the viewpoint of the cost and reduction of side reactions, the amount is more preferably 0.9 molar equivalent to 1.5 molar equivalents.

In this step, a reaction solvent may be used. Examples of the reaction solvent include aromatic hydrocarbons such as benzene, toluene, xylene, chlorobenzene, and trifluoromethylbenzene; aliphatic hydrocarbons such as n-pentane, n-hexane, n-heptane, and cyclohexane; ethers such as diethyl ether, di-n-propyl ether, di-n-butyl ether, methyl isopropyl ether, methyl-tert-butyl ether, ethyl-tert-butyl ether, cyclopentyl methyl ether, tetrahydrofuran, dioxane, and 1,2-dimethoxyethane; amides such as N,N-dimethylformamide and N,N-dimethylacetamide; halogenated hydrocarbons such as dichloromethane, chloroform, carbon tetrachloride, and 1,2-dichloroethane; and dimethylsulfoxide.

Among these, aprotic polar solvents such as tetrahydrofuran, dioxane, 1,2-dimethoxyethane, N,N-dimethylformamide, N,N-dimethylacetamide, and dimethylsulfoxide are preferred since the alkaline metal salt produced by the reaction between the compound represented by General Formula (8) and the base is highly soluble in these solvents, and the solvents therefore have an effect to promote the reaction. Tetrahydrofuran is more preferred since it is inexpensive and easily available.

The amount of the reaction solvent used may be appropriately set within the range of, for example, 0 volume to 100 volumes with respect to the amount of tert-butylthiochloromethane. In particular, from the viewpoint of the fact that the reaction more easily proceeds in cases where a solvent in which the alkaline metal salt of the compound represented by General Formula (8) dissolves is added, and from the viewpoint of the volume efficiency, the amount of the reaction solvent is preferably 1 volume to 20 volumes, more preferably 3 volumes to 8 volumes.

The reaction temperature may be appropriately set within the range of, for example, −100° C. to 200° C. The reaction temperature is preferably −50° C. to 100° C. In cases where the temperature is too low, solubility of the alkaline metal salt of the compound represented by General Formula (8) in the solvent decreases, so that the reaction proceeds slowly, while in cases where the temperature is too high, a side reaction may occur, leading to a decrease in the yield. Thus, the reaction temperature is more preferably −10° C. to 50° C.

The reaction time may be appropriately set within the range of, for example, 0.5 hour to 100 hours. The reaction time is preferably 1 hour to 20 hours. In cases where the reaction time is too long, a side reaction may occur, leading to a decrease in the yield. Thus, the reaction time is more preferably 1 hour to 10 hours.

Preferably, as a post-treatment after this reaction, the inorganic salt precipitated in the reaction solution may be removed by filtration, or water and a water-insoluble solvent may be added to the solution to remove the inorganic salt by washing with water. In particular, since, depending on the reaction solvent used, the inorganic salt is dissolved in the reaction solvent, washing water is more preferably included. When water is added to the reaction solution, the aqueous layer becomes basic. In order to suppress hydrolysis of the ester group in the compound represented by General Formula (8), a method in which acidic water is added to the reaction solution at low temperature, a method in which an acid is added after the addition of water, to adjust the pH of the aqueous layer to a neutral pH, a method in which the reaction solution is added to an acidic aqueous solution, or the like may be employed. It is preferred to add an acid after the addition of water to adjust the pH of the aqueous layer to a neutral pH. After the removal of the inorganic salt, depending on the purity, the solvent may be simply removed by concentration, or purification on a column may be carried out.

Examples of the water-insoluble solvent used for the extraction in the post-treatment include ketones such as 2-butanone, methylisobutyl ketone, and cyclohexanone; aromatic hydrocarbons such as benzene, toluene, xylene, chlorobenzene, and trifluoromethylbenzene; aliphatic hydrocarbons such as n-pentane, n-hexane, n-heptane, and cyclohexane; esters such as methyl acetate, ethyl acetate, isopropyl acetate, and butyl acetate; ethers such as diethyl ether, di-n-propyl ether, diisopropyl ether, di-n-butyl ether, methyl isopropyl ether, methyl-tert-butyl ether, ethyl-tert-butyl ether, and cyclopentyl methyl ether; and halogenated hydrocarbons such as dichloromethane, chloroform, carbon tetrachloride, and 1,2-dichloroethane.

Among these, toluene, xylene, diisopropyl ether, di-n-butyl ether, methyl isopropyl ether, and methyl-tert-butyl ether are preferred since the compound represented by General Formula (2) shows high solubility in these solvents. From the viewpoint of the cost, toluene is more preferred.

By the steps (viii) to (x), the compound represented by General Formula (2), which is the starting substance, can be produced.

By the step (xi) described below, the compound represented by General Formula (2) can be produced by a method different from (viii) to (x).

<Step (xi)>

The step (xi) is a step of allowing an alkylating agent to act on a compound represented by General Formula (9):

(wherein each $R^1$ independently represents a $C_1$-$C_{10}$ alkyl group which is optionally substituted, a $C_7$-$C_{20}$ aralkyl group which is optionally substituted, or a $C_6$-$C_{12}$ aryl group which is optionally substituted)
in the presence of a base, to obtain a compound represented by General Formula (2):

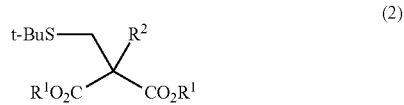

(wherein $R^1$ has the same meaning as $R^1$ in the General Formula (9), and $R^2$ represents a $C_1$-$C_4$ alkyl group).

The compound represented by General Formula (9) can be obtained by, for example, allowing tert-butyl mercaptan to act on dialkyl methylene malonate synthesized by the method described in WO 2010/129066 or Organic synthesis, 1958, 38, 22.

The $R^1$ and the $R^2$ in the compound represented by the General Formula (9) are the same as those described in the step (i).

Thus, specific examples of the compound represented by General Formula (9) include the following compounds.

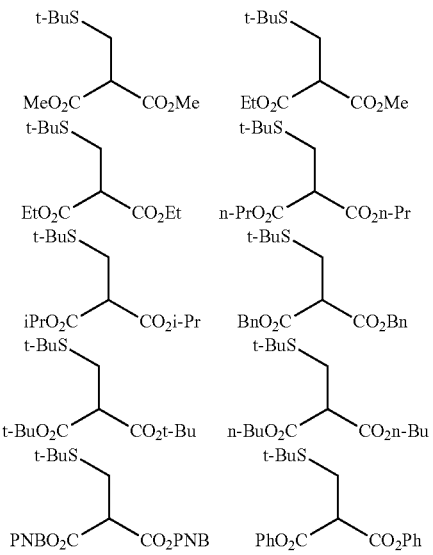

Among the compounds mentioned above, the following compounds are preferred as the compound represented by the General Formula (9).

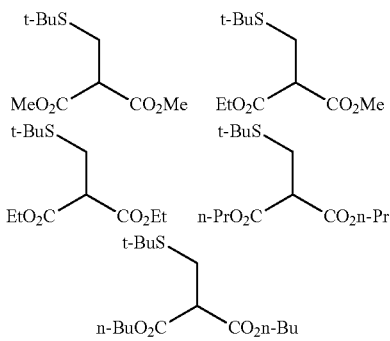

In the compound represented by General Formula (9), the $R^1$s are not necessarily the same, and may be different from each other. In cases where the $R^1$s are different from each other, two enantiomers, the (R)-isomer and the (S)-isomer, are present as the compound represented by the General Formula (9). The mixing ratio between these enantiomers is not limited.

Examples of the alkylating agent which may be used include $R^2Y$ and $(R^2O)_2SO_2$ (wherein $R^2$ has the same meaning as in the General Formula (2); and Y represents a halogen atom, or a $C_6$-$C_{12}$ arylsulfonyloxy group, $C_1$-$C_{10}$ alkylsulfonyloxy group, or $C_7$-$C_{20}$ aralkylsulfonyloxy group, which is optionally substituted).

Examples of the halogen atom of Y include a chlorine atom, bromine atom, and iodine atom. Examples of the $C_6$-$C_{12}$ arylsulfonyloxy group include benzenesulfonyloxy, 1-naphthalenesulfonyloxy, and 2-naphthalenesulfonyloxy. Examples of the $C_1$-$C_{10}$ alkylsulfonyloxy group include methanesulfonyloxy, ethanesulfonyloxy, and propanesulfonyloxy. Examples of the $C_7$-$C_{20}$ aralkylsulfonyloxy group include benzylsulfonyloxy. Examples of substituents which may be contained in the arylsulfonyloxy group, alkylsulfonyloxy group, or aralkylsulfonyloxy group include $C_1$-$C_6$ alkyl groups such as methyl and ethyl; $C_1$-$C_6$ alkoxy groups such as methoxy and ethoxy; halogen atoms such as a fluorine atom, chlorine atom, bromine atom, and iodine atom; and nitro. The number of substituents is not limited, and, in cases where there are two or more substituents, the substituents may be of the same type or different types.

As $R^2$, a chlorine atom, bromine atom, iodine atom, methanesulfonyloxy, trifluoromethanesulfonyloxy, or 4-toluenesulfonyloxy is preferred. Among these, a bromine atom, iodine atom, methanesulfonyloxy, or p-toluenesulfonyloxy is preferred because of their high reactivity. A bromine atom is more preferred.

The amount of the alkylating agent used may be appropriately set within the range of, for example, 0.7 molar equivalent to 10 molar equivalents with respect to the amount of the compound represented by General Formula (9). In order to allow the reaction to proceed quickly and to thereby suppress side reactions, the amount of the agent is preferably slightly excessive. Thus, the amount is preferably 1.0 molar equivalent to 3.0 molar equivalents. From the viewpoints of the cost, and of the fact that side reactions easily proceed in cases where the amount of the agent is too excessive, the amount of the agent is more preferably 1.1 molar equivalents to 2.0 molar equivalents.

Examples of the base include alkali metal alkoxides and alkali metal hydrides. Examples of the alkali metal alkoxides include lithium ethoxide, lithium methoxide, lithium tert-butoxide, sodium ethoxide, sodium methoxide, sodium tert-butoxide, potassium ethoxide, potassium methoxide, and potassium tert-butoxide. Examples of the alkali metal hydrides include lithium hydride, sodium hydride, and potassium hydride.

The compound represented by General Formula (9) repeats elimination and addition of a tert-butylthio group in the presence of a base. Occurrence of the elimination results in conversion of the General Formula (9) to dialkyl methylene malonate. In cases where a nucleophilic base is present in this process, Michael addition reaction to the dialkyl methylene malonate may occur, leading to a decrease in the yield. On the other hand, bases having no nucleophilicity do not cause such a side reaction. Thus, the base is preferably an alkali metal hydride such as lithium hydride, sodium hydride, or potassium hydride, which does not have nucleophilicity. The base is more preferably sodium hydride from the viewpoint of the cost and safety.

The amount of the base used may be appropriately set within the range of, for example, 0.7 molar equivalent to 10 molar equivalents with respect to the amount of the compound represented by General Formula (9). Since partial inactivation tends to occur due to water in the solvent or the like, the amount is preferably 0.9 molar equivalent to 4.0 molar equivalents. From the viewpoint of the cost and suppression of side reactions, the amount is more preferably 1.0 molar equivalent to 2.0 molar equivalents.

Examples of the reaction solvent include aromatic hydrocarbons such as benzene, toluene, xylene, chlorobenzene, and trifluoromethylbenzene; aliphatic hydrocarbons such as n-pentane, n-hexane, n-heptane, and cyclohexane; ethers such as diethyl ether, di-n-propyl ether, di-n-butyl ether, methyl isopropyl ether, methyl-tert-butyl ether, ethyl-tert-butyl ether, cyclopentyl methyl ether, tetrahydrofuran, dioxane, and 1,2-dimethoxyethane; amides such as N,N-dimethylformamide and N,N-dimethylacetamide; halogenated hydrocarbons such as dichloromethane, chloroform, carbon tetrachloride, and 1,2-dichloroethane; and dimethylsulfoxide.

Among these, aprotic polar solvents such tetrahydrofuran, dioxane, 1,2-dimethoxyethane, N,N-dimethylformamide, N,N-dimethylacetamide, and dimethylsulfoxide are preferred since the salt produced by the reaction between the compound represented by General Formula (9) and the base is highly soluble in these solvents, and the solvents therefore have an effect to promote the reaction. Tetrahydrofuran is more preferred since it has a low boiling point and can be easily removed by concentration.

The amount of the reaction solvent used may be appropriately set within the range of, for example, 0 volume to 100 volumes with respect to the amount of the compound represented by General Formula (9). Depending on the type of the base, the amount of heat of the reaction is large, and it is risky to carry out the reaction without suspension in a solvent. Because of this, and from the viewpoint of the volume efficiency, the amount of the reaction solvent is preferably 1 volume to 30 volumes, more preferably 8 volumes to 20 volumes.

The reaction temperature may be appropriately set within the range of, for example, −100° C. to 200° C. The reaction temperature is preferably −50° C. to 100° C. In cases where the reaction temperature is too low, the solubility of the salt composed of the compound represented by General Formula (9) and the base in the reaction solvent decreases, leading to a decrease in the reaction rate, while in cases where the reaction temperature is too high, side reactions such as generation of a dimer may occur. Therefore, the reaction temperature is more preferably −10° C. to 50° C.

The reaction time may be appropriately set within the range of, for example, 0 hour to 30 hours. The reaction time is preferably 5 minutes to 5 hours. Since, in case where the reaction time is too long, side reactions may occur, the reaction time is more preferably 15 minutes to 2 hours.

As a post-treatment after this reaction, the inorganic salt precipitated in the reaction solution is preferably removed by filtration or washing with water. Since, depending on the solvent used, the inorganic salt is dissolved in the reaction solvent, washing water is more preferably included. When water is added to the reaction solution, the aqueous layer becomes basic. In order to suppress hydrolysis of the ester group in the compound represented by General Formula (8) or General Formula (9), a method in which acidic water is added to the reaction solution at low temperature, a method in which an acid is added after the addition of water, to adjust the pH of the aqueous layer to a neutral pH, a method in which the reaction solution is added to an acidic aqueous solution, or the like may be employed. It is preferred to add an acid after the addition of water, to adjust the pH of the aqueous layer to a neutral pH. After the removal of the inorganic salt, depending on the purity, the solvent may be simply removed by concentration, or purification on a column may be carried out.

In the washing with water in the post-treatment of this step, examples of the water-insoluble solvent which may be used for the extraction include ketones such as 2-butanone, methylisobutyl ketone, and cyclohexanone; aromatic hydrocarbons such as benzene, toluene, xylene, chlorobenzene, and trifluoromethylbenzene; aliphatic hydrocarbons such as n-pentane, n-hexane, n-heptane, and cyclohexane; esters such as methyl acetate, ethyl acetate, isopropyl acetate, and butyl acetate; ethers such as diethyl ether, di-n-propyl ether, diisopropyl ether, di-n-butyl ether, methyl isopropyl ether, methyl-tert-butyl ether, ethyl-tert-butyl ether, and cyclopentyl methyl ether; and halogenated hydrocarbons such as dichloromethane, chloroform, carbon tetrachloride, and 1,2-dichloroethane.

Among these, n-pentane, n-hexane, n-heptane, cyclohexane, diethyl ether, di-n-propyl ether, diisopropyl ether, di-n-butyl ether, methyl isopropyl ether, methyl-tert-butyl ether, ethyl-tert-butyl ether, and dichloromethane are preferred since these have low boiling points, and show high removal efficiencies. Diethyl ether, di-n-propyl ether, diisopropyl ether, di-n-butyl ether, methyl isopropyl ether, methyl-tert-butyl ether, and ethyl-tert-butyl ether are more preferred since they show high extraction efficiencies.

[Novel Compounds]

By the present invention, the following novel compounds can be provided.

The novel compounds of the present invention can be produced by the production methods of the present invention, and can also be synthesized using ordinary techniques of organic chemistry.

Specific examples of $R^1$, $R^2$, and $R^3$ in the following General Formulae (4-1), (5), (6), and (7S), and specific examples of the compounds represented by General Formulae (4-1), (5), (6), and (7S) are the same as those described in the [Method for Producing α-Substituted Cysteine Represented by General Formula (1) or Salt Thereof] and the [Method for Producing α-Substituted Cysteine Represented by General Formula (1S) or Salt Thereof] mentioned above.

A compound represented by General Formula (4-1):

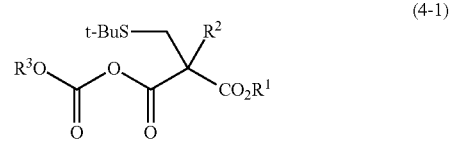

(wherein $R^1$ and $R^3$ each independently represent a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ represents a $C_1$-$C_4$ alkyl group).

A compound represented by General Formula (5):

(wherein $R^1$ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ represents a $C_1$-$C_4$ alkyl group).

<Compound Represented by General Formula (6)>
A compound represented by General Formula (6):

(wherein $R^1$ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ represents a $C_1$-$C_4$ alkyl group).

<Compound Represented by General Formula (7S)>
A compound represented by General Formula (7S):

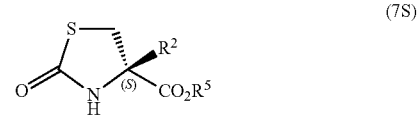

(wherein $R^2$ represents a $C_1$-$C_4$ alkyl group, and $R^5$ represents a hydrogen atom, or a $C_1$-$C_{10}$ alkyl group which is optionally substituted, a $C_7$-$C_{20}$ aralkyl group which is optionally substituted, or a $C_6$-$C_{12}$ aryl group which is optionally substituted).

EXAMPLES

The present invention is described in more detail by way of Examples. However, the present invention is not limited thereto.

In the present Examples, quantitative analysis was carried out by GC (Gas Chromatography) or HPLC (High Performance Liquid Chromatography) under the following conditions.

\<GC-1\>

Column: GL Science TC-5 (0.53 mm×300 mm; film thickness, 5 μm)

Carrier gas: helium; column flow, 3.93 mL/minute (split ratio, 20:1); inlet pressure, 22.2 kPa; total flow, 85.4 mL/minute (linear velocity, 30 cm/second)

Column Temperature: 50° C. (kept for 5 minutes)→heating at 10° C./minute→200° C. (kept for 10 minutes)

Injection temperature: 220° C.

Detection temperature: 230° C.

Detector: FID; hydrogen, 40 mL/minute; air, 400 mL/minute; make-up gas, nitrogen, 30 mL/minute; signal attenuation, ×2-3

Sample injection volume: 1.0 μL

\<HPLC-1\>

Column: Nacalai Tesque, COSMOSIL 5C18-MSII (4.6 mm×250 mm, particle size, 5 μm)

Mobile phase: 50 mmol/L aqueous tetrafluoroacetic acid solution/acetonitrile=30/70 (volume ratio)

Flow rate: 1.0 mL/minute

Column temperature: 35° C.

Detection wavelength: UV 220 nm

\<HPLC-2\>

Column: DAICEL, CHIRALPAK OZ-3R (4.6 mm×150 mm)

Mobile phase: 0.02 wt % aqueous tetrafluoroacetic acid solution/acetonitrile=75/25 (volume ratio)

Flow rate: 0.7 mL/minute

Column temperature: 30° C.

Detection wavelength: UV 220 nm

\<HPLC-3\>

Column: SIELC, primesep 100 (4.6 mm×150 mm, particle size, 5 μm)

Mobile phase: A, 0.1 wt % aqueous tetrafluoroacetic acid solution; B, acetonitrile Gradient (B concentration): 10% at Minute 0→30% at Minute 15→80% at Minute 20

Flow rate: 1.0 mL/minute

Column temperature: 40° C.

Detection wavelength: UV 210 nm

\<HPLC-4\>

Column: Shiseido, Chiral CD-Ph (4.6 mm×250 mm, particle size, 5 μm)

Mobile phase: aqueous (100 mmol/L perchloric acid+0.2 wt % phosphoric acid) solution/acetonitrile=99/1 (volume ratio)

Flow rate: 0.5 mL/minute

Column temperature: 30° C.

Detection wavelength: UV 205 nm

Example 1

Step (viii): Production of tert-Butylthiomethanol

Under nitrogen gas flow, 240 g (2.66 mol) of tert-butyl mercaptan and 216 g (2.66 mol) of formalin (37 wt %) were placed in a 1-L reactor at room temperature, and the resulting mixture was stirred. After allowing the reaction to proceed at 60° C. for 9 hours, separation extraction was carried out by adding 160 g of cyclohexane while keeping the reactor at a temperature within the range of 50° C. to 60° C., followed by removing the aqueous phase. Thereafter, cyclohexane was removed by concentrating the cyclohexane layer under reduced pressure. The resulting crude tert-butylthiomethanol was subjected to distillation under reduced pressure at 70° C./2.0 kPa to obtain 208 g (1.73 mmol; yield, 65.0%) of tert-butylthiomethanol. As a result of GC analysis under \<GC-1\>, its purity was found to be 99% by area. The measurement results obtained were as follows.

$^1$H-NMR (400 MHz, CDCl$_3$) δ 1.41 (9H, s), 2.11 ($^1$H, t, J=6.4 Hz), 4.83 (2H, d, J=6.4 Hz).

Example 2

Step (ix): Production of tert-Butylthiochloromethane

Under nitrogen gas flow, 190 g (1.58 mol) of tert-butylthiomethanol produced in Example 1 and 1.44 kg of cyclohexane were placed in a 3-L reactor at room temperature. To the resulting mixture, 150 g (1.90 mol) of pyridine was added while the inner temperature was kept at 0° C. To the mixture, 226 g (1.89 mol) of thionyl chloride was then added dropwise while the inner temperature was kept at −2° C. to 6° C. After stirring the resulting mixture at a temperature within the range of −4° C. to 0° C. for 1 hour, 380 g of cyclohexane was added thereto, and the precipitated salt was removed by filtration. Cyclohexane was removed by concentrating the obtained filtrate by distillation, and the resulting crude tert-butylthiochloromethane was subjected to distillation under reduced pressure at 57° C./3.0 kPa to obtain 140 g (1.01 mol; yield, 63.9%) of tert-butylthiochloromethane. As a result of GC analysis under \<GC-1\>, its purity was found to be 98% by area. The measurement results obtained were as follows.

$^1$H-NMR (400 MHz, CDCl$_3$) δ 1.42 (9H, s), 4.86 (2H, s)

Example 3

Step (x): Production of Diethyl 2-[(tert-Butylthio) methyl]-2-methylmalonate

Under nitrogen gas flow, 107 g (0.953 mol) of potassium-tert-butoxide and 790 g of tetrahydrofuran were placed in a 3-L reactor. To the resulting mixture, 158 g (0.907 mol) of diethyl methylmalonate was added dropwise at an inner temperature within the range of 18° C. to 26° C. for 30 minutes. After stirring the resulting mixture for 30 minutes, 132 g (0.953 mol) of tert-butylthiochloromethane produced in Example 2 was added dropwise thereto for 1 hour while the inner temperature was kept within the range of 18° C. to 26° C. After stirring the resulting mixture for 3 hours, 395 g of toluene and 395 g (0.229 mol) of 2 wt % hydrochloric acid were added thereto, followed by stirring the resulting mixture for 30 minutes. The aqueous layer was then removed by separation. Subsequently, an operation of adding 395 g of water to the toluene layer, stirring the resulting mixture for 1 hour, and then removing the aqueous layer by separation was repeated twice. Toluene was removed by concentrating the toluene layer by distillation. Thereafter, an operation of adding 250 g of ethanol to the resulting crude diethyl 2-[(tert-butylthio)methyl]-2-methylmalonate, stirring the resulting mixture, and then removing the solvent by distillation was repeated twice. As a result, 246 g (0.848 mol; yield, 93.5%) of diethyl 2-[(tert-butylthio)methyl]-2-methylmalonate was obtained. As a result of GC analysis under \<GC-1\>, its GC purity was found to be 95.2% by area. The measurement results obtained were as follows.

$^1$H-NMR (400 MHz, CDCl$_3$) δ 1.26 (6H, t, J=7.1 Hz), 1.31 (9H, s), 1.48 (3H, S), 3.03 (2H, s), 4.20 (4H, q, J=7.1 Hz)

Reference Example 1

Production of Diethyl 2-[(tert-Butylthio)methyl]malonate

Under nitrogen gas flow, 706 mg (23.5 mmol) of paraformaldehyde, 628 mg (3.15 mmol) of copper(I) acetate monohydrate, 1.32 g (22.0 mmol) of acetic acid, 6.67 mL of toluene, and 3.00 g (18.7 mmol) of diethyl malonate were placed in a 100-mL three-necked flask, and a Dean-Stark tube was attached to the flask, followed by stirring the resulting mixture at 110° C. for 6 hours. The reaction solution was allowed to cool to room temperature, and 4 mL of toluene was added thereto, followed by washing the organic layer twice with 10 mL of water and once with 10 mL of saturated aqueous sodium chloride solution. To the resulting solution, 1.00 mL (8.88 mmol) of tert-butyl mercaptan and 1.30 mL (9.33 mmol) of triethylamine were added, and the resulting mixture was stirred at 25° C. for 1.5 hours. This reaction solution was washed twice with 6 mL of saturated aqueous ammonium chloride solution, and once with 10 mL of saturated aqueous sodium chloride solution. The obtained toluene layer was dried over anhydrous sodium sulfate, and sodium sulfate was removed by filtration. After removing toluene by concentrating the filtrate by distillation, the obtained crude diethyl 2-[(tert-butylthio)methyl]malonate was purified by silica gel chromatography, to obtain 1.32 g (5.02 mmol; yield, 26.8%) of diethyl 2-[(tert-butylthio)methyl]malonate. The measurement results obtained were as follows.

$^1$H-NMR (400 MHz, CDCl$_3$) δ 1.28 (6H, t, J=7.1 Hz), 1.33 (9H, s), 3.03 (2H, d, J=7.8 Hz), 3.51 (1H, t, J=7.8 Hz), 4.17-4.28 (4H, m)

Example 4

Step (xi): Production of Diethyl 2-[(tert-Butylthio)methyl]-2-methylmalonate Under nitrogen gas flow, 3.50 mL of tetrahydrofuran and 0.160 g (4.00 mmol) of 60 wt % sodium hydride were placed in a 50-mL three-necked flask, and the flask was cooled on ice. To the resulting mixture, a mixed solution of 0.700 g (2.67 mmol) of diethyl 2-[(tert-butylthio)methyl]malonate produced in Reference Example 1 and 3.50 mL of tetrahydrofuran was added dropwise. The resulting mixture was stirred for 10 minutes, and a mixed solution of 0.183 mL (2.94 mmol) of methyl iodide and 2.00 mL of tetrahydrofuran was added dropwise to the mixture for 15 minutes. To the resulting mixture, 0.0410 mL (0.659 mmol) of methyl iodide was added dropwise twice, and the resulting mixture was stirred for 20 minutes. After adding 3.5 mL of water thereto, extraction was performed twice with 7.0 mL of tert-butyl methyl ether. The resulting layers of tert-butyl methyl ether were combined, and washed with 3.5 mL of saturated brine, followed by separation. The obtained tert-butyl methyl ether layer was concentrated to obtain 0.710 g of a colorless oily product. As a result of $^1$H-NMR analysis, this oily product was found to contain 0.646 g (2.34 mmol; yield, 87.6%) of diethyl 2-[(tert-butylthio)methyl]-2-methylmalonate.

Example 5

Step (i): Production of Ethyl 2-[(tert-Butylthio)methyl]-2-methylmalonate

Under nitrogen gas flow, 4.20 g (15.2 mmol) of diethyl 2-[(tert-butylthio)methyl]-2-methylmalonate and 25 mL of ethanol were placed in a 100-mL recovery flask, and the flask was cooled to 2° C. At an inner temperature within the range of 2° C. to 5° C., 16.0 mL (16.0 mmol) of 1 mol/L aqueous sodium hydroxide solution was added dropwise thereto for 10 minutes. The resulting mixture was stirred at 22° C. for 3 hours, and ethanol was then removed by distillation. The obtained reaction solution was washed twice with 4.2 mL of toluene. To the aqueous layer, 17 mL of 1 mol/L hydrochloric acid was added to adjust the pH to 1, and extraction was then performed 3 times with 4.2 mL of toluene. The resulting toluene layers were combined, and dried over 4.20 g of anhydrous sodium sulfate, followed by removing sodium sulfate by filtration. Toluene was removed by concentrating the filtrate by distillation, and the obtained crude ethyl 2-[(tert-butylthio)methyl]-2-methylmalonate was purified by silica gel chromatography, to obtain 3.26 g of a colorless oily product. As a result of $^1$H-NMR analysis, this oily product was found to contain 3.16 g (12.7 mmol; yield, 83.5%) of ethyl 2-[(tert-butylthio)methyl]-2-methylmalonate. The measurement results obtained were as follows.

$^1$H-NMR (400 MHz, CDCl$_3$) δ 1.29 (3H, t, J=7.1 Hz), 1.31 (9H, s), 1.54 (3H, s), 3.02 (1H, d, J=11.9 Hz), 3.08 (1H, d, J=11.9 Hz), 4.24 (2H, q, J=7.1 Hz)

Example 6

Step (ii): Production of Ethyl 2-[(tert-Butylthio)methyl]-3-[(ethoxycarbonyl)oxy]-2-methyl-3-oxopropanoate Under nitrogen gas flow, 2.21 g (8.90 mmol) of ethyl 2-[(tert-butylthio)methyl]-2-methylmalonate produced in Example 5 and 28 mL of toluene were placed in a 200-mL four-necked flask, and the flask was cooled to 0° C. To the resulting mixture, 1.36 mL (9.76 mmol) of triethylamine was added dropwise for 2 minutes at an inner temperature within the range of 1° C. to 8° C. Subsequently, 932 µL (9.79 mmol) of ethyl chloroformate was added dropwise thereto for 4 minutes at an inner temperature within the range of 1° C. to 8° C., and the resulting mixture was stirred at an inner temperature of 0° C. for 1 hour. As a result of $^1$H-NMR analysis, this reaction solution was found to contain ethyl 2-[(tert-butylthio)methyl]-3-[(ethoxycarbonyl)oxy]-2-methyl-3-oxopropanoate. The measurement results obtained were as follows.

$^1$H-NMR (400 MHz, CDCl$_3$) δ 1.28 (3H, t, J=7.1 Hz), 1.32 (9H, s), 1.35 (3H, t, J=7.1 Hz), 1.55 (3H, s), 3.03 (1H, d, J=12.1 Hz), 3.09 (1H, d, J=12.1 Hz), 4.24 (2H, q, J=7.1 Hz), 4.32 (2H, q, J=7.1 Hz)

Example 7

Step (iii): Production of Ethyl 2-(Azidocarbonyl)-2-[(tert-butylthio)methyl]propanoate The solution containing ethyl 2-[(tert-butylthio)methyl]-3-[(ethoxycarbonyl)oxy]-2-methyl-3-oxopropanoate in toluene, produced in Example 6 was cooled to 0° C., and an aqueous solution prepared by mixing 908 mg (10.7 mmol) of sodium azide with 4.4 mL of water was added to the above solution at an inner temperature within the range of 0° C. to 3° C., followed by stirring the resulting mixture at an inner temperature of 0° C. for 6 hours. Subsequently, the aqueous layer was removed, and the obtained toluene layer was washed with 10 mL of saturated aqueous sodium hydrogen carbonate solution, 10 mL of saturated aqueous ammonium chloride solution, and 10 mL of saturated brine. The resulting toluene layers were combined, and dried over anhydrous sodium sulfate, followed by removing sodium sulfate by separation. As a result of $^1$H-NMR analysis, this solution was found to contain ethyl 2-(azidocarbonyl)-2-[(tert-butylthio)methyl]propanoate. The measurement results obtained were as follows.

$^1$H-NMR (400 MHz, CDCl$_3$) δ 1.29 (3H, t, J=7.1 Hz), 1.31 (9H, s), 1.54 (3H, s), 3.02 (1H, d, J=11.9 Hz), 3.08 (1H, d, J=11.9 Hz), 4.24 (2H, q, J=7.1 Hz)

Example 8

Step (iv): Production of Ethyl 2-[(tert-Butylthio)methyl]-2-isocyanatopropanoate Under nitrogen gas flow, the solution containing ethyl 2-(azidocarbonyl)-2-[(tert-butylthio)methyl]propanoate in toluene, produced in Example 7 was placed in a 300-mL four-necked flask, and the solution was then stirred at an inner temperature within the range of 75° C. to 80° C. for 3 hours, to obtain 23.1 g of a solution of ethyl 2-[(tert-butylthio)methyl]-2-isocyanatopropanoate in toluene. As a result of $^1$H-NMR analysis, the content of ethyl 2-[(tert-butylthio)methyl]-2-isocyanatopropanoate in this solution was found to be 1.65 g (6.72 mmol; yield, 75.5% from ethyl 2-[(tert-butylthio)methyl]-2-methylmalonate). The measurement results obtained were as follows.

$^1$H-NMR (400 MHz, CDCl$_3$) δ 1.29 (3H, t, J=7.1 Hz), 1.30 (9H, s), 1.52 (3H, s), 2.78 (1H, d, J=12.1 Hz), 2.98 (1H, d, J=12.1 Hz), 4.23 (2H, q, J=7.1 Hz)

Example 9

Step (vi-1): Production of Ethyl 4-Methyl-2-oxo-1,3-thiazolidine-4-carboxylate

To 6.01 g of the solution containing 353 mg (1.44 mmol) of ethyl 2-[(tert-butylthio)methyl]-2-isocyanatopropanoate in toluene, produced in Example 8, 288 mg (1.51 mmol) of p-toluenesulfonic acid monohydrate dissolved in 1.30 mL of acetone was added, and the resulting mixture was stirred at an inner temperature of 20° C. for 2.5 hours. Subsequently, the solvent was concentrated, and 1.4 mL of water was added thereto. The pH was adjusted to 7 by addition of 1 mol/L aqueous sodium hydroxide solution. After carrying out extraction 4 times with 1.1 mL of toluene and twice with 1.1 mL of tert-butyl methyl ether, the resulting organic layers were combined and concentrated, to obtain a pale yellow oily product. As a result of $^1$H-NMR analysis, this oily product was found to contain ethyl 4-methyl-2-oxo-1,3-thiazolidine-4-carboxylate. The measurement results obtained were as follows.

$^1$H-NMR (400 MHz, CDCl$_3$) δ 1.32 (3H, t, J=7.1 Hz), 1.61 (3H, s), 3.30 (1H, d, J=11.4 Hz), 3.82 (1H, d, J=11.4 Hz), 4.27 (2H, q, J=7.1 Hz)

Example 10

Step (vi-2) and Step (vii): Production of 4-Methyl-2-oxo-1,3-thiazolidine-4-carboxylic Acid and α-Methylcysteine Hydrochloride Under nitrogen gas flow, the oily product containing ethyl 4-methyl-2-oxo-1,3-thiazolidine-4-carboxylate produced in Example 9 was placed in a 50-mL recovery flask, and 9.4 mL (56 mmol) of 6 mol/L hydrochloric acid was added thereto, followed by stirring the resulting mixture at an inner temperature of 100° C. for 10 hours. As a result of $^1$H-NMR analysis of this reaction solution, the reaction solution was found to contain 4-methyl-2-oxo-1,3-thiazolidine-4-carboxylic acid.

$^1$H-NMR (400 MHz, D$_2$O) δ 1.52 (3H, s), 3.40 (1H, d, J=11.6 Hz), 3.69 (1H, d, J=11.6 Hz)

Subsequently, this reaction solution was stirred at an inner temperature of 100° C. for additional 30 hours. As a result of $^1$H-NMR analysis of this reaction solution, the reaction solution was found to contain α-methylcysteine hydrochloride. The measurement results obtained were as follows.

$^1$H-NMR (400 MHz, D$_2$O) δ 1.53 (3H, s), 2.84 (1H, d, J=15.0 Hz), 3.11 (1H, d, J=15.0 Hz)

Example 11

Cloning of Hydrolase Genes for Step (i)

Based on a gene sequence (cenp, SEQ ID NO:1) encoding carboxyesterase NP (CENP, GenBank Accession No. AAC43262, SEQ ID NO:2), which is a hydrolase derived from the *Bacillus subtilis* Thail-8 strain, primers for amplifying the entire cenp gene, npfw (SEQ ID NO:19) and npry (SEQ ID NO:20) were designed and synthesized. PCR was carried out according to a conventional method using, as a template, chromosomal DNA of each of the *Bacillus subtilis* NBRC3108 strain, *Bacillus subtilis* NBRC3215 strain, *Bacillus subtilis* NBRC3335 strain, *Bacillus subtilis* NBRC14144 strain, *Bacillus subtilis* NBRC14191 strain, *Bacillus subtilis* NBRC14473 strain, *Bacillus subtilis* NBRC101246 strain, and *Bacillus subtilis* NBRC101590 strain, and the primers npfw (SEQ ID NO:19) and npry (SEQ ID NO:20). As a result, a total of eight kinds of DNA fragments each having a length of about 1.0 kbp were obtained.

Each of the eight kinds of DNA fragments obtained was digested with EcoRI and XbaI. According to a conventional method, each of the resulting DNA fragments was introduced downstream of the trc promoter of MunI/XbaI-digested pKW32, which is a plasmid described in PCT/JP2011/069680, to obtain plasmids pKCENP1, pKCENP2, pKCENP3, pKCENP4, pKCENP5, pKCENP6, pKCENP7, and pKCENP8.

The sequence of the hydrolase gene inserted in each of the total of eight kinds of plasmids obtained was identified according to a conventional method. The gene sequences were cenp-1 (SEQ ID NO:3), cenp-2 (SEQ ID NO:5), cenp-3 (SEQ ID NO:7), cenp-4 (SEQ ID NO:9), cenp-5 (SEQ ID NO:11), cenp-6 (SEQ ID NO:13), cenp-7 (SEQ ID NO:15), and cenp-8 (SEQ ID NO:17), respectively. The amino acid sequences of the hydrolases encoded by the genes were CENP-1 (SEQ ID NO:4), CENP-2 (SEQ ID NO:6), CENP-3 (SEQ ID NO:8), CENP-4 (SEQ ID NO:10), CENP-5 (SEQ ID NO:12), CENP-6 (SEQ ID NO:14), CENP-7 (SEQ ID NO:16), and CENP-8 (SEQ ID NO:18), respectively.

Using the eight kinds of plasmids obtained, *E. coli* JM109 (manufactured by Takara Bio Inc.) was transformed according to a conventional method, to obtain recombinant *E. coli* JM109/pKCENP1, JM109/pKCENP2, JM109/pKCENP3, JM109/pKCENP4, JM109/pKCENP5, JM109/pKCENP6, JM109/pKCENP7, and JM109/pKCENP8. In order to obtain bacterial cells expressing these genes, each recombinant *E. coli* was cultured in liquid LB medium supplemented with kanamycin and a lac promoter inducer at 30° C. The cells were collected after about 20 hours of the culture.

Among the hydrolases obtained, homology between the amino acid sequence CENP-1 (SEQ ID NO:4) and each of the other amino acid sequences (SEQ ID NO:6, SEQ ID NO:8, SEQ ID NO:10, SEQ ID NO:12, SEQ ID NO:14, SEQ ID NO:16, SEQ ID NO:18) was calculated using BLAST. The results are shown in Table 1.

Homology between the hydrolase amino acid sequence CENP-1 (SEQ ID NO:4) and the amino acid sequence of each of commercially available enzymes, *Bacillus licheniformis*-derived protease (commercially available enzyme, manufactured by Sigma-Aldrich) and pig liver-derived esterase (commercially available enzyme, manufactured by Sigma-Aldrich), was investigated by searching by BLAST. As a result, no homology was found.

TABLE 1

| Amino acid sequence of hydrolase | SEQ ID NO | Homology to *Bacillus subtilis* IFO3108-derived carboxyesterase NP (SEQ ID NO: 4) |
|---|---|---|
| CENP-1 | 4 | 100% |
| CENP-2 | 6 | 99% |
| CENP-3 | 8 | 99% |
| CENP-4 | 10 | 99% |
| CENP-5 | 12 | 99% |
| CENP-6 | 14 | 99% |
| CENP-7 | 16 | 99% |
| CENP-8 | 18 | 99% |

Example 12

Screening for Hydrolase for Step (i)

In an aqueous solution containing 100 mmol/L potassium phosphate, cells of each of the eight kinds of bacteria obtained in Example 11 and 30 g/L diethyl 2-[(tert-butylthio)methyl]-2-methylmalonate were mixed, and the reaction was allowed to proceed at 30° C. at pH 7 overnight with shaking. *Bacillus licheniformis*-derived protease (manufactured by Sigma-Aldrich) was also allowed to react under the same conditions overnight with shaking.

To 200 μL of each solution after the reaction, 100 μL of 1 mol/L hydrochloric acid was added to stop the reaction, and the reaction solution was then centrifuged at 10,000 rpm. After mixing 50 μL of the supernatant obtained after the centrifugation with 50 vol % acetonitrile and 950 μL of 50 mmol/L trifluoroacetic acid solution, the optical purity was analyzed under the conditions of <HPLC-2>.

Bacterial cells of each of commercially available enzymes, *Bacillus stearothermophilus*-derived esterase BS1 (manufactured by Julich Fine Chemicals), *Bacillus stearothermophilus*-derived esterase BS3 (manufactured by Julich Fine Chemicals), or pig liver-derived esterase (manufactured by Sigma-Aldrich), were allowed to react with 5 g/L diethyl 2-[(tert-butylthio)methyl]-2-methylmalonate in an aqueous solution containing 100 mmol/L potassium phosphate at 30° C. at pH 7 overnight with shaking. To 250 μL of the solution after the reaction, 250 μL of acetonitrile was added, and the resulting mixture was centrifuged at 10,000 rpm. The resulting centrifugation supernatant was analyzed under the conditions of <HPLC-2>, to investigate the optical purity of the ethyl 2-[(tert-butylthio)methyl]-2-methylmalonate produced.

Figure 2:
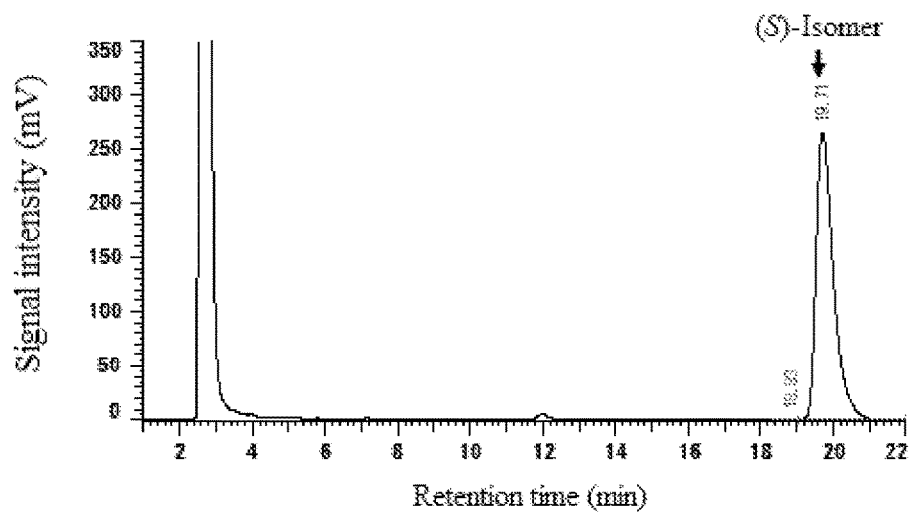
FIG. 2 shows the result of HPLC analysis of the optical purity of the reaction product obtained by allowing an enzyme derived from the Bacillus subtilis IFO3108 strain to act on diethyl 2-(tert-butylthio)methyl-2-methylmalonate (Example 12). The upper panel shows the result of the reaction with the enzyme derived from the Bacillus subtilis IFO3108 strain, and the lower panel shows the result of analysis of the optical purity of a racemic sample which was carried out as a control experiment.
Figure 2:
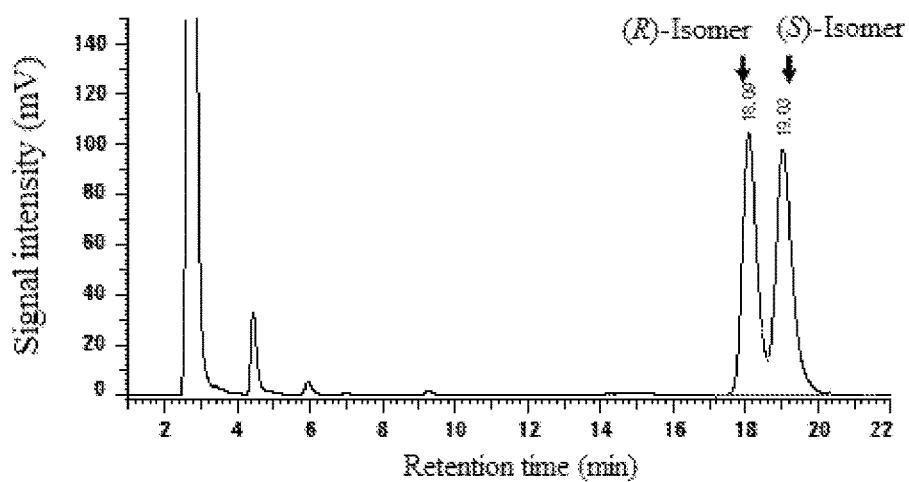

These results are shown in Table 2 and FIG. 2.

TABLE 2

| Name of recombinant *E. coli* or enzyme | Optical purity of (S)-isomer ee (%) |
|---|---|
| JM109/pKCENP1 | 99.8 |
| JM109/pKCENP2 | 99.7 |
| JM109/pKCENP3 | 99.7 |
| JM109/pKCENP4 | 99.8 |
| JM109/pKCENP5 | 99.8 |
| JM109/pKCENP6 | 99.8 |
| JM109/pKCENP7 | 99.6 |
| JM109/pKCENP8 | 99.8 |
| *Bacillus licheniformis*-derived protease (commercially available enzyme, manufactured by Sigma-Aldrich) | 94.5 |
| *Bacillus stearothermophilus*-derived esterase BS1 (commercially available enzyme, manufactured by Julich Fine Chemicals) | −95.4 |
| *Bacillus stearothermophilus*-derived esterase BS3 (commercially available enzyme, manufactured by Julich Fine Chemicals) | −95.4 |
| Pig liver-derived esterase (commercially available enzyme, manufactured by Sigma-Aldrich) | −84.3 |

Example 13

Step (i): Production of Ethyl (S)-2-[(tert-Butylthio)methyl]-2-methylmalonate

In a 1-L jar fermenter (manufactured by ABLE Corporation, Type BMJ), 14.4 g (52.1 mmol) of diethyl 2-[(tert-butylthio)methyl]-2-methylmalonate, 65.0 g of 1 mol/L phosphate buffer (pH 7), 26.0 g of the recombinant *E. coli* JM109/pKCENP1 prepared in Example 11, and 555 g of desalted water were fed, and the resulting mixture was sufficiently mixed. Thereafter, the reaction was allowed to proceed at 30° C. at 500 rpm for 16 hours. During the reaction, the pH was kept at 7.0 using 20 wt % aqueous sodium hydroxide solution. Completion of the reaction was judged by analysis under the conditions of <HPLC1>, based on disappearance of diethyl 2-[(tert-butylthio)methyl]-2-methylmalonate.

The obtained reaction solution was centrifuged at 8000 rpm, to obtain a reaction solution supernatant. Thereafter, the supernatant was subjected to treatment with a microfiltration membrane having a pore size of 0.2 μm for removal of the bacterial cells, and further to treatment with an ultrafiltration membrane with a molecular weight cutoff of 10,000. To the obtained filtrate, 160 mL of toluene was added, and the resulting mixture was sufficiently stirred followed by separation, thereby removing residual impurities such as diethyl 2-[(tert-butylthio)methyl]-2-methylmalonate into the organic layer, and obtaining an aqueous layer containing ethyl 2-[(tert-butylthio)methyl]-2-methylmalonate. The pH of the aqueous layer was lowered to 2.0 using 6 mol/L sulfuric acid, and 160 mL of toluene was added to the solution, followed by sufficiently stirring the resulting mixture, thereby extracting ethyl 2-[(tert-butylthio)methyl]-2-methylmalonate into the toluene layer. By adding 160 mL of toluene to the remaining aqueous layer, and sufficiently mixing the resulting mixture, residual ethyl 2-[(tert-butylthio)methyl]-2-methylmalonate in the aqueous layer was also extracted into the toluene layer.

As a result of analysis of the obtained toluene solution under the conditions of <HPLC1>, it was found that 11.7 g (47.1 mmol; yield, 90.4%) of ethyl 2-[(tert-butylthio)methyl]-2-methylmalonate was obtained. The measurement results obtained were as follows.

¹H-NMR (400 MHz, CDCl₃) δ 1.29 (3H, t, J=7.1 Hz), 1.31 (9H, s), 1.54 (3H, s), 3.02 (1H, d, J=11.9 Hz), 3.08 (1H, d, J=11.9 Hz), 4.24 (2H, q, J=7.1 Hz)

As a result of analysis of the optical purity under the conditions of <HPLC2>, the configuration of the ethyl 2-[(tert-butylthio)methyl]-2-methylmalonate obtained was found to be (S), and its optical purity was found to be 99.8% e.e.

Example 14

Step (ii): Production of Ethyl (R)-2-[(tert-Butylthio)methyl]-3-[(ethoxycarbonyl)oxy]-2-methyl-3-oxopropanoate Under nitrogen gas flow, 22.4 g (90.1 mmol) of ethyl (S)-2-[(tert-butylthio)methyl]-2-methylmalonate produced in Example 13 and 130 mL of toluene were placed in a 300-mL four-necked flask. The resulting mixture was cooled to 5° C., and 10.0 g (99.1 mmol) of triethylamine was added dropwise to the mixture at an inner temperature within the range of 5° C. to 10° C. for 5 minutes. Under nitrogen gas flow, 10.8 g (99.2 mmol) of ethyl chloroformate and 22.4 mL of toluene were placed in a 500-mL four-necked flask, and the resulting mixture was cooled to 5° C. To this mixture, the solution of triethylamine salt of ethyl (S)-2-[(tert-butylthio)methyl]-2-methylmalonate in toluene preliminarily prepared was added dropwise at an inner temperature within the range of 5° C. to 12° C. for 15 minutes. Subsequently, the resulting mixture was stirred for additional 1 hour while an inner temperature of 5° C. was kept. As a result of ¹H-NMR analysis, this solution in toluene was confirmed to be a solution containing ethyl (R)-2-[(tert-butylthio)methyl]-3-[(ethoxycarbonyl)oxy]-2-methyl-3-oxopropanoate. The measurement results obtained were as follows.

¹H-NMR (400 MHz, CDCl₃) δ 1.28 (3H, t, J=7.1 Hz), 1.32 (9H, s), 1.35 (3H, t, J=7.2 Hz), 1.55 (3H, s), 3.03 (1H, d, J=12.1 Hz), 3.09 (1H, d, J=12.1 Hz), 4.24 (2H, q, J=7.1 Hz), 4.32 (2H, q, J=7.1 Hz)

Example 15

Step (iii): Production of Ethyl (S)-2-(azidocarbonyl)-2-[(tert-butylthio)methyl]propanoate The solution of ethyl (R)-2-[(tert-butylthio)methyl]-3-[(ethoxycarbonyl)oxy]-2-methyl-3-oxopropanoate in toluene produced in Example 14 was cooled to 2° C., and an aqueous solution prepared by mixing 9.19 g (108 mmol) of sodium azide with 40 mL of water was added dropwise to the solution at an inner temperature within the range of 2° C. to 4° C. for 4 minutes. The resulting mixture was stirred at an inner temperature of 2° C. for 1 hour, and 60 mL (60.0 mmol) of 1 mol/L hydrochloric acid was added dropwise to the mixture at an inner temperature within the range of 2° C. to 3° C. for 10 minutes. After separating the mixture into a toluene layer and an aqueous layer, the aqueous layer was subjected to extraction again by addition of 45 mL of toluene, and the resulting toluene layer was combined with the previously obtained toluene layer. The combined toluene layer was washed with 35 mL of 5 wt % aqueous sodium hydrogen carbonate solution. To the toluene layer obtained, 11.2 g of anhydrous magnesium sulfate was added, and the resulting mixture was stirred at 0° C. for 2 hours, followed by carrying out filtration. The magnesium sulfate separated by the filtration was washed with 11 mL of toluene, and the washing liquid was mixed with the filtrate. As a result of ¹H-NMR analysis of the obtained solution in toluene, the solution in toluene was found to contain ethyl (S)-2-(azidocarbonyl)-2-[(tent-butylthio)methyl]propanoate. The measurement results obtained were as follows.

¹H-NMR (400 MHz, CDCl₃) δ 6 1.29 (3H, t, J =7.1 Hz), 1.31 (9H, s), 1.54 (3H, s), 3.02 (1H, d, J =11.9 Hz), 3.08 (1H, d, J =11.9 Hz), 4.24 (2H, q, J =7.1 Hz)

Example 16

Step (iv): Production of Ethyl (S)-2-[(tert-Butylthio)methyl]-2-isocyanatopropanoate Under nitrogen gas flow, 45 mL of toluene was placed in a 500 mL four-necked flask, and heated to 85° C. To the flask, the solution containing 23.3 g (85.3 mmol) of ethyl (S)-2-(azidocarbonyl)-2-[(tert-butylthio)methyl]propanoate in toluene produced in Example 15 was added dropwise at an inner temperature within the range of 84° C. to 91° C. for 4 hours. Thereafter, the resulting mixture was stirred at 85° C. for 1 hour, to obtain a solution of ethyl (S)-2-[(tert-butylthio)methyl]-2-isocyanatopropanoate in toluene. As a result of ¹H-NMR analysis, the amount of ethyl (S)-2-[(tert-butylthio)methyl]-2-isocyanatopropanoate contained in this solution in toluene was found to be 21.5 g (87.6 mmol; yield from ethyl (S)-2-[(tert-butylthio)methyl]-2-methylmalonate, 97.2%). The measurement results obtained were as follows.

¹H-NMR (400 MHz, CDCl₃) δ 1.29 (3H, t, J =7.1 Hz), 1.30 (9H, s), 1.52 (3H, s), 2.78(1H, d, J =12.1 Hz), 2.98 (1H, d, J =12.1 Hz), 4.23 (2H, q, J =7.1 Hz)

Example 17

Step (vi-1) and Step (vi-2): Production of Ethyl (S)-4-Methyl-2-oxo-1,3-thiazolidine-4-carboxylate and (S)-4-Methyl-2-oxo-1,3-thiazolidine-4-carboxylic Acid Under nitrogen gas flow, 39.2 g of a solution containing 11.2 g (45.6 mmol) of ethyl (S)-2-[(tert-butylthio)methyl]-2-isocyanatopropanoate in toluene was placed in a 200-mL four-necked flask. To the flask, 9.19 g (88.4 mmol) of 35 wt % hydrochloric acid was added, and the resulting mixture was stirred at 25° C. for 45 minutes. As a result of ¹H-NMR analysis of the toluene layer of this reaction solution, the layer was found to contain ethyl (S)-4-methyl-2-oxo-1,3-thiazolidine-4-carboxylate.

¹H-NMR (400 MHz, CDCl₃) δ 1.32 (3H, t, J=7.1 Hz), 1.60 (3H, s), 3.28 (1H, d, J=11.4 Hz), 3.80 (1H, d, J=11.4 Hz), 4.26 (2H, q, J=7.1 Hz)

Subsequently, the inner temperature of this reaction solution was increased to 60° C. to 70° C., and the reaction solution was then stirred for additional 1hour. After removing toluene by distillation, 22.6 g of water and 2.40 g (23.0 mmol) of 35 wt % hydrochloric acid were added to the solution, and the resulting mixture was stirred at an inner temperature within the range of 70° C. to 90° C. for 4 hours. After allowing the reaction solution to cool to room temperature, precipitated crystals were collected by filtration. The obtained crystals were washed with 23 mL of toluene and 23 mL of water, to obtain 5.97 g of white crystals. As a result of HPLC analysis under the conditions of <HPLC-3>, the white crystals were found to contain 5.56 g (34.5 mol; yield, 75.7%) of (S)-4-methyl-2-oxo-1,3-thiazolidine-4-carboxylic acid. The measurement results on the compound obtained were as follows.

$^1$H-NMR (400 MHz, D$_2$O) δ 1.52 (3H, s), 3.40 (1H, d, J =11.6 Hz), 3.69 (1H, d, J =11.6 Hz)

Example 18

Step (vi-1) and Step (vi-2): Production of Ethyl (S)-4-Methyl-2-oxo-1,3-thiazolidine-4-carboxylate and (S)-4-Methyl-2-oxo-1,3-thiazolidine-4-carboxylic Acid.

Under nitrogen gas flow, 4.62 g of a solution containing 1.33 g (5.4 mmol) of ethyl (S)-2-[(tert-butylthio)methyl]-2-isocyanatopropanoate in toluene was placed in a 50-mL test tube. To the test tube, 1.52 g (5.4 mmol) of p-toluenesulfonic acid monohydrate was added, and the resulting mixture was stirred at room temperature for 60 minutes, followed by adding 8 ml (16.0 mmol) of 2 mol/L aqueous sodium hydroxide solution thereto at the same temperature. After stirring the resulting mixture for 1.5 hours, the toluene layer was removed by separation. To the obtained aqueous layer, 0.4 g of 98 wt % sulfuric acid was added at room temperature. As a result, precipitation of crystals occurred. The mixture was cooled to an inner temperature of 5° C., and the precipitated crystals were collected by filtration. The obtained crystals were washed with a small amount of water, to obtain 0.70 g (4.3 mmol; yield, 79.6%) of (S)-4-methyl-2-oxo-1,3-thiazolidine-4-carboxylic acid.

Example 19

Step (vii): Production of α-Methyl-D-cysteine Hydrochloride

Under nitrogen gas flow, 4.00 g of a white solid containing 3.72 g (23.1 mmol) of (S)-4-methyl-2-oxo-1,3-thiazolidine-4-carboxylic acid produced in Example 17 was placed in a 100-mL four-necked flask. To the flask, 60 mL (720 mmol) of 35 wt % hydrochloric acid was added, and the resulting mixture was heated to an inner temperature of 100° C., followed by stirring the mixture for 51 hours. After removing 35 wt % hydrochloric acid by distillation, an operation of adding 5 mL of toluene and removing 35 wt % hydrochloric acid by azeotropic distillation was repeated twice. To the solid of crude α-methyl-D-cysteine hydrochloride obtained, 12 mL of 2-propanol was added, and the solid was dissolved by heating at 50° C. To the resulting solution, 20 mL of toluene was added, and 8.56 g of the solvent was removed by distillation. The remaining solution was cooled to 0° C. for 2 hours, and the crystals produced were collected by filtration. The crystals obtained were washed with 4 mL of toluene, and dried at 20° C. for 1.5 hours under reduced pressure, to obtain 2.89 g of white crystals. As a result of HPLC analysis under the conditions of <HPLC-3>, the white crystals were found to contain 2.71 g (yield, 68.4%) of α-methyl-D-cysteine hydrochloride. Based on the result of HPLC analysis under the conditions of <HPLC-4>, the optical purity was 99.9% e.e. The measurement results on the compound obtained were as follows.

$^1$H-NMR (400 MHz, D$_2$O) δ 1.53 (3H, s), 2.84 (1H, d, J=15.0 Hz), 3.11 (1H, d, J=15.0 Hz)

INDUSTRIAL APPLICABILITY

By the present invention, an optically active α-substituted cysteine or a salt thereof, which is useful as an intermediate for pharmaceuticals and the like, can be produced more simply, quickly, and safely, using an easily available and inexpensive material. The present invention enables stable production of the optically active α-substituted cysteine or the salt thereof in an industrial scale.

---

The invention claimed is:

1. A method for producing an a-substituted cysteine represented by General Formula (1):

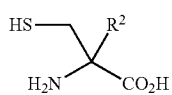
(1)

(wherein $R^2$ represents a $C_1$-$C_4$ alkyl group) or a salt thereof, said method comprising the steps of:

allowing a base or an acid; or an enzyme having an activity to hydrolyze an ester group, a cell having an ability to produce the enzyme, a processed product of the cell, and/or a culture liquid containing the enzyme obtained by culturing the cell; to act on a compound represented by General Formula (2):

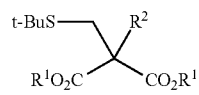
(2)

(wherein each $R^1$ independently represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ represents a $C_1$-$C_4$ alkyl group), to obtain a compound represented by General Formula (3):

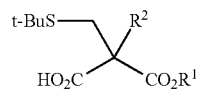
(3)

(wherein $R^1$ and $R^2$ have the same meanings as $R^1$ and $R^2$ in the General Formula (2));

allowing a condensing agent or an acid halogenating agent to act on said compound represented by the General Formula (3), to obtain a compound represented by General Formula (4):

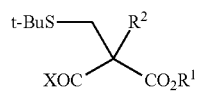
(4)

(wherein $R^1$ and $R^2$ have the same meanings as $R^1$ and $R^2$ in the General Formula (2); X represents —OP(O)(OPh)$_2$, —OP(O)(OEt)$_2$, —OC(O)OR$^3$, or a halogen atom; and $R^3$ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted);

allowing an azidation agent to act on said compound represented by the General Formula (4), to obtain a compound represented by General Formula (5):

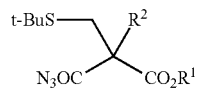
(5)

(wherein $R^1$ and $R^2$ have the same meanings as $R^1$ and $R^2$ in the General Formula (2));

converting, by Curtius rearrangement reaction, said compound represented by the General Formula (5), to obtain a compound represented by General Formula (6):

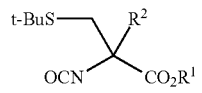
(6)

(wherein $R^1$ and $R^2$ have the same meanings as $R^1$ and $R^2$ in the General Formula (2)); and subjecting said compound represented by the General Formula (6) to a process of converting the isocyanate group to an amino group, a process of hydrolyzing the ester group, and a process of removing the tert-butyl group by action of an acid.

2. The method for producing an α-substituted cysteine or a salt thereof according to claim 1, wherein said enzyme is (A) a protein comprising the amino acid sequence of SEQ ID NO: 4, 6, 8, 10, 12, 14, 16, or 18;

(B) a protein having an identity of not less than 35% to the amino acid sequence of SEQ ID NO: 4, 6, 8, 10, 12, 14, 16, or 18, and having an activity to hydrolyze said compound represented by the General Formula (2) for conversion into a compound represented by General Formula (3S):

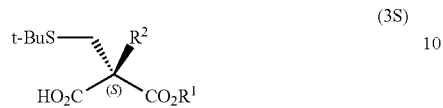

(wherein $R^1$ and $R^2$ have the same meanings as $R^1$ and $R^2$ in the General Formula (3)),
which is a compound represented by the General Formula (3) and having an (S)-configuration; or
(C) a protein comprising the amino acid sequence of SEQ ID NO: 4, 6, 8, 10, 12, 14, 16, or 18 in which one or several amino acids are deleted, substituted, and/or added, and having an activity to hydrolyze said compound represented by the General Formula (2) for conversion into a compound represented by General Formula (3S), which is a compound represented by the General Formula (3) and having an (S)-configuration; and said α-substituted cysteine represented by the General Formula (1) is an α-substituted cysteine represented by the following General Formula (1S) having an (S)-configuration:

(wherein $R^2$ has the same meaning as $R^2$ in the General Formula (1)).

3. A method for producing a compound represented by General Formula (3S) having optical purity of not less than 90.0% e.e:

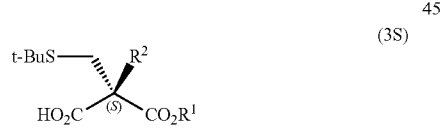

(wherein $R^1$ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ represents a $C_1$-$C_4$ alkyl group), which is a compound represented by the General Formula (3):

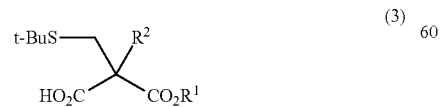

(wherein $R^1$ and $R^2$ have the same meanings as $R^1$ and $R^2$ in the General Formula (3S)) and having an (S)-configuration, said method comprising the step of:

allowing an enzyme having an activity to hydrolyze an ester group, a cell having an ability to produce the enzyme, a processed product of the cell, and/or a culture liquid containing the enzyme obtained by culturing the cell, to act on a compound represented by General Formula (2):

(wherein $R^1$ and $R^2$ have the same meanings as $R^1$ and $R^2$ in the General Formula (3S)), wherein said enzyme is
(A) a protein comprising the amino acid sequence of SEQ ID NO: 4, 6, 8, 10, 12, 14, 16, or 18;
(B) a protein having an identity of not less than 35% to the amino acid sequence of SEQ ID NO: 4, 6, 8, 10, 12, 14, 16, or 18, and having an activity to hydrolyze said compound represented by the General Formula (2) for conversion into said compound represented by the General Formula (3S) having the (S)-configuration; or
(C) a protein comprising the amino acid sequence of SEQ ID NO: 4, 6, 8, 10, 12, 14, 16, or 18 in which one or several amino acids are deleted, substituted, and/or added, and having an activity to hydrolyze said compound represented by the General Formula (2) for conversion into said compound represented by the General Formula (3S) having the (S)-configuration.

4. The method for producing an α-substituted cysteine represented by General Formula (1):

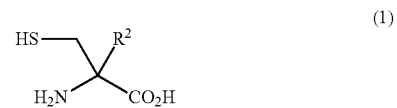

(wherein $R^2$ represents a $C_1$-$C_4$ alkyl group) or a salt thereof according to claim 1, wherein said subjecting step comprises the steps of:
allowing an acid to act on a compound represented by General Formula (6):

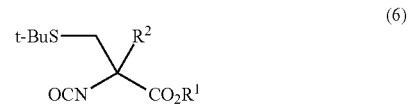

(wherein $R^1$ and $R^2$ have the same meanings as $R^1$ and $R^2$ in the General Formula (6))
to construct a thiazolidinone ring, for conversion into a compound represented by General Formula (7-1):

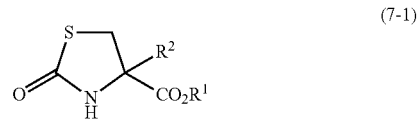

(wherein $R^1$ and $R^2$ have the same meanings as $R^1$ and $R^2$ in the General Formula (6));

allowing an acid or a base to act on said compound represented by the General Formula (7-1) to hydrolyze the ester group, to obtain a compound represented by General Formula (7-2):

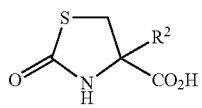

(7-2)

(wherein $R^2$ has the same meaning as $R^2$ in the General Formula (7-1)); and allowing an acid or a base to act on said compound represented by the General Formula (7-2) to open the thiazolidinone ring, to produce said a-substituted cysteine represented by the General Formula (1) or salt thereof.

5. A compound represented by General Formula (4-1):

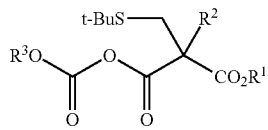

(4-1)

(wherein $R^1$ and $R^3$ each independently represent a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ represents a $C_1$-$C_4$ alkyl group.

6. A method for producing a compound represented by General Formula (2):

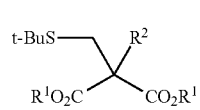

(2)

(wherein each $R^1$ independently represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ represents a $C_1$-$C_4$ alkyl group), said method comprising the step of:
allowing an alkylating agent to act on a compound represented by General Formula (9):

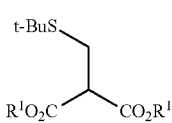

(9)

(wherein $R^1$ has the same meaning as $R^1$ in the General Formula (2)) in the presence of a base, or the steps of:
reacting tert-butyl mercaptan with formaldehyde to obtain tert-butylthiomethanol;
reacting tert-butylthiomethanol with a chlorinating agent in the presence of a base to obtain tert-butylthiochloromethane; and allowing tert-butylthiochloromethane to act on a compound represented by General Formula (8):

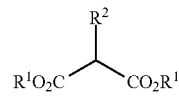

(8)

(wherein $R^1$ has the same meaning as $R^1$ in the General Formula (2), and $R^2$ represents a $C_1$-$C_4$ alkyl group) in the presence of a base, to obtain said compound represented by the General Formula (2).

7. A method for producing a compound represented by General Formula (4-1):

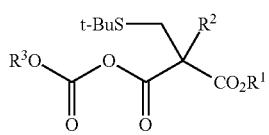

(4-1)

(wherein $R^1$ and $R^3$ each independently represent a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ represents a $C_1$-$C_4$ alkyl group), said method comprising the step of:
allowing a chloroformic ester to act on a compound represented by General Formula (3):

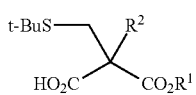

(3)

(wherein $R^1$ and $R^2$ have the same meanings as $R^1$ and $R^2$ in the General Formula (4-1)).

8. A method for producing a compound represented by General Formula (5):

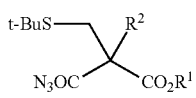

(5)

(wherein $R^1$ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ represents a $C_1$-$C_4$ alkyl group), said method comprising the step of:

allowing a metal azide to act on a compound represented by General Formula (4-1):

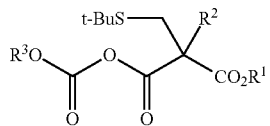
(4-1)

(wherein $R^1$ and $R^2$ have the same meanings as $R^1$ and $R^2$ in the General Formula (5), and $R^3$ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted).

9. A method for producing a compound represented by General Formula (7-1):

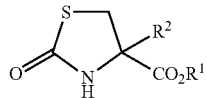
(7-1)

(wherein $R^1$ represents a $C_1$-$C_{10}$ alkyl group which is optionally substituted, a $C_7$-$C_{20}$ aralkyl group which is optionally substituted, or a $C_6$-$C_{12}$ aryl group which is optionally substituted, and $R^2$ represents a $C_1$-$C_4$ alkyl group), said method comprising the step of:

allowing an acid to act on a compound represented by General Formula (6):

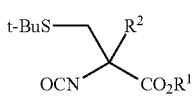
(6)

(wherein $R^1$ and $R^2$ have the same meanings as $R^1$ and $R^2$ in the General Formula (7-1)) to construct a thiazolidinone ring.

* * * * *

UNITED STATES PATENT AND TRADEMARK OFFICE
CERTIFICATE OF CORRECTION

| | | |
|---|---|---|
| PATENT NO. | : 10,071,958 B2 | Page 1 of 1 |
| APPLICATION NO. | : 14/888576 | |
| DATED | : September 11, 2018 | |
| INVENTOR(S) | : Yuuki Asuma et al. | |

It is certified that error appears in the above-identified patent and that said Letters Patent is hereby corrected as shown below:

In the Specification

At Column 73, after Line 66, insert -- <Compound Represented by General Formula (4-1)>" --.

At Column 76, Line 66, "(3H, S)," should be -- (3H, s), --.

At Column 80, Line 24, "npry" should be -- nprv --.

At Column 80, Line 33, "npry" should be -- nprv --.

At Column 83, Line 47, "methy]-3-" should be -- methyl]-3- --.

In the Claims

At Column 121, Line 20, "a-substituted" should be -- α-substituted --.

At Column 125, Line 17, "a-substituted" should be -- α-substituted --.

Signed and Sealed this
Twenty-third Day of July, 2019

Andrei Iancu
*Director of the United States Patent and Trademark Office*

SEQUENCE LISTING

```
<160> NUMBER OF SEQ ID NOS: 20

<210> SEQ ID NO 1
<211> LENGTH: 903
<212> TYPE: DNA
<213> ORGANISM: Bacillus subtilis ThaiI-8
<220> FEATURE:
<221> NAME/KEY: CDS
<222> LOCATION: (1)..(900)

<400> SEQUENCE: 1 atg tca aac cat tca tct agt att ccc gaa tta agt gac aac ggt atc      48
Met Ser Asn His Ser Ser Ser Ile Pro Glu Leu Ser Asp Asn Gly Ile
1               5                  10                  15 cgc tat tat caa act tat aat gaa agc ctt agt ctt tgg ccg gtc cgt      96
Arg Tyr Tyr Gln Thr Tyr Asn Glu Ser Leu Ser Leu Trp Pro Val Arg
                20                  25                  30 tgc aaa tca ttc tat ata tct act cgt ttt ggt caa aca cat gtg att     144
Cys Lys Ser Phe Tyr Ile Ser Thr Arg Phe Gly Gln Thr His Val Ile
            35                  40                  45 gca agc ggc cca gag gat gcc ccg ccg ctt gta tta ctc cac gga gca     192
Ala Ser Gly Pro Glu Asp Ala Pro Pro Leu Val Leu Leu His Gly Ala
        50                  55                  60 tta ttc agc tcg acg atg tgg tat ccc aac atc gcc gat tgg agc agc     240
Leu Phe Ser Ser Thr Met Trp Tyr Pro Asn Ile Ala Asp Trp Ser Ser
65                  70                  75                  80 aaa tac aga act tat gca gtt gat atc ata ggt gat aaa aac aag agt     288
```

```
Lys Tyr Arg Thr Tyr Ala Val Asp Ile Ile Gly Asp Lys Asn Lys Ser
                85                  90                  95 att cct gag aat tta agc ggt aca aga acg gat tac gcc aat tgg ctt         336
Ile Pro Glu Asn Leu Ser Gly Thr Arg Thr Asp Tyr Ala Asn Trp Leu
            100                 105                 110 ctt gat gtg ttt gac aat ctg ggg atc gaa aag tcc cac atg atc gga         384
Leu Asp Val Phe Asp Asn Leu Gly Ile Glu Lys Ser His Met Ile Gly
        115                 120                 125 ctt tcg ctt ggc ggt ctc cat acg atg aat ttc ctt tta cgt atg cct         432
Leu Ser Leu Gly Gly Leu His Thr Met Asn Phe Leu Leu Arg Met Pro
    130                 135                 140 gag aga gta aaa agc gca gct ata ctg agt cca gca gaa acg ttt ttg         480
Glu Arg Val Lys Ser Ala Ala Ile Leu Ser Pro Ala Glu Thr Phe Leu
145                 150                 155                 160 cca ttt cat cac gat ttc tac aaa tac gct ctt ggc ctt aca gcg tca         528
Pro Phe His His Asp Phe Tyr Lys Tyr Ala Leu Gly Leu Thr Ala Ser
                165                 170                 175 aat ggg gtt gaa aaa ttc tta aat tgg atg atg act gat cag aat gtg         576
Asn Gly Val Glu Lys Phe Leu Asn Trp Met Met Thr Asp Gln Asn Val
            180                 185                 190 ctg cac ccg att ttt gtg aag cag ttt cag gca ggg gta atg tgg cag         624
Leu His Pro Ile Phe Val Lys Gln Phe Gln Ala Gly Val Met Trp Gln
        195                 200                 205 gat gga tca aga aat cca aat cct aaa gcc gac gga ttt ccg tat gtt         672
Asp Gly Ser Arg Asn Pro Asn Pro Lys Ala Asp Gly Phe Pro Tyr Val
    210                 215                 220 ttt acc gat gag gaa tta cgt tca gca aga gtt cct atc cta tta tta         720
Phe Thr Asp Glu Glu Leu Arg Ser Ala Arg Val Pro Ile Leu Leu Leu
225                 230                 235                 240 ctt ggt gaa cat gaa gtc atc tat gat ccc cac tca gcc ctg cac cga         768
Leu Gly Glu His Glu Val Ile Tyr Asp Pro His Ser Ala Leu His Arg
                245                 250                 255 gcc tct tca ttc gtt cct gat att gag gcg gaa gtc att aaa aat gcc         816
Ala Ser Ser Phe Val Pro Asp Ile Glu Ala Glu Val Ile Lys Asn Ala
            260                 265                 270 gga cat gtt tta tcg atg gaa caa ccc gct tac gta aat gaa cgt gta         864
Gly His Val Leu Ser Met Glu Gln Pro Ala Tyr Val Asn Glu Arg Val
        275                 280                 285 atg cgt ttt ttc aat gca gaa aca ggc att tca cgg taa                     903
Met Arg Phe Phe Asn Ala Glu Thr Gly Ile Ser Arg
    290                 295                 300

<210> SEQ ID NO 2
<211> LENGTH: 300
<212> TYPE: PRT
<213> ORGANISM: Bacillus subtilis ThaiI-8

<400> SEQUENCE: 2

Met Ser Asn His Ser Ser Ser Ile Pro Glu Leu Ser Asp Asn Gly Ile
1               5                   10                  15

Arg Tyr Tyr Gln Thr Tyr Asn Glu Ser Leu Ser Leu Trp Pro Val Arg
            20                  25                  30

Cys Lys Ser Phe Tyr Ile Ser Thr Arg Phe Gly Gln Thr His Val Ile
        35                  40                  45

Ala Ser Gly Pro Glu Asp Ala Pro Pro Leu Val Leu His Gly Ala
    50                  55                  60

Leu Phe Ser Ser Thr Met Trp Tyr Pro Asn Ile Ala Asp Trp Ser Ser
65                  70                  75                  80

Lys Tyr Arg Thr Tyr Ala Val Asp Ile Ile Gly Asp Lys Asn Lys Ser
```

```
                          85                  90                  95
Ile Pro Glu Asn Leu Ser Gly Thr Arg Thr Asp Tyr Ala Asn Trp Leu
                 100                 105                 110

Leu Asp Val Phe Asp Asn Leu Gly Ile Glu Lys Ser His Met Ile Gly
            115                 120                 125

Leu Ser Leu Gly Gly Leu His Thr Met Asn Phe Leu Leu Arg Met Pro
        130                 135                 140

Glu Arg Val Lys Ser Ala Ala Ile Leu Ser Pro Ala Glu Thr Phe Leu
145                 150                 155                 160

Pro Phe His His Asp Phe Tyr Lys Tyr Ala Leu Gly Leu Thr Ala Ser
                165                 170                 175

Asn Gly Val Glu Lys Phe Leu Asn Trp Met Met Thr Asp Gln Asn Val
            180                 185                 190

Leu His Pro Ile Phe Val Lys Gln Phe Gln Ala Gly Val Met Trp Gln
        195                 200                 205

Asp Gly Ser Arg Asn Pro Asn Pro Lys Ala Asp Gly Phe Pro Tyr Val
    210                 215                 220

Phe Thr Asp Glu Glu Leu Arg Ser Ala Arg Val Pro Ile Leu Leu Leu
225                 230                 235                 240

Leu Gly Glu His Glu Val Ile Tyr Asp Pro His Ser Ala Leu His Arg
                245                 250                 255

Ala Ser Ser Phe Val Pro Asp Ile Glu Ala Glu Val Ile Lys Asn Ala
            260                 265                 270

Gly His Val Leu Ser Met Glu Gln Pro Ala Tyr Val Asn Glu Arg Val
        275                 280                 285

Met Arg Phe Phe Asn Ala Glu Thr Gly Ile Ser Arg
    290                 295                 300

<210> SEQ ID NO 3
<211> LENGTH: 903
<212> TYPE: DNA
<213> ORGANISM: Bacillus subtilis IFO3108
<220> FEATURE:
<221> NAME/KEY: CDS
<222> LOCATION: (1)..(900)

<400> SEQUENCE: 3 atg tca aac cat tca tct agt att ccc gaa tta agt gac aac ggt atc    48
Met Ser Asn His Ser Ser Ser Ile Pro Glu Leu Ser Asp Asn Gly Ile
1               5                   10                  15 cgc tat tat caa act tat aat gaa agc ctt agt ctt tgg ccg gtc cgt    96
Arg Tyr Tyr Gln Thr Tyr Asn Glu Ser Leu Ser Leu Trp Pro Val Arg
                20                  25                  30 tgc aaa tca ttc tat ata tct act cgt ttt ggt caa aca cat gtg att   144
Cys Lys Ser Phe Tyr Ile Ser Thr Arg Phe Gly Gln Thr His Val Ile
            35                  40                  45 gca agc ggc cca gag gat gcc ccg ccg ctt gta tta ctc cac gga gca   192
Ala Ser Gly Pro Glu Asp Ala Pro Pro Leu Val Leu Leu His Gly Ala
        50                  55                  60 tta ttc agc tcg acg atg tgg tat ccc aac atc gcc gat tgg agc agc   240
Leu Phe Ser Ser Thr Met Trp Tyr Pro Asn Ile Ala Asp Trp Ser Ser
65                  70                  75                  80 aaa tac aga act tat gca gtt gat atc ata ggt gat aaa aac aag agt   288
Lys Tyr Arg Thr Tyr Ala Val Asp Ile Ile Gly Asp Lys Asn Lys Ser
                85                  90                  95 att cct gag aat gta agc ggt aca aga acg gat tac gcc aat tgg ctt   336
Ile Pro Glu Asn Val Ser Gly Thr Arg Thr Asp Tyr Ala Asn Trp Leu
                100                 105                 110
```

```
ctt gat gtg ttt gac aat ctg ggg atc gaa aag tcc cac atg atc gga      384
Leu Asp Val Phe Asp Asn Leu Gly Ile Glu Lys Ser His Met Ile Gly
            115                 120                 125 ctt tcg ctt ggc ggt ctc cat acg atg aat ttc ctt tta cgt atg cct      432
Leu Ser Leu Gly Gly Leu His Thr Met Asn Phe Leu Leu Arg Met Pro
        130                 135                 140 gag aga gta aaa agc gca gct ata ctg agt ccg gca gaa acg ttt ttg      480
Glu Arg Val Lys Ser Ala Ala Ile Leu Ser Pro Ala Glu Thr Phe Leu
145                 150                 155                 160 cca ttt cat cac gat ttc tac aaa tac gct ctt ggc ctt aca gcg tca      528
Pro Phe His His Asp Phe Tyr Lys Tyr Ala Leu Gly Leu Thr Ala Ser
                165                 170                 175 aat gga gtt gaa aca ttc tta aat tgg atg atg aat gat cag aat gtg      576
Asn Gly Val Glu Thr Phe Leu Asn Trp Met Met Asn Asp Gln Asn Val
            180                 185                 190 ctg cac ccg att ttt gtg aag cag ttt cag gca ggg gta atg tgg cag      624
Leu His Pro Ile Phe Val Lys Gln Phe Gln Ala Gly Val Met Trp Gln
        195                 200                 205 gat gga tca aga aat cca aat ccc aaa gca gac gga ttt ccg tat gtt      672
Asp Gly Ser Arg Asn Pro Asn Pro Lys Ala Asp Gly Phe Pro Tyr Val
210                 215                 220 ttt acc gat gag gaa tta cgt tca gca aga gtt cct atc cta tta tta      720
Phe Thr Asp Glu Glu Leu Arg Ser Ala Arg Val Pro Ile Leu Leu Leu
225                 230                 235                 240 ctt ggt gaa cat gaa gtc atc tat gat ccc cac tca gcc ctg cac cga      768
Leu Gly Glu His Glu Val Ile Tyr Asp Pro His Ser Ala Leu His Arg
                245                 250                 255 gcc tct tca ttc gtt cct gat att gag gcg gaa gtc att aaa aat gcc      816
Ala Ser Ser Phe Val Pro Asp Ile Glu Ala Glu Val Ile Lys Asn Ala
            260                 265                 270 gga cat gtt tta tcg atg gaa caa ccc gct tac gta aat gaa cgt gta      864
Gly His Val Leu Ser Met Glu Gln Pro Ala Tyr Val Asn Glu Arg Val
        275                 280                 285 atg cgt ttt ttc aat gca gaa aca ggc att tca cgg taa                  903
Met Arg Phe Phe Asn Ala Glu Thr Gly Ile Ser Arg
    290                 295                 300

<210> SEQ ID NO 4
<211> LENGTH: 300
<212> TYPE: PRT
<213> ORGANISM: Bacillus subtilis IFO3108

<400> SEQUENCE: 4

Met Ser Asn His Ser Ser Ile Pro Glu Leu Ser Asp Asn Gly Ile
1               5                   10                  15

Arg Tyr Tyr Gln Thr Tyr Asn Glu Ser Leu Ser Leu Trp Pro Val Arg
            20                  25                  30

Cys Lys Ser Phe Tyr Ile Ser Thr Arg Phe Gly Gln Thr His Val Ile
        35                  40                  45

Ala Ser Gly Pro Glu Asp Ala Pro Pro Leu Val Leu Leu His Gly Ala
    50                  55                  60

Leu Phe Ser Ser Thr Met Trp Tyr Pro Asn Ile Ala Asp Trp Ser Ser
65                  70                  75                  80

Lys Tyr Arg Thr Tyr Ala Val Asp Ile Ile Gly Asp Lys Asn Lys Ser
                85                  90                  95

Ile Pro Glu Asn Val Ser Gly Thr Arg Thr Asp Tyr Ala Asn Trp Leu
            100                 105                 110

Leu Asp Val Phe Asp Asn Leu Gly Ile Glu Lys Ser His Met Ile Gly
```

```
                115                 120                 125
Leu Ser Leu Gly Gly Leu His Thr Met Asn Phe Leu Leu Arg Met Pro
    130                 135                 140

Glu Arg Val Lys Ser Ala Ala Ile Leu Ser Pro Ala Glu Thr Phe Leu
145                 150                 155                 160

Pro Phe His His Asp Phe Tyr Lys Tyr Ala Leu Gly Leu Thr Ala Ser
                165                 170                 175

Asn Gly Val Glu Thr Phe Leu Asn Trp Met Met Asn Asp Gln Asn Val
            180                 185                 190

Leu His Pro Ile Phe Val Lys Gln Phe Gln Ala Gly Val Met Trp Gln
        195                 200                 205

Asp Gly Ser Arg Asn Pro Asn Pro Lys Ala Asp Gly Phe Pro Tyr Val
    210                 215                 220

Phe Thr Asp Glu Glu Leu Arg Ser Ala Arg Val Pro Ile Leu Leu Leu
225                 230                 235                 240

Leu Gly Glu His Glu Val Ile Tyr Asp Pro His Ser Ala Leu His Arg
                245                 250                 255

Ala Ser Ser Phe Val Pro Asp Ile Glu Ala Glu Val Ile Lys Asn Ala
            260                 265                 270

Gly His Val Leu Ser Met Glu Gln Pro Ala Tyr Val Asn Glu Arg Val
        275                 280                 285

Met Arg Phe Phe Asn Ala Glu Thr Gly Ile Ser Arg
    290                 295                 300

<210> SEQ ID NO 5
<211> LENGTH: 903
<212> TYPE: DNA
<213> ORGANISM: Bacillus subtilis IFO3215
<220> FEATURE:
<221> NAME/KEY: CDS
<222> LOCATION: (1)..(900)

<400> SEQUENCE: 5 atg tca aac cat tca tct agt att ccc gaa tta agt gac aac ggt atc      48
Met Ser Asn His Ser Ser Ser Ile Pro Glu Leu Ser Asp Asn Gly Ile
1               5                   10                  15 cgc tat tat caa act tat aat gaa agc ctt agt ctt tgg ccg gtc cgt      96
Arg Tyr Tyr Gln Thr Tyr Asn Glu Ser Leu Ser Leu Trp Pro Val Arg
                20                  25                  30 tgg gaa tca ttc tat ata tct act cgt ttt ggt caa aca cat gtg att     144
Trp Glu Ser Phe Tyr Ile Ser Thr Arg Phe Gly Gln Thr His Val Ile
            35                  40                  45 gca agc ggc cca gag gat gcc ccg ccg ctt ata tta ctc cac gga gca     192
Ala Ser Gly Pro Glu Asp Ala Pro Pro Leu Ile Leu Leu His Gly Ala
        50                  55                  60 tta ttc agc tcg acg atg tgg tat ccc aac atc gcc gat tgg agc agc     240
Leu Phe Ser Ser Thr Met Trp Tyr Pro Asn Ile Ala Asp Trp Ser Ser
65                  70                  75                  80 aaa tac aga act tat gca gtt gat atc ata ggt gat aaa aac aag agt     288
Lys Tyr Arg Thr Tyr Ala Val Asp Ile Ile Gly Asp Lys Asn Lys Ser
                85                  90                  95 att cct gag aat tta agc ggt aca aga acg gat tac gcc aat tgg ctt     336
Ile Pro Glu Asn Leu Ser Gly Thr Arg Thr Asp Tyr Ala Asn Trp Leu
                100                 105                 110 ctt gat gtg ttt gac aat ctg ggg atc gaa aag tcc cac atg atc gga     384
Leu Asp Val Phe Asp Asn Leu Gly Ile Glu Lys Ser His Met Ile Gly
            115                 120                 125 ctt tcg ctt ggc ggt ctc cat acg atg aat ttc ctt tta cgt atg cct     432
```

```
                                                                              480
gag aga gta aaa agc gca gct ata ctg agt ccg gca gaa acg ttt ttg
Glu Arg Val Lys Ser Ala Ala Ile Leu Ser Pro Ala Glu Thr Phe Leu
145                 150                 155                 160

528
cca ttt cat cac gat ttc tac aaa tac gct ctt ggc ctt aca gcg tca
Pro Phe His His Asp Phe Tyr Lys Tyr Ala Leu Gly Leu Thr Ala Ser
                165                 170                 175

576
aat gga gtt gaa aca ttc tta aat tgg atg atg aat gat cag aat gtg
Asn Gly Val Glu Thr Phe Leu Asn Trp Met Met Asn Asp Gln Asn Val
        180                 185                 190

624
ctg cac ccg att ttt gtg aag cag ttt aag gca ggg gta atg tgg cag
Leu His Pro Ile Phe Val Lys Gln Phe Lys Ala Gly Val Met Trp Gln
                195                 200                 205

672
gat gga tca aga aat cca aat cct aaa gca gac gga ttt ccg tat gtt
Asp Gly Ser Arg Asn Pro Asn Pro Lys Ala Asp Gly Phe Pro Tyr Val
210                 215                 220

720
ttt acc gat gag gaa tta cgt tca gca aga gtt cct atc cta tta tta
Phe Thr Asp Glu Glu Leu Arg Ser Ala Arg Val Pro Ile Leu Leu Leu
225                 230                 235                 240

768
ctt ggt gaa cat gaa gtc atc tat gat ccc cac tca gcc ctg cac cga
Leu Gly Glu His Glu Val Ile Tyr Asp Pro His Ser Ala Leu His Arg
                245                 250                 255

816
gcc tct tca ttc gtt cct gat att gag gcg gaa gtc att aaa aat gcc
Ala Ser Ser Phe Val Pro Asp Ile Glu Ala Glu Val Ile Lys Asn Ala
                260                 265                 270

864
gga cat gtt tta tcg atg gaa caa ccc gct tac gta aat gaa cgt gta
Gly His Val Leu Ser Met Glu Gln Pro Ala Tyr Val Asn Glu Arg Val
        275                 280                 285

903
atg cgt ttt ttc aat gca gaa aca ggc att tca cgg taa
Met Arg Phe Phe Asn Ala Glu Thr Gly Ile Ser Arg
290                 295                 300

<210> SEQ ID NO 6
<211> LENGTH: 300
<212> TYPE: PRT
<213> ORGANISM: Bacillus subtilis IFO3215

<400> SEQUENCE: 6

Met Ser Asn His Ser Ser Ile Pro Glu Leu Ser Asp Asn Gly Ile
1               5                   10                  15

Arg Tyr Tyr Gln Thr Tyr Asn Glu Ser Leu Ser Leu Trp Pro Val Arg
                20                  25                  30

Trp Glu Ser Phe Tyr Ile Ser Thr Arg Phe Gly Gln Thr His Val Ile
            35                  40                  45

Ala Ser Gly Pro Glu Asp Ala Pro Pro Leu Ile Leu Leu His Gly Ala
        50                  55                  60

Leu Phe Ser Ser Thr Met Trp Tyr Pro Asn Ile Ala Asp Trp Ser Ser
65                  70                  75                  80

Lys Tyr Arg Thr Tyr Ala Val Asp Ile Ile Gly Asp Lys Asn Lys Ser
                85                  90                  95

Ile Pro Glu Asn Leu Ser Gly Thr Arg Thr Asp Tyr Ala Asn Trp Leu
            100                 105                 110

Leu Asp Val Phe Asp Asn Leu Gly Ile Glu Lys Ser His Met Ile Gly
        115                 120                 125

Leu Ser Leu Gly Gly Leu His Thr Met Asn Phe Leu Leu Arg Met Pro
130                 135                 140

Glu Arg Val Lys Ser Ala Ala Ile Leu Ser Pro Ala Glu Thr Phe Leu
```

```
145                 150                 155                 160
Pro Phe His His Asp Phe Tyr Lys Tyr Ala Leu Gly Leu Thr Ala Ser
                165                 170                 175

Asn Gly Val Glu Thr Phe Leu Asn Trp Met Met Asn Asp Gln Asn Val
            180                 185                 190

Leu His Pro Ile Phe Val Lys Gln Phe Lys Ala Gly Val Met Trp Gln
        195                 200                 205

Asp Gly Ser Arg Asn Pro Asn Pro Lys Ala Asp Gly Phe Pro Tyr Val
    210                 215                 220

Phe Thr Asp Glu Glu Leu Arg Ser Ala Arg Val Pro Ile Leu Leu Leu
225                 230                 235                 240

Leu Gly Glu His Glu Val Ile Tyr Asp Pro His Ser Ala Leu His Arg
                245                 250                 255

Ala Ser Ser Phe Val Pro Asp Ile Glu Ala Glu Val Ile Lys Asn Ala
            260                 265                 270

Gly His Val Leu Ser Met Glu Gln Pro Ala Tyr Val Asn Glu Arg Val
        275                 280                 285

Met Arg Phe Phe Asn Ala Glu Thr Gly Ile Ser Arg
    290                 295                 300

<210> SEQ ID NO 7
<211> LENGTH: 903
<212> TYPE: DNA
<213> ORGANISM: Bacillus subtilis IFO3335
<220> FEATURE:
<221> NAME/KEY: CDS
<222> LOCATION: (1)..(900)

<400> SEQUENCE: 7 atg tca aac cat tca tct agt att ccc gaa tta agt gac aac ggt atc      48
Met Ser Asn His Ser Ser Ser Ile Pro Glu Leu Ser Asp Asn Gly Ile
1               5                   10                  15 cgc tat tat caa act tat aat gaa agc ctt agt ctt tgg ccg gtc cgt      96
Arg Tyr Tyr Gln Thr Tyr Asn Glu Ser Leu Ser Leu Trp Pro Val Arg
            20                  25                  30 tgc aaa tca ttc tat ata tct act cgt ttt ggt caa aca cat gtg att     144
Cys Lys Ser Phe Tyr Ile Ser Thr Arg Phe Gly Gln Thr His Val Ile
        35                  40                  45 gca agc ggc cca gag gat gcc ccg ccg ctt gta tta ctc cac gga gca     192
Ala Ser Gly Pro Glu Asp Ala Pro Pro Leu Val Leu Leu His Gly Ala
    50                  55                  60 tta ttc agc tcg acg atg tgg tat ccc aac atc gcc gat tgg agc agc     240
Leu Phe Ser Ser Thr Met Trp Tyr Pro Asn Ile Ala Asp Trp Ser Ser
65                  70                  75                  80 aaa tac aga act tat gca gtt gat atc ata ggt gat aaa aac aag agt     288
Lys Tyr Arg Thr Tyr Ala Val Asp Ile Ile Gly Asp Lys Asn Lys Ser
                85                  90                  95 att cct gag aat gta agc ggt aca aga acg gat tac gcc aat tgg ctt     336
Ile Pro Glu Asn Val Ser Gly Thr Arg Thr Asp Tyr Ala Asn Trp Leu
            100                 105                 110 ctt gat gtg ttt gac aat ctg ggg atc gaa aag tcc cac atg atc gga     384
Leu Asp Val Phe Asp Asn Leu Gly Ile Glu Lys Ser His Met Ile Gly
        115                 120                 125 ctt tcg ctt ggc ggt ctc cat acg atg aat ttc ctt tta cgt atg cct     432
Leu Ser Leu Gly Gly Leu His Thr Met Asn Phe Leu Leu Arg Met Pro
    130                 135                 140 gag aga gta aaa agc gca gct ata ctg agt ccg gca gaa acg ttt ttg     480
Glu Arg Val Lys Ser Ala Ala Ile Leu Ser Pro Ala Glu Thr Phe Leu
145                 150                 155                 160
```

```
cca ttt cat cac gat ttc tac aaa tac gct ctt ggc ctt aca gcg tca      528
Pro Phe His His Asp Phe Tyr Lys Tyr Ala Leu Gly Leu Thr Ala Ser
            165                 170                 175 aat gga gtt gaa aca ttc tta aat tgg atg atg aat gat cag aat gtg      576
Asn Gly Val Glu Thr Phe Leu Asn Trp Met Met Asn Asp Gln Asn Val
        180                 185                 190 ctg cac ccg att ttt gtg aag cag ttt caa gca ggg gta ata tgg cag      624
Leu His Pro Ile Phe Val Lys Gln Phe Gln Ala Gly Val Ile Trp Gln
    195                 200                 205 gat gga gca aga aat cca aat ccc aaa gca gac gga ttt ccg tat gtt      672
Asp Gly Ala Arg Asn Pro Asn Pro Lys Ala Asp Gly Phe Pro Tyr Val
210                 215                 220 ttt acc gat gag gaa tta cgt tca gca aga gtt cct atc cta tta tta      720
Phe Thr Asp Glu Glu Leu Arg Ser Ala Arg Val Pro Ile Leu Leu Leu
225                 230                 235                 240 ctt ggt gaa cat gaa gtc atc tat gat ccc cac tca gcc ctg cac cga      768
Leu Gly Glu His Glu Val Ile Tyr Asp Pro His Ser Ala Leu His Arg
            245                 250                 255 gcc tct tca ttc gtt cct gat att gag gcg gaa gtc att aaa aat gcc      816
Ala Ser Ser Phe Val Pro Asp Ile Glu Ala Glu Val Ile Lys Asn Ala
        260                 265                 270 gga cat gtt tta tcg atg gaa caa ccc gct tac gta aat gaa cgt gta      864
Gly His Val Leu Ser Met Glu Gln Pro Ala Tyr Val Asn Glu Arg Val
    275                 280                 285 atg cgt ttt ttc aat gca gaa aca ggc att tca cgg taa                  903
Met Arg Phe Phe Asn Ala Glu Thr Gly Ile Ser Arg
290                 295                 300

<210> SEQ ID NO 8
<211> LENGTH: 300
<212> TYPE: PRT
<213> ORGANISM: Bacillus subtilis IFO3335

<400> SEQUENCE: 8

Met Ser Asn His Ser Ser Ile Pro Glu Leu Ser Asp Asn Gly Ile
1               5                   10                  15

Arg Tyr Tyr Gln Thr Tyr Asn Glu Ser Leu Ser Leu Trp Pro Val Arg
            20                  25                  30

Cys Lys Ser Phe Tyr Ile Ser Thr Arg Phe Gly Gln Thr His Val Ile
        35                  40                  45

Ala Ser Gly Pro Glu Asp Ala Pro Pro Leu Val Leu Leu His Gly Ala
    50                  55                  60

Leu Phe Ser Ser Thr Met Trp Tyr Pro Asn Ile Ala Asp Trp Ser Ser
65                  70                  75                  80

Lys Tyr Arg Thr Tyr Ala Val Asp Ile Ile Gly Asp Lys Asn Lys Ser
                85                  90                  95

Ile Pro Glu Asn Val Ser Gly Thr Arg Thr Asp Tyr Ala Asn Trp Leu
            100                 105                 110

Leu Asp Val Phe Asp Asn Leu Gly Ile Glu Lys Ser His Met Ile Gly
        115                 120                 125

Leu Ser Leu Gly Gly Leu His Thr Met Asn Phe Leu Leu Arg Met Pro
    130                 135                 140

Glu Arg Val Lys Ser Ala Ala Ile Leu Ser Pro Ala Glu Thr Phe Leu
145                 150                 155                 160

Pro Phe His His Asp Phe Tyr Lys Tyr Ala Leu Gly Leu Thr Ala Ser
                165                 170                 175

Asn Gly Val Glu Thr Phe Leu Asn Trp Met Met Asn Asp Gln Asn Val
```

```
                   180                 185                 190
Leu His Pro Ile Phe Val Lys Gln Phe Gln Ala Gly Val Ile Trp Gln
                195                 200                 205

Asp Gly Ala Arg Asn Pro Asn Pro Lys Ala Asp Gly Phe Pro Tyr Val
            210                 215                 220

Phe Thr Asp Glu Glu Leu Arg Ser Ala Arg Val Pro Ile Leu Leu Leu
225                 230                 235                 240

Leu Gly Glu His Glu Val Ile Tyr Asp Pro His Ser Ala Leu His Arg
                245                 250                 255

Ala Ser Ser Phe Val Pro Asp Ile Glu Ala Glu Val Ile Lys Asn Ala
            260                 265                 270

Gly His Val Leu Ser Met Glu Gln Pro Ala Tyr Val Asn Glu Arg Val
        275                 280                 285

Met Arg Phe Phe Asn Ala Glu Thr Gly Ile Ser Arg
    290                 295                 300

<210> SEQ ID NO 9
<211> LENGTH: 903
<212> TYPE: DNA
<213> ORGANISM: Bacillus subtilis IFO14144
<220> FEATURE:
<221> NAME/KEY: CDS
<222> LOCATION: (1)..(900)

<400> SEQUENCE: 9 atg tca aac cat tca tct agt att ccc gaa tta agt gac aac ggt atc      48
Met Ser Asn His Ser Ser Ser Ile Pro Glu Leu Ser Asp Asn Gly Ile
1               5                  10                  15 cgc tat tat caa act tat aat gaa agc ctt agt ctt tgg ccg gtc cgt      96
Arg Tyr Tyr Gln Thr Tyr Asn Glu Ser Leu Ser Leu Trp Pro Val Arg
                20                  25                  30 tgt aaa tca ttc tat ata tct act cgt ttt ggt caa aca cat gtg att     144
Cys Lys Ser Phe Tyr Ile Ser Thr Arg Phe Gly Gln Thr His Val Ile
            35                  40                  45 gca agc ggc cca gag gat gcc ccg ccg ctt gta tta ctc cac gga gca     192
Ala Ser Gly Pro Glu Asp Ala Pro Pro Leu Val Leu Leu His Gly Ala
        50                  55                  60 tta ttc agc tcg acg atg tgg tat ccc aac atc gcc gat tgg agc agt     240
Leu Phe Ser Ser Thr Met Trp Tyr Pro Asn Ile Ala Asp Trp Ser Ser
65                  70                  75                  80 aaa tac aga act tat gca gtt gat atc ata ggt gat aaa aac aag agt     288
Lys Tyr Arg Thr Tyr Ala Val Asp Ile Ile Gly Asp Lys Asn Lys Ser
                85                  90                  95 att cct gag aat gta agc ggt aca aga acg gat tac gcc aat tgg ctt     336
Ile Pro Glu Asn Val Ser Gly Thr Arg Thr Asp Tyr Ala Asn Trp Leu
            100                 105                 110 ctt gat gtg ttt gac aat ctg ggg atc gaa aag tcc cac atg atc gga     384
Leu Asp Val Phe Asp Asn Leu Gly Ile Glu Lys Ser His Met Ile Gly
        115                 120                 125 ctt tcg ctt ggc ggt ctc cat acg atg aat ttc ctt tta cgt atg cct     432
Leu Ser Leu Gly Gly Leu His Thr Met Asn Phe Leu Leu Arg Met Pro
    130                 135                 140 gag aga gta aaa agc gca gct ata ctg agt ccg gca gaa acg ttt ttg     480
Glu Arg Val Lys Ser Ala Ala Ile Leu Ser Pro Ala Glu Thr Phe Leu
145                 150                 155                 160 cca ttt cat cac gat ttc tac aaa tac gct ctt ggc ctt aca gcg tca     528
Pro Phe His His Asp Phe Tyr Lys Tyr Ala Leu Gly Leu Thr Ala Ser
                165                 170                 175 aat gga gtt gaa aca ttc tta aat tgg atg atg aat gat cag aat gtg     576
```

```
                Asn Gly Val Glu Thr Phe Leu Asn Trp Met Met Asn Asp Gln Asn Val
                                180                 185                 190 ctg cac ccg att ttt gtg aag cag ttt aag gca ggg gta atg tgg cag          624
Leu His Pro Ile Phe Val Lys Gln Phe Lys Ala Gly Val Met Trp Gln
        195                 200                 205 gat gga tca aga aat cca aat cct aat gcc gac gga ttt ccg tat gtt          672
Asp Gly Ser Arg Asn Pro Asn Pro Asn Ala Asp Gly Phe Pro Tyr Val
210                 215                 220 ttt acc gat gag gaa tta cgt tca gca aga gtt cct atc cta tta tta          720
Phe Thr Asp Glu Glu Leu Arg Ser Ala Arg Val Pro Ile Leu Leu Leu
225                 230                 235                 240 ctt ggt gaa cat gaa gtc atc tat gat ccc cac tca gcc ctg cac cga          768
Leu Gly Glu His Glu Val Ile Tyr Asp Pro His Ser Ala Leu His Arg
                245                 250                 255 gcc tct tca ttc gtt cca gat att gag gcg gaa gtc att aaa aat gcc          816
Ala Ser Ser Phe Val Pro Asp Ile Glu Ala Glu Val Ile Lys Asn Ala
            260                 265                 270 gga cat gtt tta tcg atg gaa caa ccc act tac gta aat gaa cgt gta          864
Gly His Val Leu Ser Met Glu Gln Pro Thr Tyr Val Asn Glu Arg Val
        275                 280                 285 atg cgt ttt ttc aat gca gaa aca ggc att tca cgg taa                      903
Met Arg Phe Phe Asn Ala Glu Thr Gly Ile Ser Arg
290                 295                 300

<210> SEQ ID NO 10
<211> LENGTH: 300
<212> TYPE: PRT
<213> ORGANISM: Bacillus subtilis IFO14144

<400> SEQUENCE: 10

Met Ser Asn His Ser Ser Ser Ile Pro Glu Leu Ser Asp Asn Gly Ile
1               5                   10                  15

Arg Tyr Tyr Gln Thr Tyr Asn Glu Ser Leu Ser Leu Trp Pro Val Arg
                20                  25                  30

Cys Lys Ser Phe Tyr Ile Ser Thr Arg Phe Gly Gln Thr His Val Ile
            35                  40                  45

Ala Ser Gly Pro Glu Asp Ala Pro Pro Leu Val Leu Leu His Gly Ala
        50                  55                  60

Leu Phe Ser Ser Thr Met Trp Tyr Pro Asn Ile Ala Asp Trp Ser Ser
65                  70                  75                  80

Lys Tyr Arg Thr Tyr Ala Val Asp Ile Ile Gly Asp Lys Asn Lys Ser
                85                  90                  95

Ile Pro Glu Asn Val Ser Gly Thr Arg Thr Asp Tyr Ala Asn Trp Leu
            100                 105                 110

Leu Asp Val Phe Asp Asn Leu Gly Ile Glu Lys Ser His Met Ile Gly
        115                 120                 125

Leu Ser Leu Gly Gly Leu His Thr Met Asn Phe Leu Leu Arg Met Pro
130                 135                 140

Glu Arg Val Lys Ser Ala Ala Ile Leu Ser Pro Ala Glu Thr Phe Leu
145                 150                 155                 160

Pro Phe His His Asp Phe Tyr Lys Tyr Ala Leu Gly Leu Thr Ala Ser
                165                 170                 175

Asn Gly Val Glu Thr Phe Leu Asn Trp Met Met Asn Asp Gln Asn Val
            180                 185                 190

Leu His Pro Ile Phe Val Lys Gln Phe Lys Ala Gly Val Met Trp Gln
        195                 200                 205

Asp Gly Ser Arg Asn Pro Asn Pro Asn Ala Asp Gly Phe Pro Tyr Val
```

```
                     210                 215                 220
Phe Thr Asp Glu Glu Leu Arg Ser Ala Arg Val Pro Ile Leu Leu Leu
225                 230                 235                 240

Leu Gly Glu His Glu Val Ile Tyr Asp Pro His Ser Ala Leu His Arg
            245                 250                 255

Ala Ser Ser Phe Val Pro Asp Ile Glu Ala Glu Val Ile Lys Asn Ala
                260                 265                 270

Gly His Val Leu Ser Met Glu Gln Pro Thr Tyr Val Asn Glu Arg Val
            275                 280                 285

Met Arg Phe Phe Asn Ala Glu Thr Gly Ile Ser Arg
290                 295                 300

<210> SEQ ID NO 11
<211> LENGTH: 903
<212> TYPE: DNA
<213> ORGANISM: Bacillus subtilis IFO14191
<220> FEATURE:
<221> NAME/KEY: CDS
<222> LOCATION: (1)..(900)

<400> SEQUENCE: 11 atg tca aac cat tca tct agt att ccc gaa tta agt gac aac ggt atc      48
Met Ser Asn His Ser Ser Ser Ile Pro Glu Leu Ser Asp Asn Gly Ile
1               5                   10                  15 cgc tat tat caa act tat aat gaa agc ctt agt ctt tgg ccg gtc cgt      96
Arg Tyr Tyr Gln Thr Tyr Asn Glu Ser Leu Ser Leu Trp Pro Val Arg
                20                  25                  30 tgt aaa tca ttc tat ata tct act cgt ttt ggt caa aca cat gtg att     144
Cys Lys Ser Phe Tyr Ile Ser Thr Arg Phe Gly Gln Thr His Val Ile
            35                  40                  45 gca agc ggc cca gag gat gcc ccg ccg ctt gta tta ctc cac gga gca     192
Ala Ser Gly Pro Glu Asp Ala Pro Pro Leu Val Leu Leu His Gly Ala
        50                  55                  60 tta ttc agc tcg acg atg tgg tat ccc aac atc gcc gat tgg agc agt     240
Leu Phe Ser Ser Thr Met Trp Tyr Pro Asn Ile Ala Asp Trp Ser Ser
65                  70                  75                  80 aaa tac aga act tat gca gtt gat atc ata ggt gat aaa aac aag agt     288
Lys Tyr Arg Thr Tyr Ala Val Asp Ile Ile Gly Asp Lys Asn Lys Ser
                85                  90                  95 att cct gag aat gta agc ggt aca aga acg gat tac gcc aat tgg ctt     336
Ile Pro Glu Asn Val Ser Gly Thr Arg Thr Asp Tyr Ala Asn Trp Leu
            100                 105                 110 ctt gat gtg ttt gac aat ctg ggg atc gaa aag tcc cac atg atc gga     384
Leu Asp Val Phe Asp Asn Leu Gly Ile Glu Lys Ser His Met Ile Gly
        115                 120                 125 ctt tcg ctt ggc ggt ctc cat acg atg aat ttc ctt tta cgt atg cct     432
Leu Ser Leu Gly Gly Leu His Thr Met Asn Phe Leu Leu Arg Met Pro
    130                 135                 140 gag aga gta aaa agc gca gct ata ctg agt ccg gca gaa acg ttt ttg     480
Glu Arg Val Lys Ser Ala Ala Ile Leu Ser Pro Ala Glu Thr Phe Leu
145                 150                 155                 160 cca ttt cat cac gat ttc tac aaa tac gct ctt ggc ctt aca gcg tca     528
Pro Phe His His Asp Phe Tyr Lys Tyr Ala Leu Gly Leu Thr Ala Ser
                165                 170                 175 aat gga gtt gaa aca ttc tta aat tgg atg atg aat gat cag aat gtg     576
Asn Gly Val Glu Thr Phe Leu Asn Trp Met Met Asn Asp Gln Asn Val
            180                 185                 190 ctg cac ccg att ttt gtg aag cag ttt aag gca ggg gta atg tgg cag     624
Leu His Pro Ile Phe Val Lys Gln Phe Lys Ala Gly Val Met Trp Gln
        195                 200                 205
```

-continued

```
gat gga tca aga aat cca aat cct aat gcc gac gga ttt ccg tat gtt    672
Asp Gly Ser Arg Asn Pro Asn Pro Asn Ala Asp Gly Phe Pro Tyr Val
    210                 215                 220 ttt acc gat gag gaa tta cgt tca gca aga gtt cct atc cta tta tta    720
Phe Thr Asp Glu Glu Leu Arg Ser Ala Arg Val Pro Ile Leu Leu Leu
225                 230                 235                 240 ctt ggt gaa cat gaa gtc atc tat gat ccc cac tca gcc ctg cac cga    768
Leu Gly Glu His Glu Val Ile Tyr Asp Pro His Ser Ala Leu His Arg
                245                 250                 255 gcc tct tca ttc gtt cca gat att gag gcg gaa gtc att aaa aat gcc    816
Ala Ser Ser Phe Val Pro Asp Ile Glu Ala Glu Val Ile Lys Asn Ala
            260                 265                 270 gga cat gtt tta tcg atg gaa caa ccc act tac gta aat gaa cgt gta    864
Gly His Val Leu Ser Met Glu Gln Pro Thr Tyr Val Asn Glu Arg Val
        275                 280                 285 ttg cgt ttt ttc aat gca gaa aca ggc att tca cgg taa                903
Leu Arg Phe Phe Asn Ala Glu Thr Gly Ile Ser Arg
    290                 295                 300

<210> SEQ ID NO 12
<211> LENGTH: 300
<212> TYPE: PRT
<213> ORGANISM: Bacillus subtilis IFO14191

<400> SEQUENCE: 12

Met Ser Asn His Ser Ser Ser Ile Pro Glu Leu Ser Asp Asn Gly Ile
1               5                   10                  15

Arg Tyr Tyr Gln Thr Tyr Asn Glu Ser Leu Ser Leu Trp Pro Val Arg
            20                  25                  30

Cys Lys Ser Phe Tyr Ile Ser Thr Arg Phe Gly Gln Thr His Val Ile
        35                  40                  45

Ala Ser Gly Pro Glu Asp Ala Pro Pro Leu Val Leu Leu His Gly Ala
    50                  55                  60

Leu Phe Ser Ser Thr Met Trp Tyr Pro Asn Ile Ala Asp Trp Ser Ser
65                  70                  75                  80

Lys Tyr Arg Thr Tyr Ala Val Asp Ile Ile Gly Asp Lys Asn Lys Ser
                85                  90                  95

Ile Pro Glu Asn Val Ser Gly Thr Arg Thr Asp Tyr Ala Asn Trp Leu
            100                 105                 110

Leu Asp Val Phe Asp Asn Leu Gly Ile Glu Lys Ser His Met Ile Gly
        115                 120                 125

Leu Ser Leu Gly Gly Leu His Thr Met Asn Phe Leu Leu Arg Met Pro
    130                 135                 140

Glu Arg Val Lys Ser Ala Ala Ile Leu Ser Pro Ala Glu Thr Phe Leu
145                 150                 155                 160

Pro Phe His His Asp Phe Tyr Lys Tyr Ala Leu Gly Leu Thr Ala Ser
                165                 170                 175

Asn Gly Val Glu Thr Phe Leu Asn Trp Met Met Asn Asp Gln Asn Val
            180                 185                 190

Leu His Pro Ile Phe Val Lys Gln Phe Lys Ala Gly Val Met Trp Gln
        195                 200                 205

Asp Gly Ser Arg Asn Pro Asn Pro Asn Ala Asp Gly Phe Pro Tyr Val
    210                 215                 220

Phe Thr Asp Glu Glu Leu Arg Ser Ala Arg Val Pro Ile Leu Leu Leu
225                 230                 235                 240

Leu Gly Glu His Glu Val Ile Tyr Asp Pro His Ser Ala Leu His Arg
```

```
                       245                 250                 255
Ala Ser Ser Phe Val Pro Asp Ile Glu Ala Glu Val Ile Lys Asn Ala
            260                 265                 270

Gly His Val Leu Ser Met Glu Gln Pro Thr Tyr Val Asn Glu Arg Val
        275                 280                 285

Leu Arg Phe Phe Asn Ala Glu Thr Gly Ile Ser Arg
    290                 295                 300

<210> SEQ ID NO 13
<211> LENGTH: 903
<212> TYPE: DNA
<213> ORGANISM: Bacillus subtilis IFO14473
<220> FEATURE:
<221> NAME/KEY: CDS
<222> LOCATION: (1)..(900)

<400> SEQUENCE: 13 atg tca aac cat tca tct agt att ccc gaa tta agt gac aac ggt atc     48
Met Ser Asn His Ser Ser Ser Ile Pro Glu Leu Ser Asp Asn Gly Ile
1               5                   10                  15 cgc tat tat caa act tat aat gaa agc ctt agt ctt tgg ccg gtc cgt     96
Arg Tyr Tyr Gln Thr Tyr Asn Glu Ser Leu Ser Leu Trp Pro Val Arg
            20                  25                  30 tgt aaa tca ttc tat ata tct act cgt ttt ggt caa aca cat gtg att    144
Cys Lys Ser Phe Tyr Ile Ser Thr Arg Phe Gly Gln Thr His Val Ile
        35                  40                  45 gca agc ggc cca gag gat gcc ccg ccg ctt gta tta ctc cac gga gca    192
Ala Ser Gly Pro Glu Asp Ala Pro Pro Leu Val Leu Leu His Gly Ala
    50                  55                  60 tta ttc agc tcg acg atg tgg tat ccc aac atc gcc gat tgg agc agt    240
Leu Phe Ser Ser Thr Met Trp Tyr Pro Asn Ile Ala Asp Trp Ser Ser
65                  70                  75                  80 aaa tac aga act tat gca gtt gat atc ata ggt gat aaa aac aag agt    288
Lys Tyr Arg Thr Tyr Ala Val Asp Ile Ile Gly Asp Lys Asn Lys Ser
                85                  90                  95 att cct gag aat gta agc ggt aca aga acg gat tac gcc aat tgg ctt    336
Ile Pro Glu Asn Val Ser Gly Thr Arg Thr Asp Tyr Ala Asn Trp Leu
            100                 105                 110 ctt gat gtg ttt gac aat ctg ggg atc gaa aag tcc cac atg atc gga    384
Leu Asp Val Phe Asp Asn Leu Gly Ile Glu Lys Ser His Met Ile Gly
        115                 120                 125 ctt tcg ctt ggc ggt ctc cat acg atg aat ttc ctt tta cgt atg cct    432
Leu Ser Leu Gly Gly Leu His Thr Met Asn Phe Leu Leu Arg Met Pro
    130                 135                 140 gag aga gta aaa agc gca gct ata ctg agt ccg gca gaa acg ttt ttg    480
Glu Arg Val Lys Ser Ala Ala Ile Leu Ser Pro Ala Glu Thr Phe Leu
145                 150                 155                 160 cca ttt cat cac gat ttc tac aaa tac gct ctt ggc ctt aca gcg tca    528
Pro Phe His His Asp Phe Tyr Lys Tyr Ala Leu Gly Leu Thr Ala Ser
                165                 170                 175 aat gga gtt gaa aca ttc tta aat tgg atg atg aat gat cag aat gtg    576
Asn Gly Val Glu Thr Phe Leu Asn Trp Met Met Asn Asp Gln Asn Val
            180                 185                 190 ctg cac ccg att ttt gtg aag cag ttt cag gca ggg gta atg tgg cag    624
Leu His Pro Ile Phe Val Lys Gln Phe Gln Ala Gly Val Met Trp Gln
        195                 200                 205 gat gga tca aga aat cca aat cct aat gcc gac gga ttt ccg tat gtt    672
Asp Gly Ser Arg Asn Pro Asn Pro Asn Ala Asp Gly Phe Pro Tyr Val
    210                 215                 220 ttt acc gat gag gaa tta cgt tca gca aga gtt cct atc cta tta tta    720
```

```
Phe Thr Asp Glu Glu Leu Arg Ser Ala Arg Val Pro Ile Leu Leu Leu
225                 230                 235                 240 ctt ggt gaa cat gaa gtc atc tat gat ccc cac tca gcc ctg cac cga        768
Leu Gly Glu His Glu Val Ile Tyr Asp Pro His Ser Ala Leu His Arg
                245                 250                 255 gcc tct tca ttc gtt cct gat att gag gtg gaa gtc att aaa aat gcc        816
Ala Ser Ser Phe Val Pro Asp Ile Glu Val Glu Val Ile Lys Asn Ala
            260                 265                 270 gga cat gtt tta tcg ata gaa caa ccc gct tac gta aat gaa cgt gta        864
Gly His Val Leu Ser Ile Glu Gln Pro Ala Tyr Val Asn Glu Arg Val
        275                 280                 285 atg cgt ttt ttc aat gca gaa aca ggc att tca cgg taa                    903
Met Arg Phe Phe Asn Ala Glu Thr Gly Ile Ser Arg
    290                 295                 300

<210> SEQ ID NO 14
<211> LENGTH: 300
<212> TYPE: PRT
<213> ORGANISM: Bacillus subtilis IFO14473

<400> SEQUENCE: 14

Met Ser Asn His Ser Ser Ile Pro Glu Leu Ser Asp Asn Gly Ile
1               5                   10                  15

Arg Tyr Tyr Gln Thr Tyr Asn Glu Ser Leu Ser Leu Trp Pro Val Arg
                20                  25                  30

Cys Lys Ser Phe Tyr Ile Ser Thr Arg Phe Gly Gln Thr His Val Ile
            35                  40                  45

Ala Ser Gly Pro Glu Asp Ala Pro Pro Leu Val Leu Leu His Gly Ala
        50                  55                  60

Leu Phe Ser Ser Thr Met Trp Tyr Pro Asn Ile Ala Asp Trp Ser Ser
65                  70                  75                  80

Lys Tyr Arg Thr Tyr Ala Val Asp Ile Ile Gly Asp Lys Asn Lys Ser
                85                  90                  95

Ile Pro Glu Asn Val Ser Gly Thr Arg Thr Asp Tyr Ala Asn Trp Leu
            100                 105                 110

Leu Asp Val Phe Asp Asn Leu Gly Ile Glu Lys Ser His Met Ile Gly
        115                 120                 125

Leu Ser Leu Gly Gly Leu His Thr Met Asn Phe Leu Leu Arg Met Pro
    130                 135                 140

Glu Arg Val Lys Ser Ala Ala Ile Leu Ser Pro Ala Glu Thr Phe Leu
145                 150                 155                 160

Pro Phe His His Asp Phe Tyr Lys Tyr Ala Leu Gly Leu Thr Ala Ser
                165                 170                 175

Asn Gly Val Glu Thr Phe Leu Asn Trp Met Met Asn Asp Gln Asn Val
            180                 185                 190

Leu His Pro Ile Phe Val Lys Gln Phe Gln Ala Gly Val Met Trp Gln
        195                 200                 205

Asp Gly Ser Arg Asn Pro Asn Pro Asn Ala Asp Gly Phe Pro Tyr Val
    210                 215                 220

Phe Thr Asp Glu Glu Leu Arg Ser Ala Arg Val Pro Ile Leu Leu Leu
225                 230                 235                 240

Leu Gly Glu His Glu Val Ile Tyr Asp Pro His Ser Ala Leu His Arg
                245                 250                 255

Ala Ser Ser Phe Val Pro Asp Ile Glu Val Glu Val Ile Lys Asn Ala
            260                 265                 270

Gly His Val Leu Ser Ile Glu Gln Pro Ala Tyr Val Asn Glu Arg Val
```

Met Arg Phe Phe Asn Ala Glu Thr Gly Ile Ser Arg
    275                 280                 285

Met Arg Phe Phe Asn Ala Glu Thr Gly Ile Ser Arg
    290                 295                 300

<210> SEQ ID NO 15
<211> LENGTH: 903
<212> TYPE: DNA
<213> ORGANISM: Bacillus subtilis IFO101246
<220> FEATURE:
<221> NAME/KEY: CDS
<222> LOCATION: (1)..(900)

<400> SEQUENCE: 15

| | | | | | | | | | | | | | | | |
|---|---|---|---|---|---|---|---|---|---|---|---|---|---|---|---|
| atg | tca | aac | cat | tca | tct | agt | att | ccc | gaa | tta | agt | gac | aac | ggt | atc | 48 |
| Met | Ser | Asn | His | Ser | Ser | Ser | Ile | Pro | Glu | Leu | Ser | Asp | Asn | Gly | Ile | |
| 1 | | | | 5 | | | | | 10 | | | | | 15 | | |

| cgc | tat | tat | caa | act | tat | aat | gaa | agc | ctt | agt | ctt | tgg | ccg | gtc | cgt | 96 |
|---|---|---|---|---|---|---|---|---|---|---|---|---|---|---|---|---|
| Arg | Tyr | Tyr | Gln | Thr | Tyr | Asn | Glu | Ser | Leu | Ser | Leu | Trp | Pro | Val | Arg | |
| | | | 20 | | | | | 25 | | | | | 30 | | | |

| tgt | aaa | tca | ttc | tat | ata | tct | act | cgt | ttt | ggt | caa | aca | cat | gtg | att | 144 |
|---|---|---|---|---|---|---|---|---|---|---|---|---|---|---|---|---|
| Cys | Lys | Ser | Phe | Tyr | Ile | Ser | Thr | Arg | Phe | Gly | Gln | Thr | His | Val | Ile | |
| | | 35 | | | | | 40 | | | | | 45 | | | | |

| gca | agc | ggc | cca | gag | gat | gcc | ccg | ccg | ctt | gta | tta | ctc | cac | gga | gca | 192 |
|---|---|---|---|---|---|---|---|---|---|---|---|---|---|---|---|---|
| Ala | Ser | Gly | Pro | Glu | Asp | Ala | Pro | Pro | Leu | Val | Leu | Leu | His | Gly | Ala | |
| | 50 | | | | | 55 | | | | | 60 | | | | | |

| tta | ttc | agc | tcg | acg | atg | tgg | tat | ccc | aac | atc | gcc | gat | tgg | agc | agt | 240 |
|---|---|---|---|---|---|---|---|---|---|---|---|---|---|---|---|---|
| Leu | Phe | Ser | Ser | Thr | Met | Trp | Tyr | Pro | Asn | Ile | Ala | Asp | Trp | Ser | Ser | |
| 65 | | | | | 70 | | | | | 75 | | | | | 80 | |

| aaa | tac | aga | act | tat | gca | gtt | gat | atc | ata | ggt | gat | aaa | aac | aag | agt | 288 |
|---|---|---|---|---|---|---|---|---|---|---|---|---|---|---|---|---|
| Lys | Tyr | Arg | Thr | Tyr | Ala | Val | Asp | Ile | Ile | Gly | Asp | Lys | Asn | Lys | Ser | |
| | | | | 85 | | | | | 90 | | | | | 95 | | |

| att | cct | gag | aat | gta | agc | ggt | aca | aga | acg | gat | tac | gcc | aat | tgg | ctt | 336 |
|---|---|---|---|---|---|---|---|---|---|---|---|---|---|---|---|---|
| Ile | Pro | Glu | Asn | Val | Ser | Gly | Thr | Arg | Thr | Asp | Tyr | Ala | Asn | Trp | Leu | |
| | | | 100 | | | | | 105 | | | | | 110 | | | |

| ctt | gat | gtg | ttt | gac | aat | ctg | ggg | atc | gaa | aag | tcc | cac | atg | atc | gga | 384 |
|---|---|---|---|---|---|---|---|---|---|---|---|---|---|---|---|---|
| Leu | Asp | Val | Phe | Asp | Asn | Leu | Gly | Ile | Glu | Lys | Ser | His | Met | Ile | Gly | |
| | | 115 | | | | | 120 | | | | | 125 | | | | |

| ctt | tcg | ctt | ggc | ggt | ctc | cat | acg | atg | aat | ttc | ctt | tta | cgt | atg | cct | 432 |
|---|---|---|---|---|---|---|---|---|---|---|---|---|---|---|---|---|
| Leu | Ser | Leu | Gly | Gly | Leu | His | Thr | Met | Asn | Phe | Leu | Leu | Arg | Met | Pro | |
| | 130 | | | | | 135 | | | | | 140 | | | | | |

| gag | aga | gta | aaa | agc | gca | gct | ata | ctg | agt | ccg | gca | gaa | acg | ttt | ttg | 480 |
|---|---|---|---|---|---|---|---|---|---|---|---|---|---|---|---|---|
| Glu | Arg | Val | Lys | Ser | Ala | Ala | Ile | Leu | Ser | Pro | Ala | Glu | Thr | Phe | Leu | |
| 145 | | | | | 150 | | | | | 155 | | | | | 160 | |

| cca | ttt | cat | cac | gat | ttc | tac | aaa | tac | gct | ctt | ggc | ctt | aca | gcg | tca | 528 |
|---|---|---|---|---|---|---|---|---|---|---|---|---|---|---|---|---|
| Pro | Phe | His | His | Asp | Phe | Tyr | Lys | Tyr | Ala | Leu | Gly | Leu | Thr | Ala | Ser | |
| | | | | 165 | | | | | 170 | | | | | 175 | | |

| aat | gga | gtt | gaa | aca | ttc | tta | aat | tgg | atg | atg | aat | gat | cag | aat | gtg | 576 |
|---|---|---|---|---|---|---|---|---|---|---|---|---|---|---|---|---|
| Asn | Gly | Val | Glu | Thr | Phe | Leu | Asn | Trp | Met | Met | Asn | Asp | Gln | Asn | Val | |
| | | | 180 | | | | | 185 | | | | | 190 | | | |

| ctg | cac | ccg | att | ttt | gtg | aag | cag | ttt | caa | gca | ggg | gta | ata | tgg | cag | 624 |
|---|---|---|---|---|---|---|---|---|---|---|---|---|---|---|---|---|
| Leu | His | Pro | Ile | Phe | Val | Lys | Gln | Phe | Gln | Ala | Gly | Val | Ile | Trp | Gln | |
| | | 195 | | | | | 200 | | | | | 205 | | | | |

| gat | gga | gca | aga | aat | cca | aat | cct | aaa | gcc | gac | gga | ttt | ccg | tat | gtt | 672 |
|---|---|---|---|---|---|---|---|---|---|---|---|---|---|---|---|---|
| Asp | Gly | Ala | Arg | Asn | Pro | Asn | Pro | Lys | Ala | Asp | Gly | Phe | Pro | Tyr | Val | |
| | 210 | | | | | 215 | | | | | 220 | | | | | |

| ttt | acc | gat | gag | gaa | tta | cgt | tca | gca | aga | gtt | cct | atc | cta | tta | tta | 720 |
|---|---|---|---|---|---|---|---|---|---|---|---|---|---|---|---|---|
| Phe | Thr | Asp | Glu | Glu | Leu | Arg | Ser | Ala | Arg | Val | Pro | Ile | Leu | Leu | Leu | |
| 225 | | | | | 230 | | | | | 235 | | | | | 240 | |

| ctt | ggt | gaa | cat | gaa | gtc | atc | tat | gat | ccc | cac | tca | gcc | ctg | cac | cga | 768 |
|---|---|---|---|---|---|---|---|---|---|---|---|---|---|---|---|---|
| Leu | Gly | Glu | His | Glu | Val | Ile | Tyr | Asp | Pro | His | Ser | Ala | Leu | His | Arg | |
| | | | | 245 | | | | | 250 | | | | | 255 | | |

```
gcc tct tca ttc gtt cca gat att gag gcg gaa gtc att aaa aat gcc    816
Ala Ser Ser Phe Val Pro Asp Ile Glu Ala Glu Val Ile Lys Asn Ala
        260                 265                 270 gga cat gtt tta tcg atg gaa caa ccc gct tac gta aat gaa cgt gta    864
Gly His Val Leu Ser Met Glu Gln Pro Ala Tyr Val Asn Glu Arg Val
    275                 280                 285 atg cgt ttt ttc aat gca gaa aca ggc att tca ggg taa                903
Met Arg Phe Phe Asn Ala Glu Thr Gly Ile Ser Gly
290                 295                 300
```

<210> SEQ ID NO 16
<211> LENGTH: 300
<212> TYPE: PRT
<213> ORGANISM: Bacillus subtilis IFO101246

<400> SEQUENCE: 16

```
Met Ser Asn His Ser Ser Ile Pro Glu Leu Ser Asp Asn Gly Ile
1               5                   10                  15

Arg Tyr Tyr Gln Thr Tyr Asn Glu Ser Leu Ser Leu Trp Pro Val Arg
            20                  25                  30

Cys Lys Ser Phe Tyr Ile Ser Thr Arg Phe Gly Gln Thr His Val Ile
        35                  40                  45

Ala Ser Gly Pro Glu Asp Ala Pro Pro Leu Val Leu His Gly Ala
    50                  55                  60

Leu Phe Ser Ser Thr Met Trp Tyr Pro Asn Ile Ala Asp Trp Ser Ser
65                  70                  75                  80

Lys Tyr Arg Thr Tyr Ala Val Asp Ile Ile Gly Asp Lys Asn Lys Ser
                85                  90                  95

Ile Pro Glu Asn Val Ser Gly Thr Arg Thr Asp Tyr Ala Asn Trp Leu
            100                 105                 110

Leu Asp Val Phe Asp Asn Leu Gly Ile Glu Lys Ser His Met Ile Gly
        115                 120                 125

Leu Ser Leu Gly Gly Leu His Thr Met Asn Phe Leu Leu Arg Met Pro
    130                 135                 140

Glu Arg Val Lys Ser Ala Ala Ile Leu Ser Pro Ala Glu Thr Phe Leu
145                 150                 155                 160

Pro Phe His His Asp Phe Tyr Lys Tyr Ala Leu Gly Leu Thr Ala Ser
                165                 170                 175

Asn Gly Val Glu Thr Phe Leu Asn Trp Met Met Asn Asp Gln Asn Val
            180                 185                 190

Leu His Pro Ile Phe Val Lys Gln Phe Gln Ala Gly Val Ile Trp Gln
        195                 200                 205

Asp Gly Ala Arg Asn Pro Asn Pro Lys Ala Asp Gly Phe Pro Tyr Val
    210                 215                 220

Phe Thr Asp Glu Glu Leu Arg Ser Ala Arg Val Pro Ile Leu Leu Leu
225                 230                 235                 240

Leu Gly Glu His Glu Val Ile Tyr Asp Pro His Ser Ala Leu His Arg
                245                 250                 255

Ala Ser Ser Phe Val Pro Asp Ile Glu Ala Glu Val Ile Lys Asn Ala
            260                 265                 270

Gly His Val Leu Ser Met Glu Gln Pro Ala Tyr Val Asn Glu Arg Val
        275                 280                 285

Met Arg Phe Phe Asn Ala Glu Thr Gly Ile Ser Gly
    290                 295                 300
```

```
<210> SEQ ID NO 17
<211> LENGTH: 903
<212> TYPE: DNA
<213> ORGANISM: Bacillus subtilis IFO101590
<220> FEATURE:
<221> NAME/KEY: CDS
<222> LOCATION: (1)..(900)

<400> SEQUENCE: 17 atg tca aac cat tca tct agt att ccc gaa tta agt gac aac ggt atc      48
Met Ser Asn His Ser Ser Ser Ile Pro Glu Leu Ser Asp Asn Gly Ile
1               5                   10                  15 cgc tat tat caa act tat aat gaa agc ctt agt ctt tgg ccg gtc cgt      96
Arg Tyr Tyr Gln Thr Tyr Asn Glu Ser Leu Ser Leu Trp Pro Val Arg
            20                  25                  30 tgg gaa tca ttc tat ata tct act cgt ttt ggt caa aca cat gtg att     144
Trp Glu Ser Phe Tyr Ile Ser Thr Arg Phe Gly Gln Thr His Val Ile
        35                  40                  45 gca agc ggc cca gag gat gcc ccg ccg ctt gta tta ctc cac gga gca     192
Ala Ser Gly Pro Glu Asp Ala Pro Pro Leu Val Leu Leu His Gly Ala
    50                  55                  60 tta ttc agc tcg acg atg tgg tat ccc aac atc gcc gat tgg agc agt     240
Leu Phe Ser Ser Thr Met Trp Tyr Pro Asn Ile Ala Asp Trp Ser Ser
65                  70                  75                  80 aaa tac aga act tat gca gtt gat atc ata ggt gat aaa aac aag agt     288
Lys Tyr Arg Thr Tyr Ala Val Asp Ile Ile Gly Asp Lys Asn Lys Ser
                85                  90                  95 att cct gag aat tta agc ggt aca aga acg gat tac gcc aat tgg ctt     336
Ile Pro Glu Asn Leu Ser Gly Thr Arg Thr Asp Tyr Ala Asn Trp Leu
            100                 105                 110 ctt gat gtg ttt gac aat ctg ggg atc gaa aag tcc cac atg atc gga     384
Leu Asp Val Phe Asp Asn Leu Gly Ile Glu Lys Ser His Met Ile Gly
        115                 120                 125 ctt tcg ctt ggc ggt ctc cat acg atg aat ttc ctt tta cgt atg cct     432
Leu Ser Leu Gly Gly Leu His Thr Met Asn Phe Leu Leu Arg Met Pro
    130                 135                 140 gag aga gta aaa agc gca gct ata ctg agt ccg gca gaa acg ttt ttg     480
Glu Arg Val Lys Ser Ala Ala Ile Leu Ser Pro Ala Glu Thr Phe Leu
145                 150                 155                 160 cca ttt cat cac gat ttc tac aaa tac gct ctt ggc ctt aca gcg tca     528
Pro Phe His His Asp Phe Tyr Lys Tyr Ala Leu Gly Leu Thr Ala Ser
                165                 170                 175 aat gga gtt gaa aca ttc tta aat tgg atg atg aat gat cag aat gtg     576
Asn Gly Val Glu Thr Phe Leu Asn Trp Met Met Asn Asp Gln Asn Val
            180                 185                 190 ctg cac ccg att ttt gtg aag cag ttt aag gca ggg gta atg tgg cag     624
Leu His Pro Ile Phe Val Lys Gln Phe Lys Ala Gly Val Met Trp Gln
        195                 200                 205 gat gga tca aga aat cca aat cct aaa gca gac gga ttt ccg tat gtt     672
Asp Gly Ser Arg Asn Pro Asn Pro Lys Ala Asp Gly Phe Pro Tyr Val
    210                 215                 220 ttt acc gat gag gaa tta cgt tca gca aga gtt cct atc cta tta tta     720
Phe Thr Asp Glu Glu Leu Arg Ser Ala Arg Val Pro Ile Leu Leu Leu
225                 230                 235                 240 ctt ggt gaa cat gaa gtc atc tat gat ccc cac tca gcc ctg cac cga     768
Leu Gly Glu His Glu Val Ile Tyr Asp Pro His Ser Ala Leu His Arg
                245                 250                 255 gcc tct tca ttc gtt cct gat att gag gcg gaa gtc att aaa aat gcc     816
Ala Ser Ser Phe Val Pro Asp Ile Glu Ala Glu Val Ile Lys Asn Ala
            260                 265                 270 gga cat gtt tta tcg atg gaa caa ccc gct tac gta aat gaa cgt gta     864
Gly His Val Leu Ser Met Glu Gln Pro Ala Tyr Val Asn Glu Arg Val
```

```
Gly His Val Leu Ser Met Glu Gln Pro Ala Tyr Val Asn Glu Arg Val
            275                 280                 285
atg cgt ttt ttc aat gca gaa aca ggc att tca cgg taa                903
Met Arg Phe Phe Asn Ala Glu Thr Gly Ile Ser Arg
    290                 295                 300

<210> SEQ ID NO 18
<211> LENGTH: 300
<212> TYPE: PRT
<213> ORGANISM: Bacillus subtilis IFO101590

<400> SEQUENCE: 18

Met Ser Asn His Ser Ser Ile Pro Glu Leu Ser Asp Asn Gly Ile
1               5                   10                  15

Arg Tyr Tyr Gln Thr Tyr Asn Glu Ser Leu Ser Leu Trp Pro Val Arg
                20                  25                  30

Trp Glu Ser Phe Tyr Ile Ser Thr Arg Phe Gly Gln Thr His Val Ile
            35                  40                  45

Ala Ser Gly Pro Glu Asp Ala Pro Pro Leu Val Leu His Gly Ala
    50                  55                  60

Leu Phe Ser Ser Thr Met Trp Tyr Pro Asn Ile Ala Asp Trp Ser Ser
65              70                  75                  80

Lys Tyr Arg Thr Tyr Ala Val Asp Ile Ile Gly Asp Lys Asn Lys Ser
                85                  90                  95

Ile Pro Glu Asn Leu Ser Gly Thr Arg Thr Asp Tyr Ala Asn Trp Leu
            100                 105                 110

Leu Asp Val Phe Asp Asn Leu Gly Ile Glu Lys Ser His Met Ile Gly
        115                 120                 125

Leu Ser Leu Gly Gly Leu His Thr Met Asn Phe Leu Leu Arg Met Pro
    130                 135                 140

Glu Arg Val Lys Ser Ala Ala Ile Leu Ser Pro Ala Glu Thr Phe Leu
145                 150                 155                 160

Pro Phe His His Asp Phe Tyr Lys Tyr Ala Leu Gly Leu Thr Ala Ser
                165                 170                 175

Asn Gly Val Glu Thr Phe Leu Asn Trp Met Met Asn Asp Gln Asn Val
            180                 185                 190

Leu His Pro Ile Phe Val Lys Gln Phe Lys Ala Gly Val Met Trp Gln
        195                 200                 205

Asp Gly Ser Arg Asn Pro Asn Pro Lys Ala Asp Gly Phe Pro Tyr Val
    210                 215                 220

Phe Thr Asp Glu Glu Leu Arg Ser Ala Arg Val Pro Ile Leu Leu Leu
225                 230                 235                 240

Leu Gly Glu His Glu Val Ile Tyr Asp Pro His Ser Ala Leu His Arg
                245                 250                 255

Ala Ser Ser Phe Val Pro Asp Ile Glu Ala Glu Val Ile Lys Asn Ala
            260                 265                 270

Gly His Val Leu Ser Met Glu Gln Pro Ala Tyr Val Asn Glu Arg Val
        275                 280                 285

Met Arg Phe Phe Asn Ala Glu Thr Gly Ile Ser Arg
    290                 295                 300

<210> SEQ ID NO 19
<211> LENGTH: 30
<212> TYPE: DNA
<213> ORGANISM: Artificial Sequence
<220> FEATURE:
<223> OTHER INFORMATION: primer
```

```
<400> SEQUENCE: 19
cggaattcat gtcaaaccat tcatctagta                              30

<210> SEQ ID NO 20
<211> LENGTH: 30
<212> TYPE: DNA
<213> ORGANISM: Artificial Sequence
<220> FEATURE:
<223> OTHER INFORMATION: primer

<400> SEQUENCE: 20
gctctagatt accgtgaaat gcctgtttct                              30
```